US009708626B2

(12) United States Patent
Enenkel et al.

(10) Patent No.: US 9,708,626 B2
(45) Date of Patent: Jul. 18, 2017

(54) REGULATORY NUCLEIC ACID ELEMENTS

(71) Applicant: Boehringer Ingelheim Pharma GmbH & Co. KG, Ingelheim am Rhein (DE)

(72) Inventors: Barbara Enenkel, Warthausen (DE); Kerstin Assfalg, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/699,182

(22) Filed: Apr. 29, 2015

(65) Prior Publication Data
US 2015/0337333 A1 Nov. 26, 2015

Related U.S. Application Data

(60) Division of application No. 12/842,468, filed on Jul. 23, 2010, now Pat. No. 9,045,776, which is a continuation of application No. 11/762,240, filed on Jun. 13, 2007, now abandoned.

(30) Foreign Application Priority Data

Jul. 26, 2006 (EP) .................................... 06117862

(51) Int. Cl.
C12N 15/85 (2006.01)
C07K 14/47 (2006.01)
C12N 15/63 (2006.01)

(52) U.S. Cl.
CPC .............. *C12N 15/85* (2013.01); *C07K 14/47* (2013.01); *C12N 15/63* (2013.01); *C12N 2800/107* (2013.01); *C12N 2830/46* (2013.01); *C12N 2830/85* (2013.01)

(58) Field of Classification Search
None
See application file for complete search history.

(56) References Cited

U.S. PATENT DOCUMENTS

| | | | |
|---|---|---|---|
| 5,122,458 | A | 6/1992 | Post et al. |
| 6,027,915 | A | 2/2000 | Morris et al. |
| 6,063,598 | A | 5/2000 | Enenkel et al. |
| 6,271,346 | B1 | 8/2001 | Hauptmann et al. |
| 6,309,851 | B1 | 10/2001 | Taylor et al. |
| 7,344,886 | B2 | 3/2008 | Enenkel et al. |
| 7,384,744 | B2 | 6/2008 | Enenkel et al. |
| 7,732,181 | B2 | 6/2010 | Enenkel et al. |
| 8,338,179 | B2 | 12/2012 | Enenkel et al. |

FOREIGN PATENT DOCUMENTS

| | | |
|---|---|---|
| CA | 2234071 A1 | 5/1997 |
| CA | 2507664 A1 | 6/2004 |
| CA | 2507714 A1 | 6/2004 |
| EP | 0393438 A2 | 10/1990 |
| WO | 9208796 A1 | 5/1992 |
| WO | 9405785 A1 | 3/1994 |
| WO | 9428143 A1 | 12/1994 |
| WO | 9715664 A1 | 5/1997 |
| WO | 0034318 A1 | 6/2000 |
| WO | 0034326 A1 | 6/2000 |
| WO | 0034526 A1 | 6/2000 |
| WO | 0104306 A1 | 1/2001 |
| WO | 0127150 A2 | 4/2001 |
| WO | 02081677 A2 | 10/2002 |
| WO | 03004704 A2 | 1/2003 |
| WO | 2004050879 A1 | 6/2004 |
| WO | 2004050884 A2 | 6/2004 |

OTHER PUBLICATIONS

Adam, Mohammed A. et al. "Internal Initiation of Translation in Retroviral Vectors Carrying Picornavirus 5' Nontranslated Regions" Journal of Virology, (1991) vol. 65, No. 9, pp. 4985-4990.
Altschul, Stephen F. et al. "Basic Local Alignment Search Tool" Journal of Molecular Biology (1990) vol. 215, No. 3, pp. 403-410.
Altschul, Stephen F. et al. "Gapped BLAST and PSI-BLAST: a new generation of protein database search programs" Nucleic Acids Research (1997) vol. 25, No. 17, pp. 3389-3402.
Aronow, Bruce J. et al. "Dissecting a Locus Control Region: Facilitation of Enhancer Function by Extended Enhancer-Flanking Sequences" Molecular and Celluar Biology (1995) vol. 15, No. 2, pp. 1123-1135.
Baker, Jeanne E. et al. "A Novel Element Upstream of the $V_i2$ Gene in the Murine T Cell Receptor $_i$ Locus Cooperates with the 3' Enhancer to Act as a Locus Control Region" Journal of Experimental Medicine, (1999) vol. 190, No. 5, pp. 669-679.
Bell, Adam C. et al. "Stopped at the border: boundaries and insulators" Current Opinion in Genetics & Development (1999) vol. 9, pp. 191-198.
Bennett, Robert P. et al. "Fusion of Green Fluorescent Protein with the Zeocin TM-Resistance Marker Allows Visual Screening and Drug Selection of Transfected Eukaryotic Cells" Biotechniques (1998) vol. 24, No. 3, pp. 478-482.
C griseus promoter sequence: AC ADP74770; Enenkel et al., Sep. 9, 2004.
Chalfie, Martin et al. "Green Fluorescent Protein as a Marker for Gene Expression" Science (1994) vol. 263, pp. 802-805.
Cricetulus griseus UDP-N-acetylglucosamine: Acession No. U09453. Scocca et al., Jan. 12, 1996.
Davies, Monique V. et al. "The Sequence Context of the Initiation Codon in the Encephalomyocarditis Virus Leader Modulates Efficiency of Internal Translation Initiation" Journal of Virology (1992) vol. 66, No. 4, pp. 1924-1932.

(Continued)

*Primary Examiner* — Celine Qian
(74) *Attorney, Agent, or Firm* — Paula K. Wittmayer; Atabak R. Royaee

(57) ABSTRACT

The invention relates to DNA-sequences, especially transcription- or expression-enhancing elements (TE elements) and their use on an expression vector in conjunction with an enhancer, a promoter, a product gene and a selectable marker. TE elements bring about an increase in the expression of the product gene, particularly when stably integrated in the eukaryotic genome, preferably the CHO-DG44 genome.

8 Claims, 22 Drawing Sheets

(56) References Cited

OTHER PUBLICATIONS

Delgado, Sonia et al. "Initiation of DNA replication at CpG islands in mammalian chromosomes" EMBO Journal (1998) vol. 17, No. 8, pp. 2426-2435.
EMBL: Accession No: BX284634 Description: "Mouses DNA sequence from clone RP23-92B18 on chromosome 11 . . . " XP002409732 Creation date: Mar. 4, 2003.
Faisst, Steffen et al. "Compilation of vertebrate-encoded transcription factors" Nucleic Acids Research (1991) vol. 20, No. 1, pp. 3-26.
Gossen, Manfred et al "Inducible gene expression systems for higher eukaryotic cells" Current Opinion in Biotechnology (1994) vol. 5 pp. 516-520.
Haber, Daniel A. et al. "Chromosome-Mediated Transfer and Amplification of an Altered Mouse Dihydrofolate Reductase Gene" Somatic Cell Genetics (1982) vol. 8, No. 4, pp. 499-508
Hemann, Cord et al. "High-Copy Expression Vector Based on Amplification-Promoting Sequences." DNA and Cell Biology (1994) vol. 13, No. 4, pp. 437-445.
Hu, Shi-zhen, et al. "Minibody: A Novel Engineered Anti-Carcinoembryonic Antigen Antibody Fragment (Single-Chain Fv-Ch3) Which Exhibits Rapid, High-Level Targeting of Xenografts1" Cancer Research (1996) vol. 56, pp. 3055-3061.
Huston, James S. et al. "Protein engineering of antibody binding sites: Recovery of specific activity in an anti-digoxin single-chain Fv analogue produced in *Esherichia coli*" Proc. Natl. Acad. Sci. USA (1988) vol. 85, pp. 5879-5883.
International Search Report for PCT/EP2007/055954 mailed Oct. 30, 2007.
Jang, Sung K. et al. "Initiation of Protein Synthesis by Internal Entry of Ribosomes into the 5' Nontranslated Region of Encephalomyocarditis Virus RNA In Vivo" Journal of Virology, (1989) vol. 63, vol. 4, pp. 1651-1660.
Jenuwein, Thomas et al. "Extension of chromatin accessibility by nuclear matrix attachment regions" Nature (1997) vol. 385, pp. 269-272.
Kaufman, Randal J. "[42] Selection and Coamplification of Heterologous Genes in Mammalian Cells" Methods of Enzymology (1990) vol. 185, pp. 537-566.
Klehr, Dagmar et al. "Scaffold-Attached Regions from the Human Interferon b Domain Can be Used to Enhance the Stable Expression of Genes under the Control of Various Promoters" Biochemistry (1991) vol. 30, No. 5, pp. 1264-1270.
Kortt, Alexander A. et al. "Single-chain Fv fragments of anti-neuraminidase antibody NC10 containing five- and ten-residue linkers form dimers and with zero-residue linker a timer" Protein Engineering (1997) vol. 10, No. 4, pp. 423-433.
Kruger, Gudrun et al. "The -3.9 kb DNaseI hypersensitive site of the chicken lysozyme locus harbours an enhancer with unusual chromatin reorganizing activity" Elsevier Gene 236 (1999) pp. 63-77.
Kwaks, Ted H.J. et al. "Identification of anti-repressor elements that confer high and stable protein production in mammalian cells" Nature Biotechnology (2003) vol. 21, pp. 553-558.
Levy-Wilson, Beatriz, et al. "An Open Chromatin Structure in a Liver-Specific Enhancer That Confers High Level Expression to Human Apolipoprotein B Transgenes in Mice" Molecular Cell Biology Research Communications, (2000) vol. 4, pp. 206-211.
Li, Qiliang et al. "Locus control regions" Blood (2002) vol. 100, No. 9, pp. 3077-3086.
Lovejoy, Brett et al. "Crystal Structure of a Synthetic Triple-Stranded a-Helical Bundle" Science (1993) vol. 259, pp. 1288-1293.
McKnight, Robert A. et al. "Matrix-attachment regions can impart position-independent regulation of a tissue-specific gene in transgenic mice" Proc. Natl. Acad. Sci. USA (1992) vol. 89, pp. 6943-6947.
Monaco, Lucia et al. "Expression of recombinant human granulocyte colony-stimulating factor in CHO dhfr- cells: new insights into the in vitro amplification expression system" Gene (1996) 180, pp. 145-150.
Morgan, Richard A. "Retroviral vectors containing putative internal ribosome entry sites: development of a polycistronic gene transfer system and applications to human gene therapy" Nucleic Acids Research (1992) vol. 20, No. 6, pp. 1293-1299.
Mosser, D.D. et al. "Use of a Dicistronic Expression Cassette Encoding the Green Fluorescent Protein for the Screening and Selection of Cells Expressing Inducible Gene Products" BioTechniques (1997) 22, pp. 150-161.
Ohshima, Yasumi et al. "Signals for the Selection of a Splice Site in Pre-mRNA Computer Analysis of Splice Junction Sequences and Like Sequences" Journal of Molecular Biology (1987) vol. 195, pp. 247-259.
Ortiz, Benjamin D. et al. "A New Element within the T-Cell Receptor a Locus Required for Tissue-Specific Locus Control Region Activity" Molecular and Cell Biology (1999) vol. 19, No. 3, pp. 1901-1909.
Ortiz, Benjamin D. et al. "Adjacent DNA elements dominantly restrict the ubiquitous activity of a novel chromatin-opening region to specific tissues" EMBO Journal (1997) vol. 16, No. 16, pp. 5037-5045.
Pack, Peter et al. "Improved Bivalent Miniantibodies, with Identical Avidity as Whole Antibodies, Produced by High Cell Density Fermentation of *Escherichia coli*" Biotechnology (1993) vol. 11, pp. 1271-1277.
Pack, Peter et al. "Tetravalent Miniantibodies with High Avidity Assembling in *Escherichia coli*" Journal of Molecular Biology (1995) vol. 246, pp. 28-34.
Pelletier, Jerry et al. "Internal initiation of translation of eukaryotic mRNA directed by a sequence derived from poliovirus RNA" Nature (1988) vol. 334, pp. 320-325.
Perisic, Olga et al. "Crystal structure of a diabody, a bivalent antibody fragment" Structure (1994) vol. 2 pp. 1217-1226.
Pikaart, Michael J. et al. "Loss of transcriptional activity of a transgene is accompanied by DNA methylation and histone deacetylation and is prevented by insulators" Genes & Development (1998) vol. 12, pp. 2852-2862.
Poljak, Leonora et al. "SARs stimulate but do not confer position independent gene expression" Nucleic Acids Research (1994) vol. 22, No. 21, pp. 4386-4394.
Ramesh, N et al. "High-titer bicistronic retroviral vectors employing foot-and-mouth diseases virus internal ribosome entry site" Nucleic Acids Research (1996) vol. 24, No. 14, pp. 2697-2700.
Sambrook, J et al. "Molecular Cloning, A Laboratory Manual, Second Edition" (1989) 8 pgs.
Sautter, Kerstin et al. "Selection of High-Producing CHO Cells Using NPT Selection Marker with Reduced Enzyme Activity" Biotechnology and Bioengineering (2005) vol. 89, pp. 530-538.
Scocca, J.R. et al. Accession No. U09453. Definition: Cricetulus griseus UDP-N-acetylglucosamine: dolichyl phosphate N-acetylglucosamine 1-phosphate transferase gene, partial cds. Title: "Genomic organization and expression of hamster UDP-N-acetylglucosamine:dolichyl phosphate N-acetylglucosaminyl phosphoryl transferase" Glycobiology 5 (1) 129-136 (1995).
Simonsen, Christian C. et al. "Isolation and expression of an altered mouse dihydrofolate reductase cDNA" Proc. Natl. Acad. Sci. USA, (1983) vol. 80, pp. 2495-2499.
Stief, Aribert "A nuclear DNA attachment element mediates elevated and position-independent gene activity" Nature (1989) vol. 341, pp. 343-345.
Sugimoto, Yoshikazu et al. "Efficient Expression of Drug-selectable Genes in Retroviral Vectors Under Control of an Internal Ribosome Entry Site" Biotechnology (1994) vol. 12, pp. 694-698.
Thompson, W. Reid et al. "A MyoD1-independent Muscle-specific Enhancer Controls the Expression of the β-Myosin Heavy Chain Gene in Skeletal and Cardiac Muscle Cells*" The Journal of Biological Chemistry (1991) vol. 266, No. 33, pp. 22678-22688.
Udvardy, Andor "Dividing the empire: boundary chromatin elements delimit the territory of enhancers" EMBO Journal (1999) vol. 18, No. 1, pp. 1-8.
Udvardy, Andor et al. "The 87A7 Chromomere Indentification of Novel Chromatin Structures Flanking the Heat Shock Locus that may Define the Boundaries of Higher Order Domains" Journal of Molecular Biology, (1985) vol. 185, No. 2, pp. 341-358.

(56) References Cited

OTHER PUBLICATIONS

Urlaub, Gail et al. "Deletion of the Diploid Dihydrofolate Reductase Locus from Cultured Mammalian Cells" Cell, (1983) vol. 33, pp. 405-412.
Urlaub, Gail et al. "Effect of Gamma Rays at the Dihydrofolate Reductase Locus: Deletions and Inversions" Somatic Cell and Molecular Genetics, (1986) vol. 12, No. 6, pp. 555-566.
Wei, Xing-Cheng et al. "Characterization of Chromatin Structure and Enhancer Elements for Murine Recombination Activating Gene-21" Journal of Immunology, (2002) vol. 169, pp. 873-881.
Werner, Rolf G. et al. "Appropriate Mammalian Expression Systems for Biopharmaceuticals" Arzneimittel-Forschung (1998) vol. 48, pp. 870-880.
Wigler, M. et al. "Transformation of mammalian cells with an amplifiable dominant-acting gene" (1980) Proc. Natl. Acad. Sci. Usa (1980) vol. 77, No. 6, pp. 3567-3570.
Yoshimura, Teizo et al. "Human monocyte chemoattractant protein-1 (MCP-1) Full length cDNA cloning, expression in mitogen-stimulated blood mononuclear leukocytes, and sequence similarity to mouse competence gene JE" FEBS Letters (1989) vol. 244, No. 2, pp. 487-493.
Zahn-Zabal, Monique et al. "Development of stable cell lines for production or regulated expression using matrix attachment regions" Journal of Biotechnology (2001) vol. 87, pp. 29-42.
Ausubel, FM et al. "Current Protocols in Molecular Biology" Greene Publishing Associates & Wiley Interscience (1994).
Chamov, S.M. et al. "Antibody Fusion Proteins" Wiley-Liss Inc. (1999).
Harris, et al. "Protein Purification: A Practical Approach" Pickwood & Hames, IRL Press (1995).
Scopes, R. "Protein Purification" Springer Verlag (1988).

```
  1  CCATGAGAGC CTGAAGACCT GAGTTGATAC CCAGAACCCA GATCAAGATG GAGGAGAGAA CCAGCCCCAC
 71  GGTACTCTCG GACTTCTGGA CTCAACTATG GGTCTTGGGT CTAGTTCTAC CTCCTCTCTT GGTCGGGGTG
141  TAAGCTGTCC CCTGACCCCC ATAAATCCCT CCCTGTCCAG TTATGCCACA CAATGATAGG TGAATACAGA
211  ATTCGACAGG GGACTGGGGG TATTTACGGA GGGACAGGTC AATACGGTGT GTTACTATCC ACTTATGTCT
281  AAAACACCCT TCCTTTAGAC ACTAAGCGGA TTCCTCTTAC GCATACCAGT TAAGTGATAG TTCTTAGGCT
351  TTTTGTGGGA AGGAAATCTG TGATTCGCCT AAGGAGAATG CGTATGGTCA ATTCACTATC AAGAATCCGA
421  TCAACTCAGC ACTTAAAAAA GTTTATATTT TGCAATGCTG GGGACTAAAT TAGGGTGTG CACATGCTAA
491  AGTTGAGTCG TGAAATTTTT CAAATATAAA ACGTTACGAC CCCTGATTTA ATCCAACAC GTGTACGATT
561  GTAAGCACTC TACTTTTGTA TCACATTTTA ATAATTGTAA GAATTAATTC GTGAAATAGT AGCTGAGACA
631  CATTCGTGAG ATGAAAACAT AGTGTAAAAT TATTAACATT CTTAATTAAG CACTTTATCA TCGACTCTGT
701  ATAGATTTGT TTCTTTCATG TGGAACTGC TGTGTGTGCT TCTTGCTGAT GCAAACAAGG TCAAATACTT
771  TATCTAAACA AAGAAAGTAC ACCCTTGACG AGAACGACTA CGTTTGTTCC AGTTTATGAA
```

FIG. 3A

```
 841  TTTTCCCCCA  TCACTTAGAC  AGCCATATTT  AAACGTAGTG  GAGCCAAGCT  GGGGTGGTGG  CCCACACCTT
      AAAAGGGGGT  AGTGAATCTG  TCGGTATAAA  TTTGCATCAC  CTCGGTCCGA  CCCCACCACC  GGGTGTGGAA
 911  TAATCCCAGC  ACTCCAGAAG  GCAGAGTAG   GCGGATCTC   GTGGGTTTGA  GACCAGCCTG  GTCTACAAGA
      ATTAGGGTCG  TGAGGTCTTC  CGTCTCCATC  CGCCTAGAGA  CACCCAAACT  CTGGTCGGAC  CAGATGTTCT
 981  GCTAGTTCCA  GGACAGCCTC  CAAAGCCATA  GAGAAACCCT  ATCTCAAAAA  ACTGAAACAA  CAACAACAAC
      CGATCAAGGT  CCTGTCGGAG  GTTTCGGTAT  CTCTTTGGGA  TAGAGTTTTT  TGACTTTGTT  GTTGTTGTTG
1051  AAAACAAAAT  AAAAAAACAA  CAAAGAAATC  TTAGTGGTTC  AGTGGTTCCA  CACACAGGAA  AGTAGAAAGG
      TTTTGTTTTA  TTTTTTTGTT  GTTTTCTTAG  AATCACCAAG  TCACCAAGGT  GTGTCCTT    TCATCTTTCC
1121  GCCTTGATGG  GAAGTTTTC   AGAGGGAGGA  GTATGGATGA  GACAGGATGA  TAGTGAAAAG  AACTCAAATT
      CGGAACTACC  CTTCCAAAAG  TCTCCCTCCT  CATACCTACT  CTGTCCTACT  ATCACTTTTC  TTGAGTTTAA
1191  AATTAAATAT  TTGAACTAAT  CTAAGAATAA  AAGCTAAAAT  ATTTAAAATT  ACAGTCAGGT  AGTGGTGGTG
      TTAATTTATA  AACTTGATTA  GATTCTTATT  TTCGATTTTA  TAAATTTTAA  TGTCAGTCCA  TCACCACCAC
1261  CAGAGGCTA   AGTTGGTAGA  CACAGTGAGA  TCCAGGCCAG  GTATGGAGAG  CTAGTGAGAC  CTTGTTCAAA
      GTCTCCCGAT  TCAACCATCT  GTGTCACTCT  AGGTCCGGTC  CATACCTCTC  GATCACTCTG  GAACAAGTTT
1331  TAACTAATAA  AATATACAAA  ATAAAGGAGA  CACCACAATA  ATTTTGAAAT  GTAAAAGACT  AAATTTACCT
      ATTGATTATT  TTATATGTTT  TATTCCTTCT  GTGGTGTTAT  CATTTTCTGA  CATTTTCTGA  TTTAAATGAA
1401  TTTATATTGA  TGAGTTGGAT  AAAAAAATCA  ATTTACCAGA  GAACATAAAG  TAGTCCCATC  AAAGACAAAA
      AAATAAT     ACTCAACCTA  TTTTTTTAGT  TAAATGGTCT  CTTGTATTTC  ATCAGGGTAG  TTTCTGTTTT
1471  GCAATATATG  ATTAAACTCT  AATTTAAAAG  TTTGTTAGAG  CCTGCAAACG  TGGCACATAC  CTTTAATCCC
      CGTTATATAC  TAATTTGAGA  TTAAATTTTC  AAACAATCTC  GGACCGTTGC  ACCGTGTATG  GAAATTAGGG
1541  AGCACCAGG   AGACAGAGGC  CATCCCTGGTC  TAAAAAGTGA  TCTCCAGGAC  AGCCATGGCT  ATTACACAGA
      TCGTGGTCCC  TCTGTCTCCG  GTAGGACCAG  ATTTTTCACT  AGAGGTCCTG  TCGGTACCGA  TAATGTGTCT
1611  GAAACCCTGT  CTGAAAAAAC  AAAAAATTAG  TGTCCATGTG  TAAATGTGTG  GAGTATGCTT  GTCATGCCAC
      CTTTGGACA   GACCTTTTG   TTTTTTAATC  ACAGGTACAC  ATTTACACAC  CTCATACGAA  CAGTACGGTG
```

FIG. 3B

```
1681  ATACAGAGCT AGAGGGCAGT TTATGGGAGT CAGTTCCTAT TCTTCCTTTA TGGGGGACCT GGGGACTGAA
1751  TATGTCTCCA TCTCCCGTCA AATACCCTCA GTCCAAGGATA AGAAGGAAAT ACCCCCTGGA CCCCTGACTT
1821  CTCAGTCAT CAGGCTTGGC AGAAAGTGCA TTAGCTCACG GAGCCTTATC ATTGGCGAAA GCTCTCTCAA
1891  GAGTCCAGTA GTCCGAACCG TCTTTCACGT AATCGAGTGC CTCGGAATAG TAACCGCTTT CGAGAGAGTT
1961  GTAGAAAATC AATGTGTTTG CTCATAGTGC AATCATTATG TTTCGAGAGG GGAAGGGTAC AATCGTTGGG
2031  CATCTTTTAG TTACACAAAC GAGTATCACG TTAGTAATAC AAAGCTCTCC CCTTCCCATG TTAGCAACCC
2101  GCATGTGTGG TCACATCTGA ATAGCCAGTAG CTCCCTAGGA GAGGGATCCT CAAGTTCTTT GGTGGTGTAT
2171  CGTACACACC AGTGTAGACT TATCGTCATC GAGGGATCCT CTTAATTAAG GTTCAAGAAA CCACACATA
2241  CAATGCCCTT AAAGGGGTCA ACAACTTTTT TTCCCTCTGA CAAAACTATC TTCTTATGTC CTTGTCCCTC
2311  GTTACGGGAA TTTCCCCAGT TGTTTGAAAAA AAGGGAGACT GTTTTTGATAG AAGAATACAG GAACAGGAG
2381  ATATTTGAAG TATTTTATTC TTTGCAGTGT TGAATATCAA TTCCTAGCACC TCAGACATGT TAGGTAAGTA
2451  TATAAACTTC ATAAAATAAG AAACGTCACA ACTTATAGTT AAGATCGTGG AGTCTGTACA ATCCATTCAT
```
FIG. 3C

```
2521  TCAGAGATCC ACCTGCCTCT GCCTCCTGAG TGCTGGGATT AAAGGCATGC GCCACCAACG CTTGGCTCTA
2591  AGTCTCTAGG TGGACGGAGA CGGAGGACTC ACGACCCTAA TTTCCGTACG CGGTGGTTGC GAACCGAGAT
2661  CCTAATTTTA AAAGAGATTG TGTGTCACAA GGGTGTCATG TCGCCCTGCA ACCACCCCCC CCCCAAAAAA
2731  GGATTAAAAT TTTCTCTAAC ACACAGTGTT CCCACAGTAC AGCGGGACGT TGGTGGGGGG GGGGTTTTTT
2801  AAAAAAAAAA AAACTTCACT GAAGCTGAAG CACGATGATT TGGTTACTCT GGCTGGCCAA TGAGCTCTAG
2871  TTTTTTTTTT TTTGAAGTGA CTTCGACTTC GTGCTACTAA ACCAATGAGA CCCGACCGTT ACTCGAGATC
2941  GGAGTCTCCT GTCAAACAGA ATCTCAACAG GCGCAGCAGT CTTTTTTAAA GTGGGGTTAC AACACAGGTT
3011  CCTCAGAGGA CAGTTTGTCT TAGAGTTGTC CGGTCGTCA GAAAAAATTT CACCCCAATG TTGTGTCCAA
3081  TTTGCATATC AGGCATTTTA TCTAAGCTAT TTCCCAGCCA AAAATGTGTA TTTTGGAGGC AGCAGAGCTA
3151  AAACGTATAG TCCGTAAAAT AGATTCGATA AAGGGTCGGT TTTTACACAT AAAACCTCCG TCGTCTCGAT
3221  ATAGATTAAA ATGAGGAAAG AGCCCACACA GGTTATTAGG AAGATAAGCA TCTTTCTTTAT ATAAAACAAA
3291  TATCTAATTT TACTCCCTTC TCGGGTGTGT CCAATAATCC TTCTATTCGT AGAAGAAATA TATTTTGTTT
3361  ACCAAACCAA ACTGGAGGAG GTCTACCTTT AGGGATGGAA GAAAAGACAT TTAGAGGGTG CAATAGAAAG
3431  TGGTTTGGTT TGACCTCCTC CAGATGGAAA TCCCTACCTT CTTTTCTGTA AATCTCCCAC GTTATCTTTC
3501  GGCACTGAGT TTGTGAGGTG GAGGACTGGG AGAGGGCGCA ACCGCTTTAA CTGTCCTGTT TTGCCTATTT
3571  CCGTGACTCA AACACTCCAC CTCCCTGACCC TCTCCCGCGT TGGCGAAATT GACAGAGACAA AACGATAAA
3641  TTTGGGGACA GCACATGTTC CTATTTTTCC CAGGATGGGC AATCCCACG TCCAAACTTG CGGTCGAGGA
3711  AAACCCCTGT CGTGTACAAG GATAAAAAGG GTCCTACCCG TTAGAGGTGC AGGTTTGAAC GCCAGCTCCT
3781  CTACAGTCAT TTTGCAGGTT TCCTTTACTGT ATGGCTTTTA AAACGTGCAA AGGTGACCAT TAACCGTTTC
3851  GATGTCAGTA AAACGTCCAA AGGAATGACA TACCGAAAAT TTCCTCTGAC TCCACTGGTA ATTGGCAAAG
3921  ACGCTGGGAG GGCACGTGCG GCTCAGATGC TTTGCACGTT TGAGGCCAG GAGGGGCTA CACGGAAGAG
3991  TGCGACCCTC CCGTGCACGC CGAGTCTACG AAGGAGACTG ACTCCCGGTC CTCCCCGAT GTGCCTTCTC
4061  GCCACACCCG CACTTGGGAA GACTCGATTT GGGCTTCAGC TGGCTGAGAC GCCCCCAGCAG GCTCCTCGGC
4131  CGGTGTGGGC GTGAACCCTT CTGAGCTAAA CCCGAAGTCG ACCGACTCTG ACCGACTCGT CGGGGTCGTC CGAGGAGCCG
```

FIG. 3D

```
3361  TACACCTTCA GCCCCGAATG CCTTTCCGGC CATAACCCTT CCCTTCTAGG CATTTCCGGC GAGGACCCAC
3431  ATGTGGAAGT CGGGCTTAC  GGAAGGCCGG GTATTGGAA  GGGAAGATCC GTAAAGCCG  CTCCTGGGTG
3501  CCTCGGCCA  AACATTCGGC CCCATCCCCC GTCCTCACC  TGAATCTCTA ACTCTGACTC CAGAGTTTAG
3571  GGAGCGCGGT TTGTAAGCCG GGGTAGGCGG CCAGGAGTGG ACTTAGAGAT TGAGACTGAG GTCTCAAATC
3641  AGACTATAAC CAGATAGCCC GGATGTGTGG AACTGCATCT TGGGACGAGT AGTTTTAGCA AAAAGAAAGC
3711  TCTGATATTG GTCTATCGGG CCTACACACC TTGACGTAGA ACCCTGCTCA TCAAATCGT  TTTTCTTTCG
3781  GACGAAAAAC TACAATTCCC AGACAGACTT GTGTTACCTC TCTTCTCATG CTAAACAAGC CCCCTTTAAA
3851  CTGCTTTTG  ATGTTAAGG  TCTGTCTGAA CACAATGGAC AGAAGAGTAG GATTGTTCG  GGGAAATTT
3921  GGAAAGCCCC TCTTAGTCGC ATCGACTGTG TAAGAAAGGC GTTTGAAACA TTTTAATGTT GGGCACACCG
3991  CCTTTCGGG  AGAATCAGCG TAGCTGAACA ATTCTTTCCG CAAACTTTGT AAAATTACAA CCCGTGTGGC
4061  TTTCGAGGAC CGAAATGAGA AAGAGCATAG GGAAACGGAG CGCCCGAGCT AGTCTGGCAC TGCGTTAGAC
4131  AAAGCTCCTG GCTTTACTCT TTCTCGTATC CCTTTGCCTC GCGGGCTCCA TCAGACCGTG ACGCAATCTG
4201  AGCCGCGG
      TCGGCGCC
```

FIG. 3E

| TE element | SEQ ID Nr. | Start (bp) | End (bp) | Length (bp) | Synthesis Primer |
|---|---|---|---|---|---|
| A | 1 | 1 | 3788 | 3788 | ----- |
| 00 | 2 | 1579 | 3788 | 2210 | ----- |
| 01 | 3 | 513 | 3517 | 3005 | TE for 5, TE rev 4 |
| 02 | 4 | 1001 | 3517 | 2517 | TE for 6, TE rev 4 |
| 03 | 5 | 1529 | 3517 | 1989 | TE for 7, TE rev 4 |
| 04 | 6 | 2006 | 3517 | 1512 | TE for 8, TE rev 4 |
| 05 | 7 | 2505 | 3517 | 1013 | TE for 9, TE rev 4 |
| 06 | 8 | 3137 | 3517 | 381 | TE for 10, TE rev 4 |
| 07 | 9 | 9 | 537 | 529 | TE for 4, TE rev 5 |
| 08 | 10 | 9 | 1023 | 1015 | TE for 4, TE rev 6 |
| 09 | 11 | 9 | 1549 | 1541 | TE for 4, TE rev 7 |
| 10 | 12 | 9 | 2028 | 2020 | TE for 4, TE rev 8 |
| 11 | 13 | 9 | 2524 | 2516 | TE for 4, TE rev 9 |
| 12 | 14 | 9 | 3156 | 3148 | TE for 4, TE rev 10 |
| 13 | 15 | 513 | 1023 | 511 | TE for 5, TE rev 6 |
| 14 | 16 | 1001 | 1549 | 549 | TE for 6, TE rev 7 |
| 15 | 17 | 513 | 1549 | 1037 | TE for 5, TE rev 7 |
| 16 | 18 | 1529 | 2028 | 500 | TE for 7, TE rev 8 |
| 17 | 19 | 1001 | 2028 | 1028 | TE for 6, TE rev 8 |
| 18 | 20 | 513 | 2028 | 1516 | TE for 5, TE rev 8 |
| 21 | 21 | 3137 | 3517 | 381 | TE for 10, TE rev 4 |

FIG. 5

| Primer | Sequence (5' – 3') | Element |
|---|---|---|
| TE for 4 | CTATGAGGATCCGCCTGAAGACCTGAGTTGATAC (SEQ ID NO: 22) | 07, 08, 09, 10, 11, 12 |
| TE for 5 | TATGCAGGATCCGTTGCTATTTTAGAGACAGATTC (SEQ ID NO:23) | 01, 13, 15, 18 |
| TE for 6 | TATGCAGGATCCCAAAGCCATAGAGAAACCCTATC (SEQ ID NO:24) | 02, 14, 17 |
| TE for 7 | TATGCAGGATCCACCTTTAATCCCAGCACCAGG (SEQ ID NO:25) | 03, 16 |
| TE for 8 | CTATGAGGATCCCTATCTTCTTATGTCCTTGTCCC (SEQ ID NO:26) | 04 |
| TE for 9 | TATGCAGGATCCCAGGCTGGTCTCGAACTCAG (SEQ ID NO:27) | 05 |
| TE for 10 | CTATGAGGATCCCTTGCGGTCGAGGACTACAG (SEQ ID NO:28) | 06 |
| TE for 11 | CTATGATGTACAGCCTGAAGACCTGAGTTGATAC (SEQ ID NO:29) | 08 (rev.Orientierung), 09 (rev.Orientierung) |
| TE rev 4 | ATTGCATGTACACTATCTGGTTATAGTCTCTAAACTCTG (SEQ ID NO:30) | 01, 02, 03, 04, 05, 06 |
| TE rev 5 | ATAGCATGTACAGAAATCCTGTCTCTAAAATAGCAAC (SEQ ID NO:31) | 07 |
| TE rev 6 | ATAGCATGTACAGATAGGGTTTCTCTATGGCTTTG (SEQ ID NO:32) | 08, 13 |
| TE rev 7 | ATACGATGTACACCTGGTGCTGGGATTAAAGGT (SEQ ID NO:33) | 09, 14, 15 |
| TE rev 8 | ATAGCATGTACAGGGACAAGGACATAAGAAGATAG (SEQ ID NO:34) | 10, 16, 17, 18 |
| TE rev 9 | TAGTTATGTACACTGAGTTCGAGACCAGCCTG (SEQ ID NO:35) | 11 |
| TE rev 10 | ATAGCATGTACACTGTAGTCCTCGACCGCAAG (SEQ ID NO:36) | 12 |
| TE rev 11 | ATACGAGGATCCCCCTGGTGCTGGGATTAAAGGT (SEQ ID NO:37) | 09 (rev. Orientierung) |
| TE rev 12 | ATAGCAGGATCCGATAGGGTTTCTCTATGGCTTTG (SEQ ID NO:38) | 08 (rev. Orientierung) |

FIG. 6

| | TE Element | Enhancement Factor Specific Productivity |
|---|---|---|
| Series A | 00 (reverse orientation) | 1,8 |
| | 00 (direct orientation) | 2,0 |
| | Control | 1,0 |
| Series B | 00 (reverse orientation) | 1,9 |
| | 00 (direct orientation) | 1,7 |
| | Control | 1,0 |
| Series C | 01 | 4,1 |
| | 02 | 4,5 |
| | 05 | 0,4 |
| | 06 | 2,5 |
| | 08 | 5,3 |
| | 09 | 0,4 |
| | Control | 1,0 |
| Series D | 03 | 3,9 |
| | 10 | 2,2 |
| | 11 | 2,0 |
| | 12 | 1,6 |
| | Control | 1,0 |

FIG. 9B

| TE Element | Enhancement Factor Specific Productivity |
|---|---|
| Control | 1.0 |
| Element 01 | 4.8 |
| Element 02 | 6.8 |
| Element 03 | 2.6 |
| Element 04 | 3.1 |
| Element 05 | 1.1 |
| Element 06 | 3.2 |
| Element 07 | 3.5 |
| Element 08 | 6.0 |
| Element 09 | 1.1 |
| Element 10 | 2.6 |
| Element 11 | 2.4 |
| Element 12 | 1.9 |

FIG. 10B

REGULATORY NUCLEIC ACID ELEMENTS

This application claims priority benefit from European application EP 06 117 862.0, filed Jul. 26, 2006, which is incorporated herein in its entirety.

FIELD OF THE INVENTION

The invention relates to cis-active nucleic acid sequences, so-called TE elements. The TE elements preferably originate from the CHO genome. Their use in expression vectors, for example, in stable cell populations permits at least twice as high an expression of a gene of interest in a desired chromosome locus compared with vectors previously used.

BACKGROUND TO THE INVENTION

Mammalian cells are the preferred host cells for the production of complex biopharmaceutical proteins as the post-translational modifications are human-compatible both functionally and from a pharmacokinetic point of view. The main relevant cells types are hydridomas, myelomas, CHO (Chinese Hamster Ovary) cells and BHK (Baby Hampster Kidney) cells. The host cells are increasingly cultivated under serum- and protein-free production conditions. The reasons for this are the associated reduction in costs, the reduced interference in the purification of the recombinant protein and the reduction of the potential for introducing pathogens (e.g. prions and viruses). The use of CHO cells as host cells is becoming more and more widespread as these cells adapt to suspension growth in serum- and protein-free medium and moreover are regarded and accepted as safe production cells by the regulatory bodies.

In order to produce a stable mammalian cell line which expresses a heterologous gene of interest, the heterologous gene is generally introduced into the desired cell line together with a selectable marker gene, such as neomycin phosphotransferase (NPT), by transfection. The heterologous gene and the selectable marker gene can be expressed in a host cell, starting from an individual or separate co-transfected vectors. Two to three days after the transfection the transfected cells are transferred into medium containing a selective agent, e.g. G418 when using the neomycin-phosphotransferase gene (NPT gene) and cultivated for a few weeks under these selective conditions. The emergent resistant cells which have integrated the exogenous DNA can be isolated and investigated for the expression of the desired gene product (gene of interest).

For biopharmaceutical production, cell lines with a high stable productivity are required. The expression vectors for production cells are equipped with strong, usually constitutively expressing promoters and enhancers such as CMV enhancer and promoter, for example, to allow high product expression. As the expression of the product has to be guaranteed over the longest possible time, cells are selected which have the product gene stably integrated in their genome. This is done with selectable markers such as e.g. neomycin-phosphotransferase (NPT) and dihydrofolate reductase (DHFR).

By the chance integration of the expression vectors in the host cell genome, cells are obtained with different levels of expression of the desired gene product, as its expression is not determined solely by the strength of the previous promoter or the promoter/enhancer combination. The chromatin structure present at the integration site can affect the level of expression both negatively and positively. Increasingly, therefore, cis-active elements which positively influence the expression at the chromatin level are integrated in expression vectors. These include locus control regions (LCR) which occur for example in the 5' region of the β-globin genes (Li et al., 2002) and in the 3' region of the TCRα gene. They cause high tissue-specific expression of a coupled transgene in the chromatin, which is characterised by its independence of position and dependence on copy number. These properties indicate that LCRs are capable of opening chromatin in their native tissue (Ortiz et al., 1997). There are various forms of β-thalassaemia in which the β-globin locus is intact but is not expressed. The reason for the lack of expression is a major deletion in the 5' direction of the β-globin genes. The deletion of this β-globin LCR leads to a closed chromatin configuration which extends over the entire locus and leads to suppression of gene expression (Li et al., 2002). LCRs colocalise with DNAse I-hypersensitive sites (HS) in the chromatin of expressing cells. The occurrence of HS also indicates open chomatin. The HS contain a series of different general and tissue-specific binding sites for transcription factors. By the interaction of the transcription factors with the DNA the open chromatin structure of HS is produced (Li et al., 2002). Many LCRs are known to be made up of a number of HS the functions of which can be more or less separated from one another. The TCRα gene for example is expressed under endogenous control only in T-cell tissue. The locus exists in various chomatin modes depending on the tissue and expression status. In the 3' region it has a locus control region which has 8 HS. HS 2-6, a 6 kb partial fragment of the LCR, has a chromatin-opening activity and is not tissue specific. The tissue specificity is imparted to the T-cell-specific expression in the thymus by HS7, 8 and 1 (3 kb). Only in the complete combination of all the HS is the TCRαLCR functionally complete (Ortiz et al., 1997). A more precise subdivision and specification of the individual HS functions of the TCRαLCR can be found in (Ortiz et al., 1999). This Example shows that LCRs are functionally very complex and may be made up of different control elements such as enhancers, silencers and isolators. Other Examples of the division of the LCR functions between various domains are the TCRγ locus and β-globin locus. The former is made up of the DNAse I-hypersensitive site HsA and the enhancer $3'E_{C\gamma 1}$. The TCRγ-LCR, in addition to having its usual functions, is also thought to play a part in the recombination of the TCRγ genes (Baker et al., 1999). The β-globin locus has five HS with distinguishable functions which also require the tissue-specific promoter in order to function fully. LCRs could also play another important role in the tissue-specific demethylation of DNA, as DNA methylation results in a closed chromatin structure and the inactivation of genes. A mechanism of activity which activates gene expression by increased histone acetylation would also be possible (Li et al., 2002).

Scaffold/Matrix Attachment Regions (S/MARs) are DNA sequences which bind with a high affinity in vitro to components of the matrix or the scaffold of the cell nucleus. They form the structural and possibly also functional boundaries of chromatin domains (Zahn-Zabal et al., 2001). S/MARs are capable of interacting with enhancers and of locally increasing the accessibility of the DNA in the chromatin and in this way can increase the expression of stably integrated heterologous genes in cell lines, transgenic animals and plants (Klehr et al., 1991; Stief et al., 1989; Jenuwein et al., 1997; Zahn-Zabal et al., 2001). However they cannot totally shield a chromosomal locus from nearby elements in order to allow position-independent expression (Poljak et al., 1994). The effect of the MARs can be used to increase the proportion of (highly) expressing cell clones or transgenic animals in a transfection experiment (McKnight et al., 1992; Zahn-Zabal et al., 2001). However, MARs have also been reported which do not impart high expression but play an important part in the correct regulation of development-specific genes (McKnight et al., 1992).

Isolators are defined as a neutral boundary between neighbouring regions which influence one another, e.g. between active and inactive chromatin (boundary elements). They may restrict the effect of enhancers or isolate entire DNA domains against them and shield stably transfected reporter genes from positional effects (Bell and Felsenfeld, 1999; Udvardy, 1999). Thus, these elements render the expression independent of the genomic position. They may also prevent the silencing of transgenes in the absence of selection pressure (Pikaart et al., 1998). Another presumed function of isolators is the restriction of replication territories (Bell and Felsenfeld, 1999). The first isolators that were described are scs and scs' from Drosophila. They constitute the boundary for the hsp70 heat shock genes and suppress positional effects (Udvardy et al., 1985).

As another element with an isolating function, a GC-rich fragment from the dhfr gene (Chinese Hamster) was found, containing CpG islands (Poljak et al., 1994). The fragment on its own exhibited no influence whatever on reporter gene expression. Situated between an expression promoting SAR and the reporter gene, however, the fragment was able to substantially prevent the expression-enhancing effect of the SAR element. Possibly, this GC-rich fragment blocks the chromatin-opening mechanism of the SAR element and consequently acts as an isolator. Elements with extended CPG islands are methylated with a higher probability as they are recognised by a DNA methyltransferase which converts cytosine into 5-methylcytosine. Consequently, inactive chomatin is formed (Poljak et al., 1994).

Aronow and colleagues defined in the first intron of the human ADA gene (Adenosin deaminase) a new regulatory element which substantially contributes to expression which is dependent on gene copy number but independent of position (Aronow et al., 1995). The element is up to 1 kb in size and only functional when it flanks a 200 bp T-cell-specific enhancer. If only one of the two segments is present or if the segments are wrongly arranged in their sequence and orientation, the element is non-functional as this prevents the formation of DNAse I-hypersensitive sites on the enhancer.

In their Patent WO 02/081677 the firm Cobra Therapeutics describe another chromatin-influencing element. The Ubiquitous Chromatin Opening Elements (UCOEs) are responsible for an open chromatin structure in chromosomal regions with ubiquitously expressed household genes (human hnRNP A2 gene, human β-actin gene, human PDCD2 gene). All these genes have CpG-rich islands in the untranslated regions which are relatively weakly methylated. The absence of methylation of CpG islands indicates that there is active chromatin at this point. The UCOEs help to provide a strength of expression which is independent of the genomic environment and the nature of the cell or tissue.

The firm Immunex also describes cis-active DNA sequences which bring about an increase in expression (U.S. Pat. No. 6,027,915, U.S. Pat. No. 6,309,851). The element referred to as the expression augmenting sequence element (EASE) demands a high expression of recombinant proteins in mammalian cells, is not active in transient expression systems and does not have the typical sequence properties found in LCRs and S/MARs. It is also not a sequence which codes for a trans-activating protein as it does not contain an open reading frame. The fragment is 14.5 kb long, originates from the genomic DNA of CHO cells and can increase the expression of a stably integrated reporter gene eight fold. Over 50% of the activity of the element is restricted to a 1.8 kb long segment, while the first 600 base pairs of this segment are essential for correct function. An additional property of sequence sections with a high EASE activity is the presence of a number of HMG-1(Y) binding sites. HMG-I(Y) proteins belong to the family of the high mobility group non-histone chromatin proteins. They are also referred to as "architechtonic transcription factors" and form a new category of trans-regulators of mammalian genes. HMG-I(Y) proteins recognise 80-rich sequences and bind to their so-called AT hooks (DNA-binding domains) in the small DNA fork. This can lead to local changes in the DNA topology and consequently to altered gene expression.

The authors of U.S. Pat. No. 6,309,841 presume that the effects of EASE are connected with the MTX-induced amplification of the integrated plasmid. In MTX-induced gene amplification, so-called breakage fusion bridge cycles occur. It is easy to imagine a role for the HMG-I(Y) proteins in the structural alteration of the DNA which lead to the formation and removal of the DNA breakages.

Other elements for increasing gene expression in mammalian cells are described in Kwaks et al., 2003. These so-called STAR elements (Stimulatory and Anti-Repressor Elements) originate from the screening of a human gene library with 500 to 2100 bp DNA fragments. The screening was carried out using a specially designed reporter plasmid. The expression of the reporter gene was only possible when it was functionally linked with an anti-repressor element from the human gene bank. With the STAR elements thus obtained the authors were able to protect transgenes from positional effects in the genome of mammalian cells. A comparison with the mouse genome showed that the majority of these STAR elements occur in both the human and the murine genome and are highly conserved within these two species.

A major problem in establishing cell lines with a high expression of the desired protein arises from the random and undirected integration of the recombinant vector in transcription-active or -inactive loci of the host cell genome. As a result, a population of cells is obtained which show completely different expression rates for the heterologous gene, while the productivity of the cells generally follows a normal distribution. In order to identify cell clones which have a very high expression of the heterologous gene of interest it is therefore necessary to check and test a number of clones, resulting in high expenditure of time, labour and costs. Attempts at improving the vector system used for the transfection are therefore directed at even allowing or increasing the transcription of a stably integrated transgene by the use of suitably cis-active elements. The cis-active elements which act at the chromatin level include for example the locus control regions, scaffold-matrix attachment regions, isolators, etc., already described. Some of these elements shield certain genes from the influences of the surrounding chromatin. Others exhibit an enhancer-like activity, although this is restricted to stably integrated constructs. Yet other elements combine several of these functions in themselves. Often it is not clearly possible to assign them precisely to a specific group. In stable cell lines the expression of the transgenic product gene thus underlies chromosomal positional effects to a considerable extent. This phenomenon is based on the influence of the chromatin structure and/or the presence of intrinsic regulatory elements at the integration site of the foreign DNA. This leads to very variable expression levels. During the selection of cells, therefore, frequently clones with a very low or completely absent product expression are frequently produced. These chromosomal positional effects are also the reason why the generation of stable production cell lines which express a high level of a therapeutic protein is generally a time consuming, high-capacity and expensive process. Stable cell lines with high productivity are usually produced by selection with positive selectable markers, frequently combined with agent-induced gene amplification (e.g. dihydrofolate reductase/methotrexate or glutamine synthetase/methionine-sulfoximine). The pools and clones which are produced with this selection strategy are investigated for high and stable expression in a complex screening process. The majority of the clones produce no or only average amounts of product and only a few are high producers. The proportion of high producers in a mixed population can be increased, for example, by a mutation in the selectable marker (Sautter and Enenkel, 2005, WO 2004/050884). However, it is desirable to further increase the specific productivity of each individual clone as well as the proportion of high producers within a transfected cell population.

The specific productivity of stably transfected cells, particularly CHO- or other production-relevant cells, and the proportion of high producers in a transfection batch should be increased. This should result in the last analysis in a more efficient cell line development. Consequently more and higher producing cell lines could be established in a shorter time and thus save on labour, time and costs.

SUMMARY OF THE INVENTION

The present invention relates to regulatory nucleic acids, particularly a nucleic acid having SEQ ID No. 1, known as a "TE element", or a fragment or derivative thereof, which leads to an increase in the transcription or expression of a gene of interest in stably transfected cells. Surprisingly, it has been shown that the use of a TE element of this kind on an expression vector in conjunction with a promoter, a product gene, a selectable marker and optionally an enhancer in stable integration into a host genome, such as the CHO-DG44 genome, for example, overcomes, shields or cancels out the chromosomal positional effects. As a result, both the proportion of high producers in a transfection batch and also the absolute expression level are increased.

The invention further relates to expression vectors which contain transcription- or expression-increasing regions, fragments or derivatives of SEQ ID No. 1, preferably the TE elements TE-00 (SEQ ID No. 2), TE-01 (SEQ ID No. 3), TE-02 (SEQ ID No. 4), TE-03 (SEQ ID No. 5), TE-04 (SEQ ID No. 6), TE-06 (SEQ ID No. 8), TE-07 (SEQ ID No. 9), TE-08 (SEQ ID No. 10), TE-10 (SEQ ID No. 12), TE-11 (SEQ ID No. 13), TE-12 (SEQ ID No. 14). In view of their small size TE-06, TE-07 and TE-08 re particularly preferred.

SEQ ID No. 1 originates from a sequence region located upstream of the coding region of the ubiquitin/S27a gene, which was isolated from CHO-cells, the gene coding for an essential protein in the ribosome metabolism of the cell.

Compared with the expression vectors used hitherto, the additional introduction of the cis-active TE elements into expression vectors results in a productivity of stably transfected cell pools, particularly CHO-DG44 cell pools, which is up to seven times higher. In transient transfections of CHO-DG44 cell pools, on the other hand, no increase in productivity can be achieved by introducing the TE elements. Thus, the increase in productivity observed in the stable cell pools is not based on an enhancer present in the TE elements. Thus, chromosomal integration is absolutely essential for the increase in productivity caused by TE elements. This is an indication that TE elements may suppress, shield or cancel out negative chromosomal positional effects. As a result, cis-active elements have been produced and identified which are characterised by their particular suitability for selecting and enriching high producing cells and are therefore capable of reducing the expenditure on time, costs and capacity in the isolation and identification of high producing clones.

Possible applications for the invention include the development of high producing cell lines as required for example in the manufacture of biopharmaceuticals, in analytical cell-based assays, in high throughput screenings of substances or in the production of recombinant protein products for NMR spectroscopy, other assays, etc. Because of the higher specific productivity and the reduction of cells which express little or no product, more and higher producing cell lines can be established in a shorter time and thus labour to and costs can be saved. Other possible application are the production of robust improved host cell lines (e.g. the introduction of anti-apoptosis or glycosilation genes), transgenic animals or plants and in gene therapy.

The invention does not arise from the prior art.

The nucleic acid with SEQ ID No. 1 is a nucleic acid sequence isolated from the genome of Chinese hamsters (*Cricetulus griseus*). It comes from a sequence region located upstream of the coding region of the ubiquitin/S27a gene.

The nucleic acid with SEQ ID No. 1 has an average GC content of 44% and does not contain any lengthy passages of GC repeats. This GC content is comparable with the average GC content of about 40% described for genomic DNA of mammals (Delgado et al., 1998).

Parts of the nucleic acid with SEQ ID No. 1 have already been described in WO 97/15664: nucleotides 1579 to 3788 of SEQ ID No. 1 correspond to the nucleotides 1 to 2201 of SEQ ID No. 5 from WO 97/15664, but with a difference. During the production of SEQ ID No. 1 according to the invention, four additional nucleotides were introduced, as a result of the cloning process, formed by a reaction of filling an existing ECORI cutting site. This insertion of the additional four nucleotides took place between nucleotide 357 and 358 of sequence SEQ ID No. 5 from WO 97/15664. Nucleotides 1 to 1578 of the nucleic acid sequence with SEQ ID No. 1 from the present invention, however, constitute new hitherto unknown sequence regions which were isolated within the scope of this invention. Also, WO 97/15664 did not disclose that SEQ ID No. 1 from the present invention or fragments or derivatives thereof increase the transcription or expression of a gene of interest irrespective of the chromosomal integration site when they are functionally linked to a promoter/enhancer combination which allows the transcription of the functionally linked gene of interest. Rather, WO 97/15664 discloses the use of 5'UTR sequences of the ubiquitin/S27a gene as promoter, while the sequence region from position −161 to −45 according to FIG. 5 in WO 97/15664 is essential for promoter activity. This sequence region is only partly present in the nucleic acid of SEQ ID No. 1 according to the invention and a fragment derived therefrom with SEQ ID No. 2 (position −161 to −89 according to FIG. 5 in WO 97/15664). The other fragments and derivatives of SEQ ID No. 1 do not contain this sequence region at all. Moreover, the nucleic acid of SEQ ID No. 1 according to the invention, when using standard alignment algorithms such as BLAST, show no sequence homologies with the nucleic acids sequences described in the following patent applications, which can also positively influence the expression at the chromatin level in cis:
a) UCOE nucleic acid sequences from WO 00/05393
b) EASE nucleic acid sequences from U.S. Pat. No. 6,309,841
c) STAR nucleic acid sequences from WO 03/004704

The vectors shown under A were used to express a recombinant monoclonal IgG1 antibody in CHO-DG44 cells. "E/P" in this case is a combination of CMV enhancer and hamster ubiquitin/S27a promoter, "P" is merely a promoter element and "T" is a termination signal for the transcription which is necessary for the polyadenylation of the transcribed mRNA. The position and direction of transcription initiation within each transcription unit is indicated by an arrow. For cloning TE elements an SpeI cutting site ("SpeI") is present in front of the promoter/enhancer combination. The amplifiable selectable marker dihydrofolate reductase is abbreviated to "DHFR". The selectable marker neomycin phosphotransferase contains the point mutation D227G and is abbreviated to "D227G" accordingly in the Figure. The "IRES" element originating from the encephalomyocarditis virus acts as an internal ribosomal binding site within the bicystronic transcription unit and allows translation of the following green fluorescent protein "GFP". "HC" and "LC" code for the heavy and light chains, respectively, of a humanised monoclonal IgG1 antibody.

The vector shown under B was used to express the recombinant protein MCP1 in CHO-DG44. "E/P" is a combination of CMV enhancer and CMV promoter, "P" is merely a promoter element and "T" is a termination signal for the transcription which is needed for the polyadenylation of the transcribed mRNA. The position and direction of transcription initiation within each transcription unit is indicated by an arrow. For cloning the TE element, a sequence region "A" with cutting sites for restriction endonucleases (adapter) is inserted before the promoter.

The selectable marker neomycin phosphotransferase contains the point mutation F240I and is accordingly abbreviated to F240I in the figure. The IRES element originating from the Encephalomyocarditis virus acts as an internal ribosomal binding site within the bicistronic transcription unit and allows translation of the subsequent red fluorescent protein "dsRed". "MCP-1" codes for human monocyte chemoattractant Protein-1.

Figure 2:
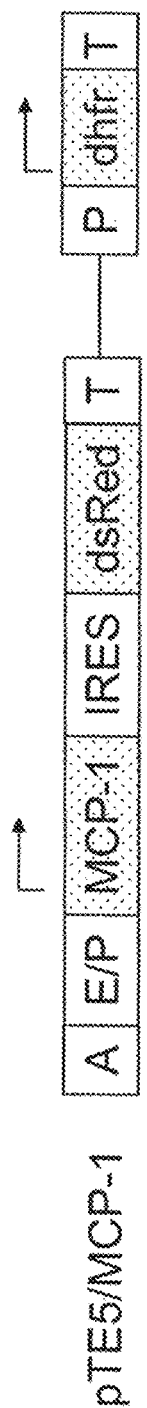

FIG. 2: Schematic Representation of an MCP-1 Base Vector

The vector shown here was used to express the recombinant protein MCP-1 in CHO-DG44 cells. "E/P" is a combination of "E/P" is a combination of CMV enhancer and CMV promoter, "P" is merely a promoter element and "T" is a termination signal for the transcription which is needed for the polyadenylation of the transcribed mRNA. The position and direction of transcription initiation within each transcription unit is indicated by an arrow. For cloning the TE element, a sequence region "A" with cutting sites for restriction endonucleases (adapter) is inserted before the promoter. The selectable marker dihydrofolate reductase is abbreviated to "dhfr" in the figure. The IRES element originating from the Encephalomyocarditis virus acts as an internal ribosomal binding site within the bicistronic transcription unit and allows translation of the subsequent red fluorescent protein "dsRed". "MCP-1" codes for human monocyte chemoattractant Protein-1.

FIG. 3 (shown in figure views 3A-3E): 5' Sequence of the CHO Ubiquitin/S27S Gene The sequence region comprising 3788 bp (SEQ ID No. 1) was isolated from the genome of CHO (Chinese Hamster Ovary) cells and is located upstream of the coding region of the Ub/S27a gene, which is a fusion between a ubiquitin unit (Ub) and a ribosomal protein of the small ribosome subunit (S27a).

Figure 4:
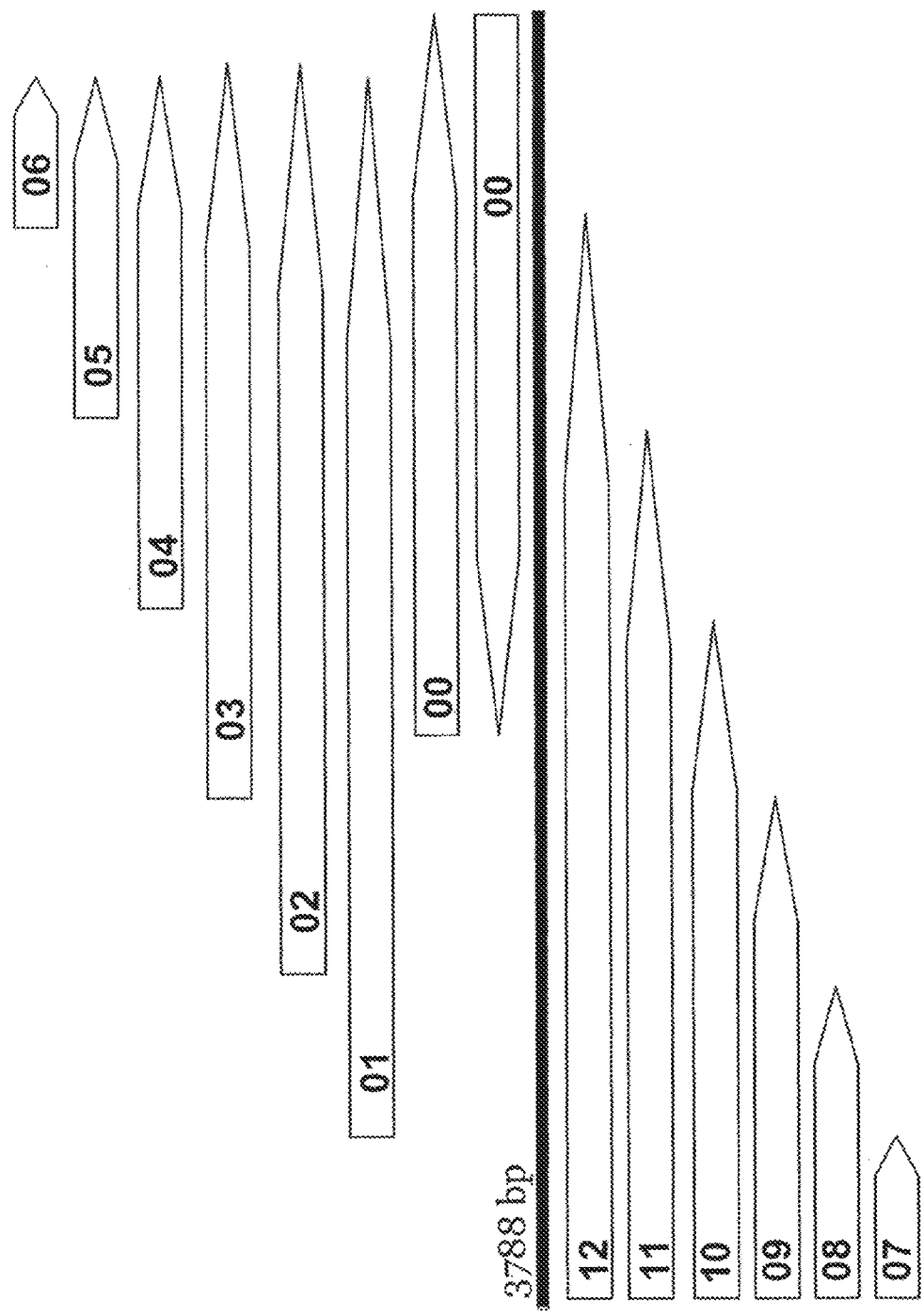

FIG. 4: Graphic Representation of the TE Elements 00 to 12

This figure schematically shows the genomic sequence region of 3788 bp, which was subcloned in a plasmid, located upstream of the coding region of the CHO ubiquitin/S27a gene. From this genome sequence (SEQ ID No. 1) also known as TE element A, partial fragments of different lengths, hereinafter referred to as TE elements, were prepared. TE element 00 (SEQ ID No. 2) was isolated from a subclone of this sequence as a Sac II restriction fragment and cloned into the SpeI cutting site of the target vectors pBID-HC and pBING-LC. These contained either the gene for the heavy chain (HC) or light chain of an IgGl (see FIG. 1A). As a result, expression vectors were formed in which the TE element 00 is positioned in direct and reversed orientation upstream of the promoter. The TE elements 01 to 12 were produced by PCR with various pairs of primers (see FIGS. 5 and 6) and cloned into the base plasmid pTE4/MCP-1 (FIG. 1B) and pTE5/MCP-1 (FIG. 2) via BamHI/BsrGI.

FIG. 5: TE Elements 00 to 12

This Table shows the size and the starting and end positions of the TE elements 00 to 21, which were produced from the TE-A sequence (SEQ ID No. 1). For the fragments produced by PCR, the primers used are additionally specified. The size gradations of the elements are about 500 bp and have deletions at the 5' or 3' end, compared with the starting sequence TE-A (SEQ ID No. 1).

FIG. 6: Primer for Synthesising the TE Elements 01 to 12

The primers are shown in the 5'-3' direction. Primers with "for" in their name are primers in direct orientation of SEQ ID No. 1, primers with "rev" are those in reverse orientation. Each primer consists at the 5' end of six nucleotides followed by a BamHI or BsrGI cutting site and a sequence of about 20 to 30 nucleotides which is 100% homologous with a sequence portion in SEQ ID No. 1. The region of the primer homologous with SEQ ID No. 1 is shown in bold. One for primer and one rev primer was used to amplify a sequence region of SEQ ID No. 1. The resulting PCR product was cloned into the base plasmid pTE4/MCP-1 (FIG. 1B) or pTE5/MCP-1 (FIG. 2) via BamHI and BsrGI.

Figure 7:
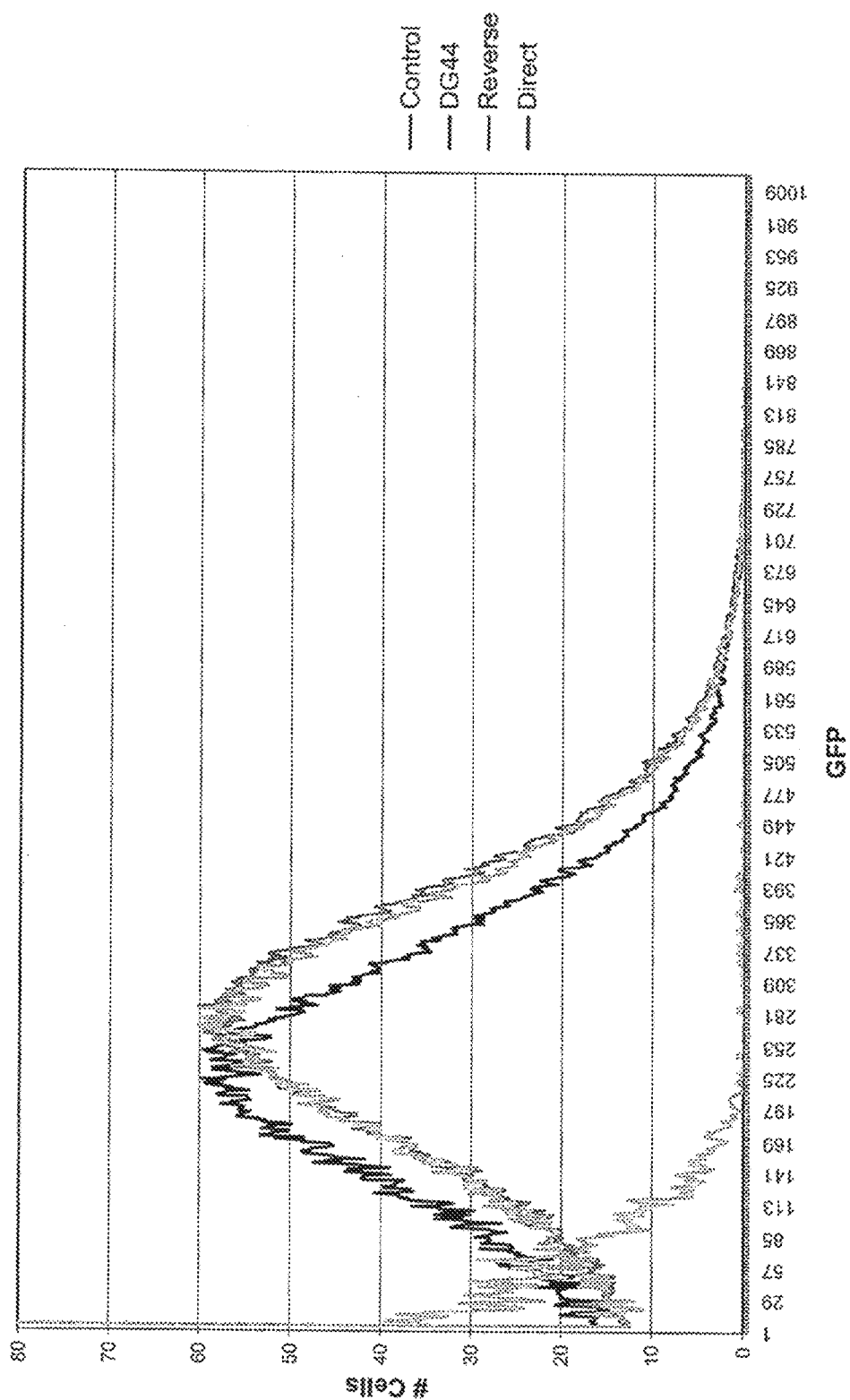

FIG. 7: FACS Measurement of the Tranvection Series B

The Figure shows the relative increase in GFP expression in cells with the TE element 00 compared with cells without the TE element 00. For this, CHO-DG4 cells were transfected with the plasmid combinations pBING-LC and pBID-HC, which differ from one another only in the presence and orientation of the TE element 00. After a two to three-week long selection of the transfected cell pools in HT-free medium with the addition of G418, the GFP fluorescence was measured by FACS analysis. Each graph, with the exception of the untransfected CHO-DG44 cells (DG44) serving as a negative control, constitutes the average of the GFP fluorescence from, in each case, 10 pools of transfection series B. 20000 cells were studied per pool. "Control" denotes the base plasmids pBING-LC and pBID-HC, "reverse" denotes a reverse orientation of the TE element 00 in the base vectors while "direct" indicates a direct orientation of TE element 00 in the base vectors.

Figure 8:
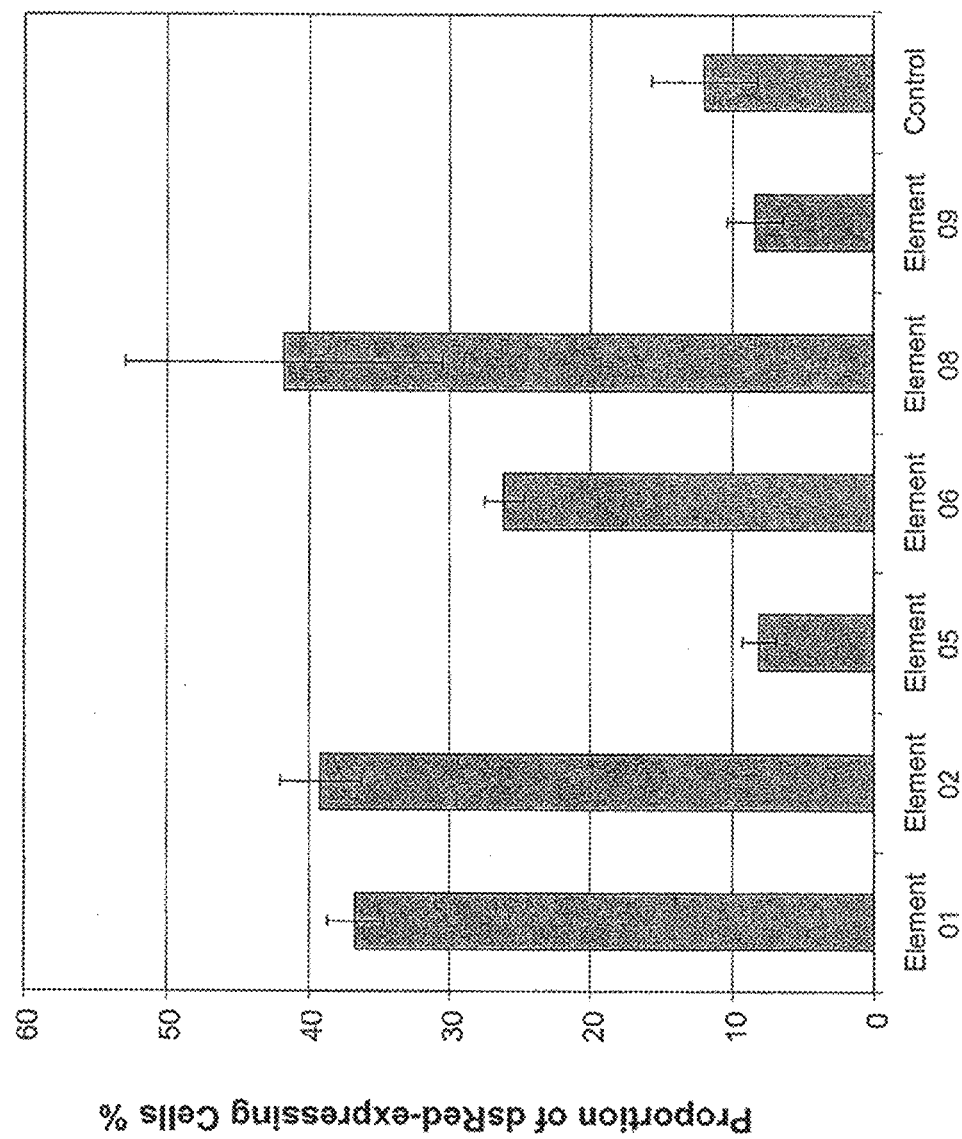

FIG. 8: FACS Measurement of Transvection Series C

The Figure shows the proportion of dsRed2-expressing cells in stable cell populations which contained the TE elements 01, 02, 05, 06, 08 or 09, compared with cells in cell populations which did not contain a TE element. For this, CHO-DG44 cells were transfected with the plasmid pTE4/MCP-1 or derivatives obtained therefrom, which additionally contained one of the TE elements mentioned above. After an approximately three-week long selection of the transfected cell pools in medium with added G418, the dsRed2 fluorescence was measured by FACS analysis. 10000 cells were measured per pool and the inherent fluorescence of the untransfected CHO-DG44 cells was substracted. Each value is the average of the percentage proportion of dsRed2-expressing cells from 6 pools of transfection series C.

Figure 9A:
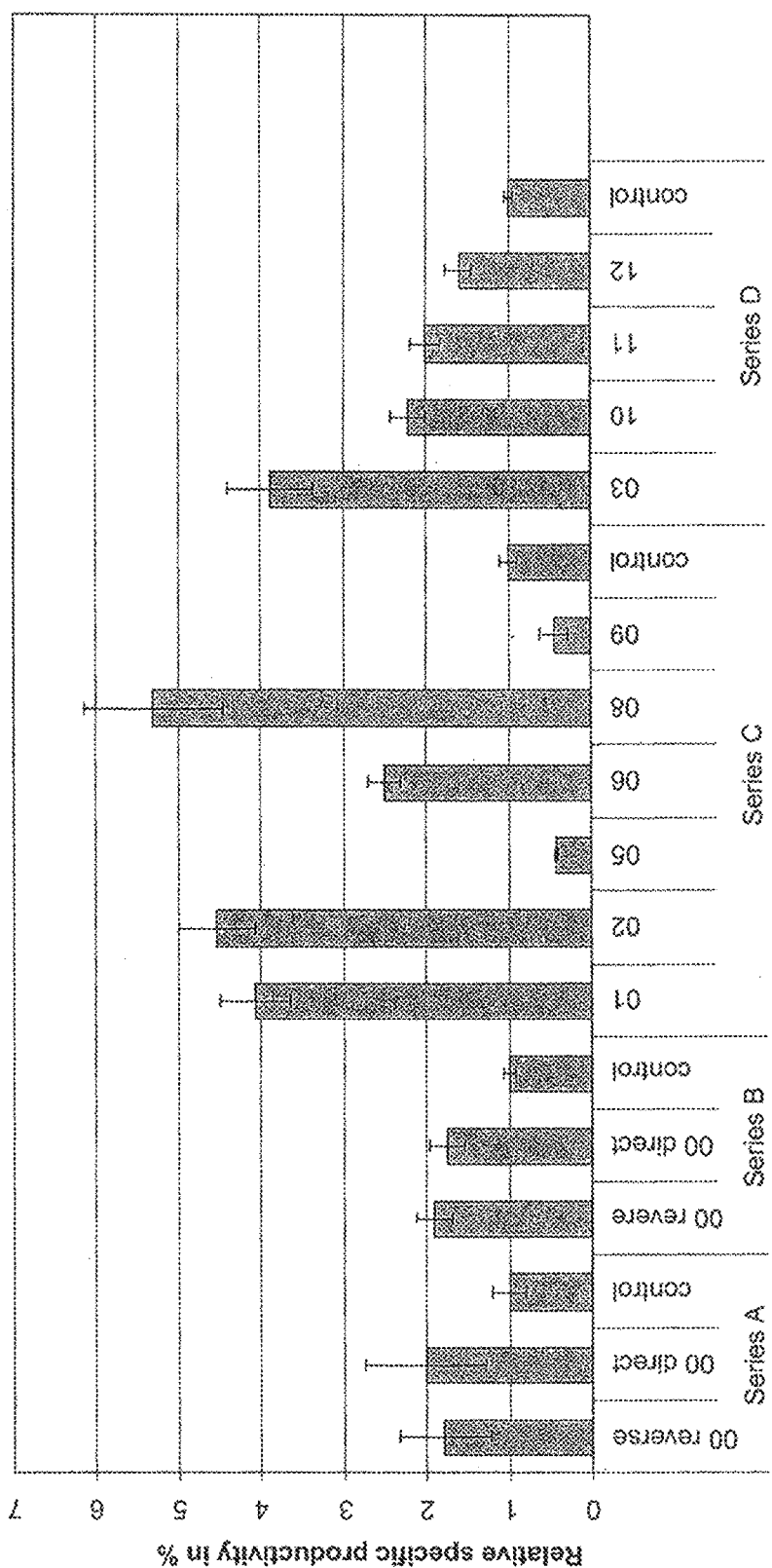

FIG. 9 (shown in figure views 9A-9B): Influence of the TE Elements on the Specific Productivity This Figure shows the changes in the expression level of IgG1 or MCP-1 which are obtained as a result of the presence of the TE elements compared with control pools with no TE element, shown graphically (A) or in table form (B). The cell pools were produced by stable transfection of CHO-DG44 cells with the base plasmids pBING-LC and pBID-HC or pTE4/MCP-1 ("control") and the derivatives obtained therefrom, each of which additionally contained a TE element ("00" in direct orientation ("00 direct") and in reverse orientation ("00 reverse"), "01" to "12"). After a two to three-week long selection of the transfected cell pools in HT-free medium with the addition of G418 (Series A and B) or in HT-containing medium with the addition of G418 (Series C and D) the protein expression was measured by ELISA in the cell culture supernatant and the specific productivity per cell and per day was calculated. The cultivation of the stably transfected CHO-DG44 cells was carried out by several passages in 75 cm$^2$ T flasks with a passaging rhythm of 2-2-3 days. In Series A, 4 pools taken from the plasmid combinations "00 reverse" and "00 direct" were tested and of the control 3 pools were tested over 8 passages in culture, in Series B 10 pools of each plasmid combination were tested by 6 passages and in Series C and D 6 pools of each type of plasmid were tested through 6 passages. The specific productivities of the pools of a plasmid combination and series were averaged and the average of the controls in each series was set at 1. The averaged specific productivities of the pools with TE element were compared with this.

Figure 10A:
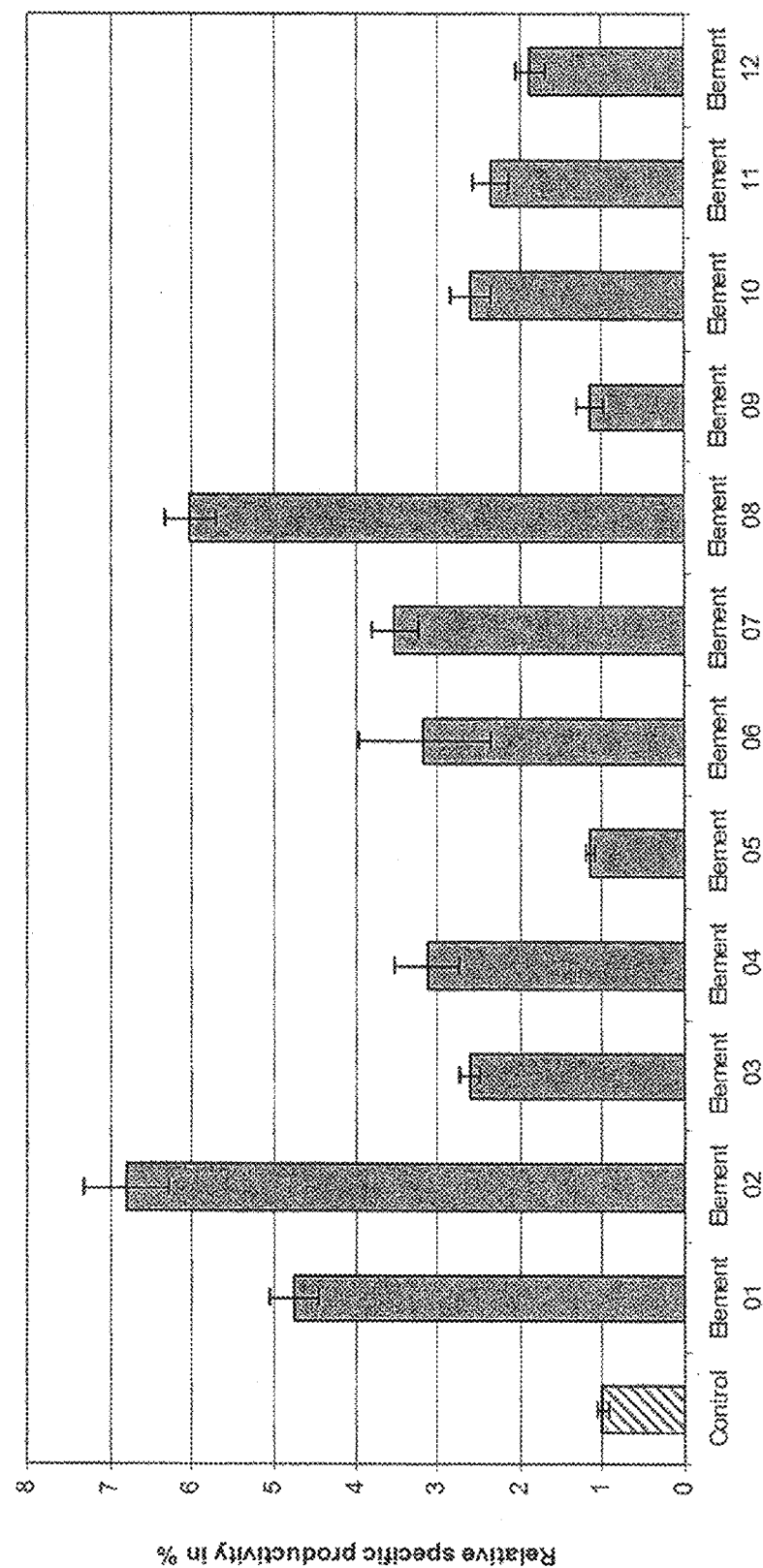

FIG. 10 (show in figure views 10A-10B): Influence of the TE Elements on the Specific Productivity in DHFR-Selected Cell Pools This Figure shows the changes in the expression levels of MCP-1 which resulted from the presence of the TE elements compared with control pools with no TE element, in the form of a graph (A) or table (B). The cell pools were produced by stable transfection of CHO-DG44 cells with the base plasmid pTE5/MCP-1 ("control") or derivatives obtained therefrom, each of which additionally contained a TE element ("01" to "12") (Series E). After a two to three-week long selection of the transfected cell pools in HT-free medium the protein expression was measured by ELISA in the cell culture supernatant and the specific productivity was calculated per cell and per day. The cultivation of the stably transfected CHO-DG44 cells was carried out by several passages in 75 cm$^2$ T flasks with a passaging rhythm of 2-2-3 days. Six pools of each plasmid variant through 6 passages were in cultivation. The specific productivities of the pools of a plasmid variant were averaged and the average of the controls was set at 1. The averaged specific productivities of the pools with a TE element was compared with this.

Figure 11:
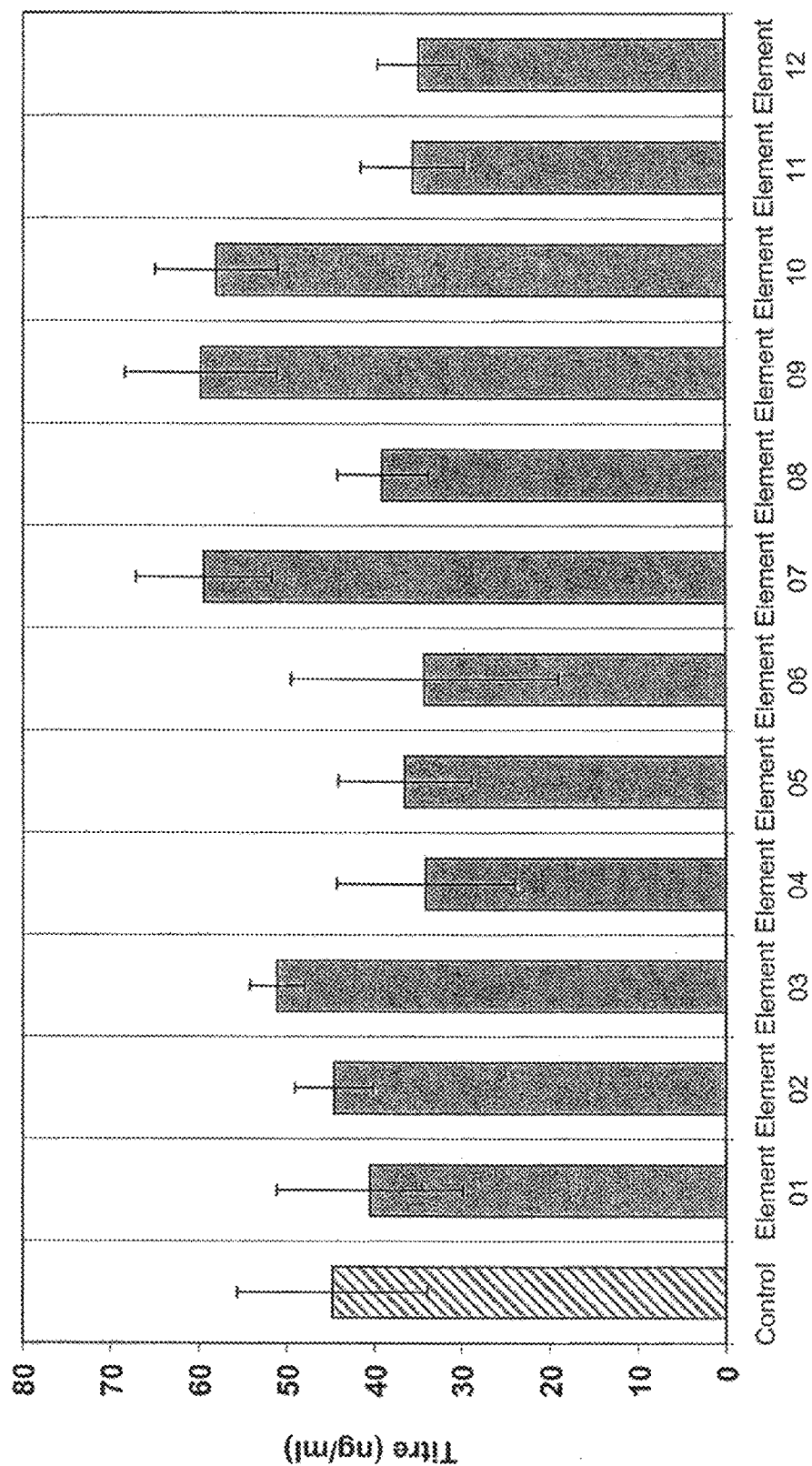

FIG. 11: Testing the TE Elements for Enhancer Activity

The transient transfection of CHO-DG44 cells, when using expression vectors with TE elements, showed no significant increase in the MCP-1 titre compared with control vectors without a TE element. TE elements 01 to 12 thus do not act as enhancers and can therefore only bring about a significant increase in expression when integrated in the chromosomes. Six pools were transfected with pTE4/MCP-1 (control) and the derivatives obtained from it, which additionally each contained aTE element ("01" to "12"). At the same time an SEAP expression plasmid was co-transfected in order to determine the transfection efficiency (SEAP=secreted alkaline phosphatase). After 48 hours cultivation in a total volume of 3 ml, the cell culture supernatant was removed and the MCP-1 titre was determined by ELISA and the SEAP activity was determined. The MCP-1 titre was corrected with regard to the transfection efficiency, determined by SEAP expression. The Figure shows the average of the 6 parallel pools with standard deviation.

Figure 12:
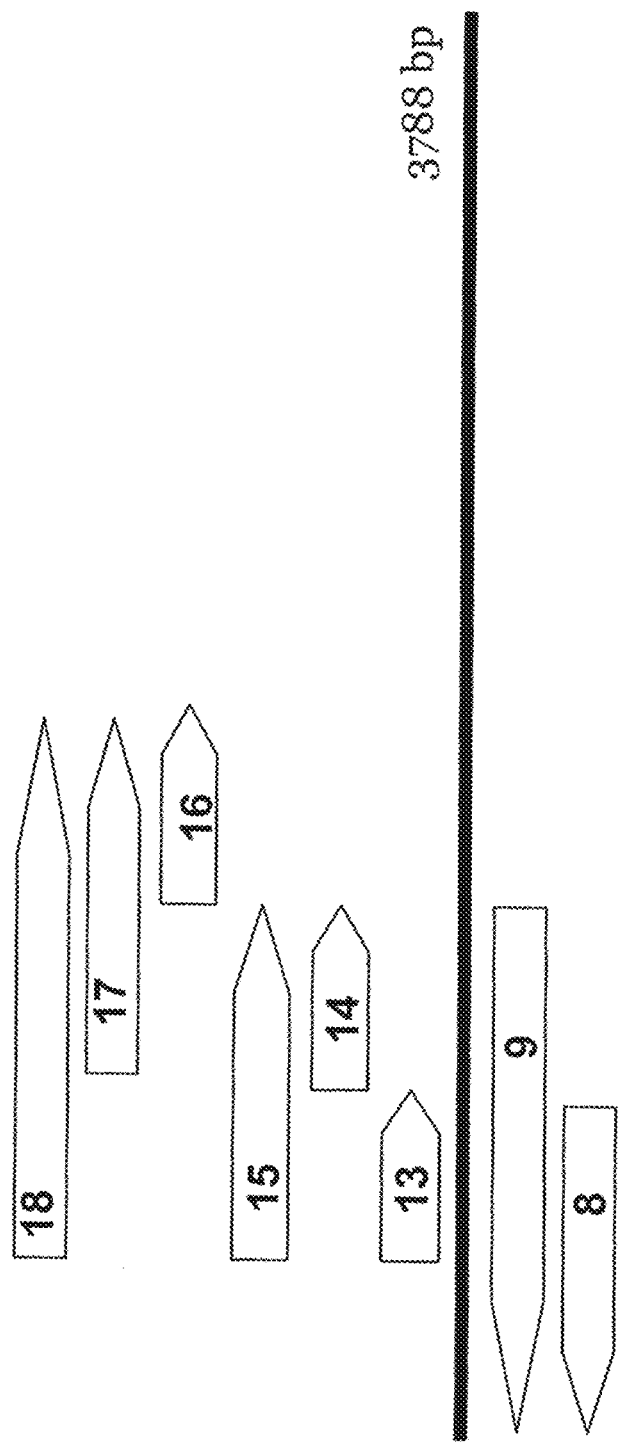

FIG. 12: Other TE Elements

The results thus far indicate that the choice of fragments of Sequence ID No. 1 shown in this Figure could also result in an increase in gene expression. By cloning and stable transfection of these additional TE elements the intention is to characterise Sequence ID No. 1 more clearly in order to locate more precisely the sequence regions which are important for the function.

Figure 13:
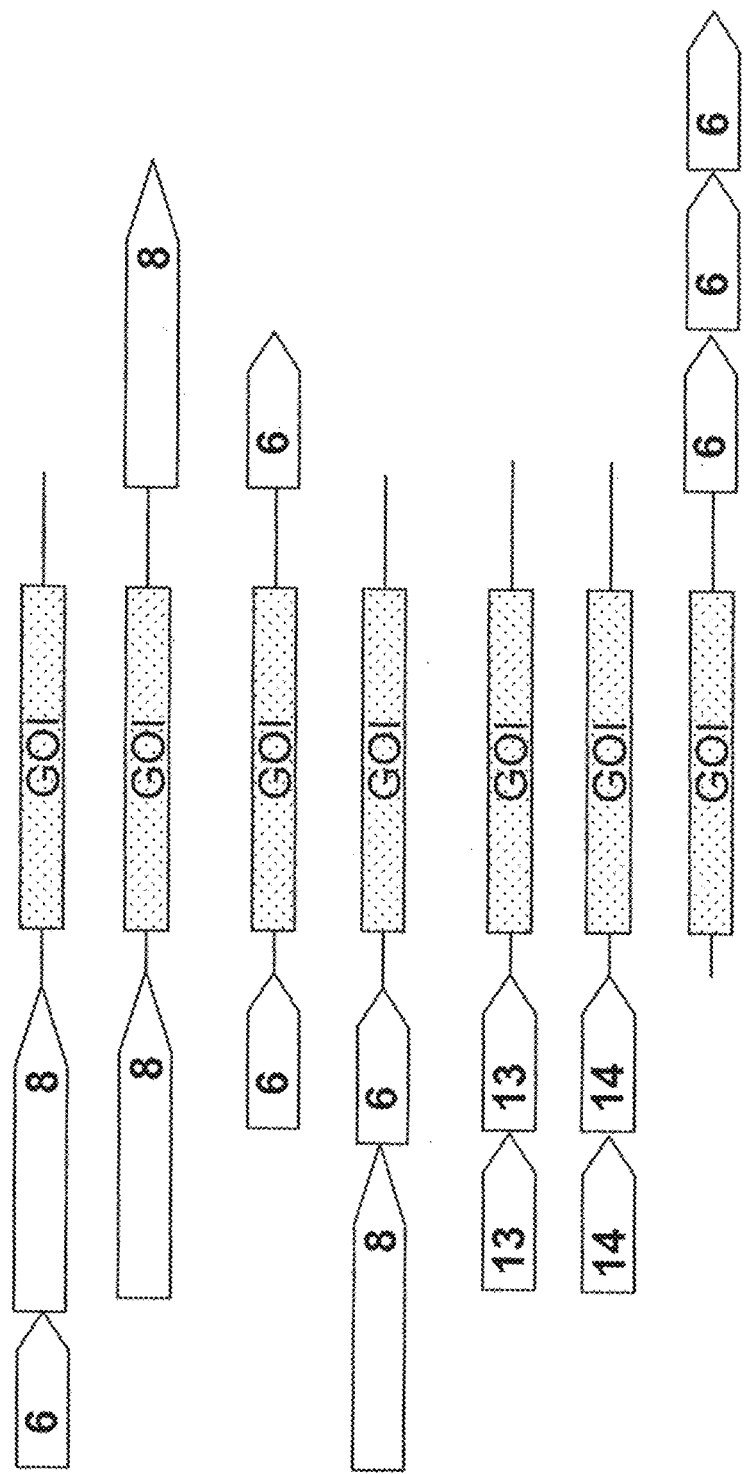

FIG. 13: Testing of Different Positions and Combinations of the TE Elements

This Figure represents a selection of possible expression vectors in which different positions, orientation and combinations of TE elements are used to investigate whether an additional increase in expression can be achieved in this way. As well as the flanking of the product gene by TE elements, a number of identical or different short TE elements are also connected up one behind the other, such as for example TE elements 06 and 08 or the new TE elements 13 and 14.

Figure 14:
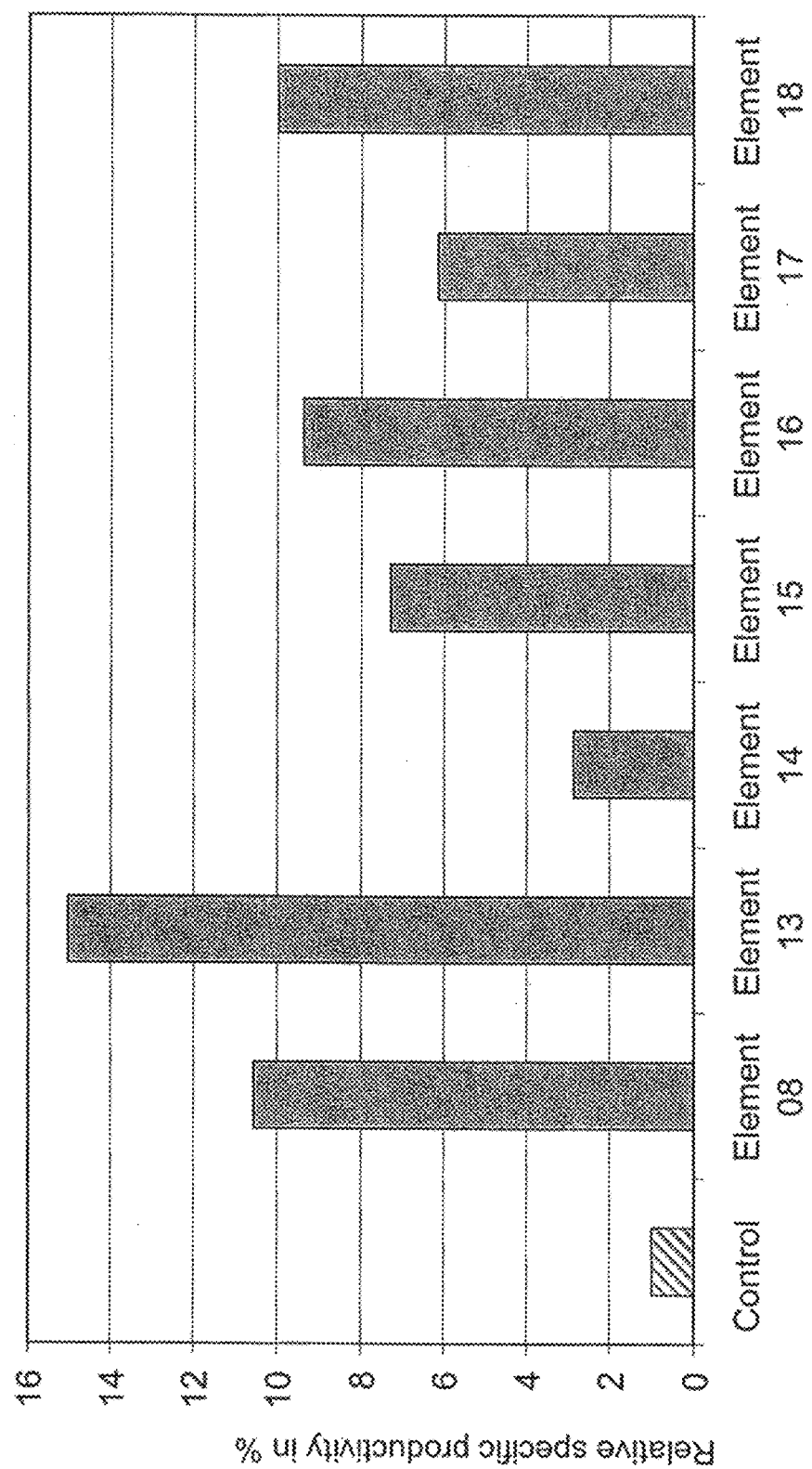

FIG. 14: Influence of TE Elements TE 13 to TE 18 on the Specific MCP-1 Expression This Figure graphically shows the changes in the expression levels of MCP-1 which result from the presence of the TE elements compared with control pools with no TE element. The cell pools are produced by stable transfection of CHO-DG44 cells with the base plasmid pTE4/MCP-1 ("control") or derivatives obtained therefrom which additional each contained a TE element ("13" to "18") (Series F). After a two to three-week long selection of the transfected cell pools in HT-supplemented medium +G418 (400 µg/ml) the protein expression was measured by ELISA in the cell culture supernatant and the specific productivity per cell and per day was calculated. Cultivation of the stably transfected CHO-DG44 cells was carried out by several passages in 75 cm$^2$ T flasks with a passaging rhythm of 2-2-3 days. Of each plasmid variant, 4 pools were in cultivation over 5 to 6 passages. The specific productivities of the pools of a plasmid variant were averaged and the average of the controls was set at 1. The averaged specific productivities of the pools with a TE element were compared with this.

Figure 15:
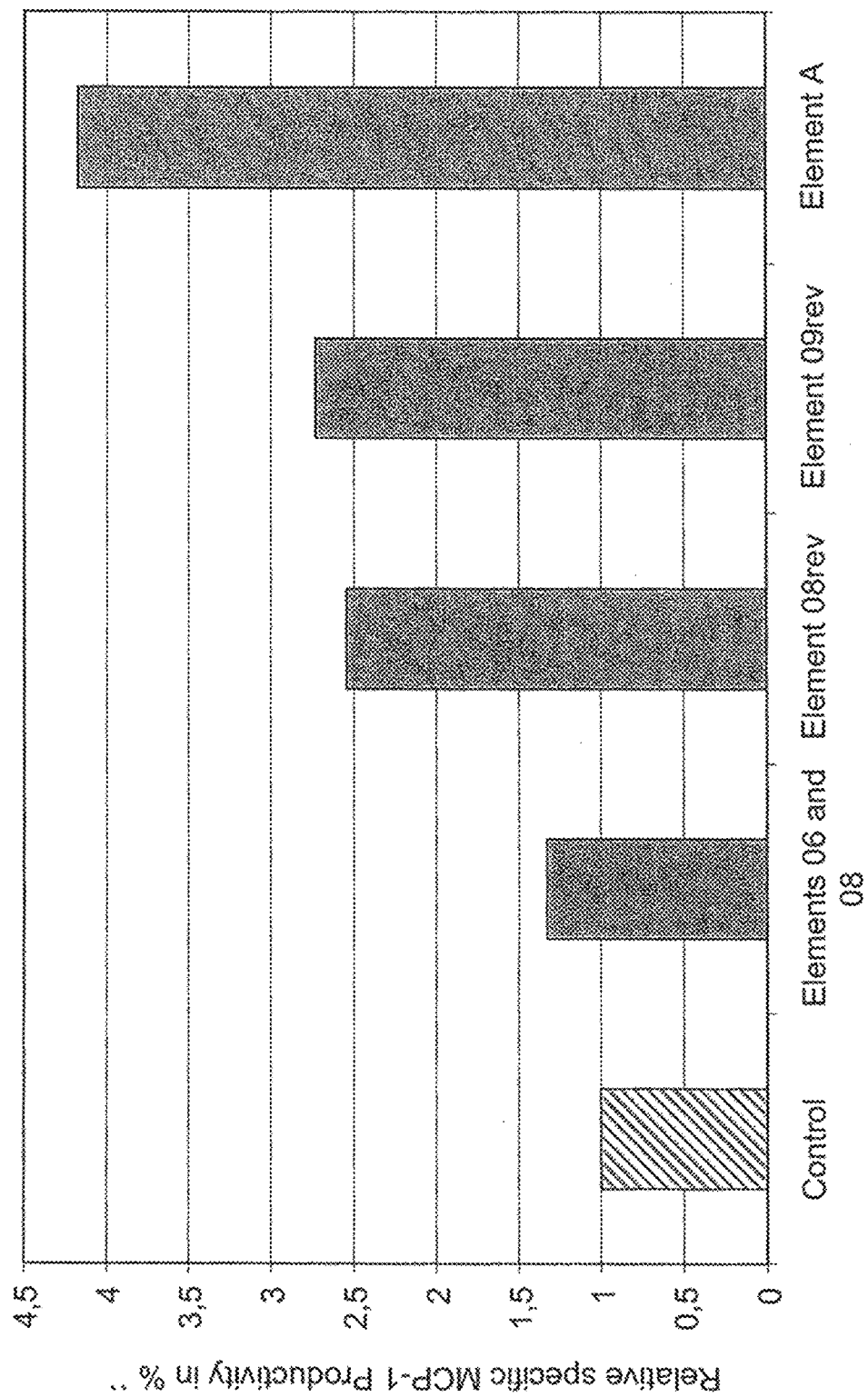

FIG. 15: Influence of the TE Elements at Various Positions and in Various Combinations on the Expression of MCP-1

This Figure graphically shows the changes in the expression levels of MCP-1 which result from the presence and combination of different TE elements compared with control pools without a TE element. The cell pools were produced by stable transfection CHO-DG44 cells with the base plasmid pTE4/MCP-1 ("control") or derivatives obtained therefrom which additionally each contained one or two TE elements ("06 and 08, 08rev, 09rev, A") (Series G). After two to three-week long selection of the transfected cell pools in HT-supplemented medium +G418 (300 µg/ml) the protein expression was measured by ELISA in the cell culture supernatant and the specific productivity per cell and per day was calculated. The cultivation of the stably transfected CHO-DG44 cells was carried out by several passages in 6-well plates (MAT6) with a passaging rhythm of 2-2-3 days. Of each plasmid variant, 6 pools were in cultivation over 6 passages. The specific productivities of the pools of a plasmid variant were averaged and the average value of the controls was set at 1. The averaged specific productivities of the pools with a TE element were compared with this.

Figure 16:
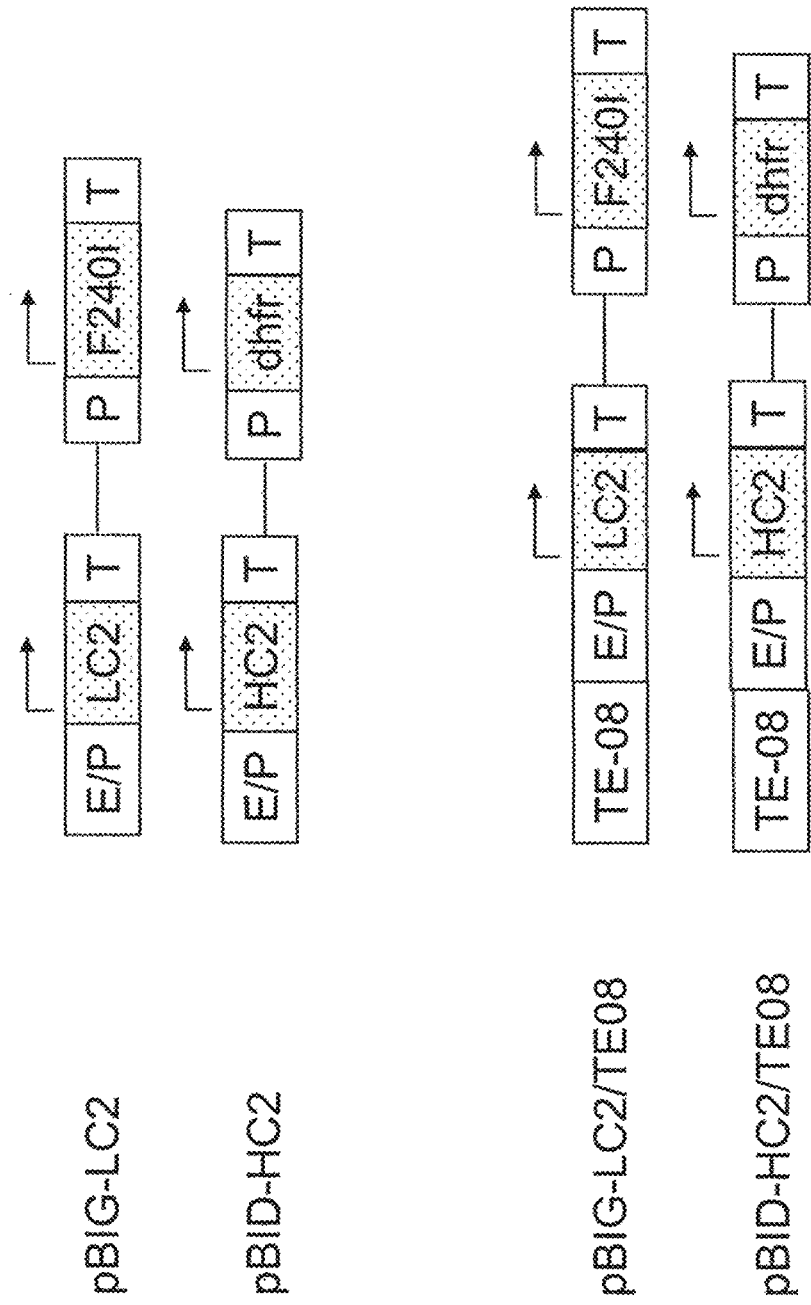

FIG. 16: Testing of the TE Element TE-08 with IGG-4 Antibodies

Figure 1:
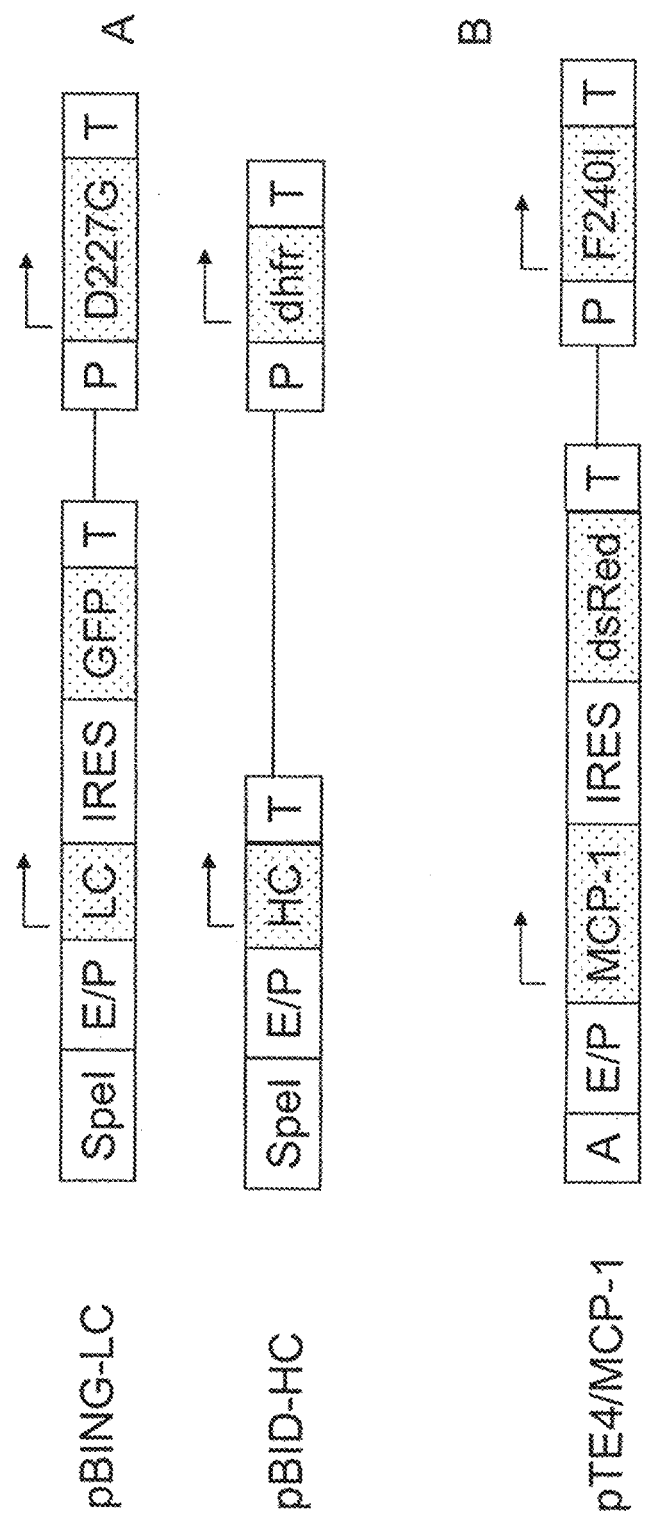
FIG. 1: Schematic Representation of the Base Vectors

The vectors shown here were used for the expression of recombinant monoclonal IgG4 antibodies in CHO-DG44 cells. E/P in this case is a combination of CMV enhancer and promoter, P is merely a promoter element and T is a termination signal for the transcription, which is required for the polyadenylation of the transcribed mRNA. The position and direction of the transcription initiation within each transcription unit is indicated by an arrow. The genes for the light chain (LC) and heavy chain (HC) were cloned in, in exchange for the MCP-1-IRES-dsRed2 cassette (FIGS. 1B and 2). The code for the heavy and light chains, respectively, of a humanise monoclonal IgG-4 antibody. The amplifiable selectable marker dihydrofolate reductase is abbreviated to "dhfr". The selectable marker neomycin-phosphotransferase contains the point mutation F240I and is abbreviated accordingly to F240I in the Figure.

DETAILED DESCRIPTION OF THE INVENTION

Terms and designations used within the scope of this description of the invention have the following meanings defined hereinafter. The general terms "containing" or "contains" includes the more specific term "consisting of". Moreover, the terms "single number" and "plurality" are not used restrictively.

The term "TE element" denotes regulatory nucleic acids.

The terms "TE element" or "expression-enhancing element" or "transcription enhancing element" or "expression or transcription enhancing nucleic acid element" are used synonymously in the test. These terms all refer to regulatory nucleic acid sequences.

By "TE element" or "expression enhancing element" or "transcription enhancing element" or "expression or transcription enhancing nucleic acid element" is meant in particular Sequence ID No. 1, including the complementary sequence thereto, which was isolated from the genome of the Chinese hamster (Cricetulus griseus), or any part, fragment or region thereof or a derivative of Sequence ID No. 1 or one of the parts, fragments or regions thereof, which when stably integrated in the chromosomes leads to an increase in the transcription or expression of a gene of interest. Also meant are any desired combinations of parts, fragments, regions or derivatives of Sequence ID No. 1 which consist of a number of identical or different parts, fragments, regions or derivatives of SEQ ID No. 1, which may in turn be arranged in any desired orientation and at any desired spacing relative to one another or may be combined with other regulatory sequences and which lead to an increase in the transcription or expression of a gene of interest. The term TE element may refer both to SEQ ID No. 1 itself and to any desired fragments, parts, regions or derivatives thereof.

Furthermore, the term "TE element", "transcription enhancing or expression enhancing nucleic acid element" or fragments, parts, regions or derivatives thereof encompasses, in addition to parts of the sequence of the Chinese hamster (Cricetulus griseus), corresponding functional homologous nucleotide sequences from other organisms.

Examples of these other organisms include man, mouse, rat, monkey and other mammals and rodents, reptiles, birds, fishes and plants.

By a "fragment" or "part" or "region" (these terms being used synonymously) is meant a nucleic acid molecule (single or double stranded) which is 100% identical in its sequence to a part of SEQ ID No. 1 or the complementary sequence thereto. It is known that the cloning of fragments which are produced either by digestion with restriction enzymes or by PCR can lead to modifications in the end regions of the fragment, i.e. additional or absent nucleotides or nucleotides additionally introduced through primers, which are the result of filling or breakdown reactions. These variations in the end regions of the fragments are included in the definition of a fragment, even if these sequence regions have a sequence identity of less than 100% with SEQ ID No. 1. "Parts" or "fragments" or "regions" of Sequence ID No. 1 include for example TE-00 (Sequence ID No. 2), TE-01 (Sequence ID No. 3), TE-02 (Sequence ID No. 4), TE-03 (Sequence ID No. 5), TE-04 (Sequence ID No. 6), TE-05 (Sequence ID No. 7), TE-06 (Sequence ID No. 8), TE-07 (Sequence ID No. 9), TE-08 (Sequence ID No. 10), TE-09 (Sequence ID No. 11), TE-10 (Sequence ID No. 12), TE-11 (Sequence ID No. 13), TE-12 (Sequence ID No. 14), TE-13 (Sequence ID No. 15), TE-14 (Sequence ID No. 16), TE-15 (Sequence ID No. 17), TE-16 (Sequence ID No. 18), TE-17 (Sequence ID No. 19), TE-18 (Sequence ID No. 20). Preferably, with stable chromosomal integration, the fragment leads to an increase in the transcription or expression of a functionally linked gene of interest. "Parts" or "fragments" or "regions" of Sequence ID No. 1, which lead to an increase in the transcription or expression of a gene of interest, are for example TE-00 (Sequence ID No. 2), TE-01 (Sequence ID No. 3), TE-02 (Sequence ID No. 4), TE-03 (Sequence ID No. 5), TE-04 (Sequence ID No. 6), TE-06 (Sequence ID No. 8), TE-07 (Sequence ID No. 9), TE-08 (Sequence ID No. 10), TE-10 (Sequence ID No. 12), TE-11 (Sequence ID No. 13), TE-12 (Sequence ID No. 14). However, the term "fragment" also includes all possible other parts of SEQ ID No. 1 in any desired orientation which lead to an increase in the transcription or expression of a gene of interest, particularly those which are wholly or at least partially in the 5' region of TE-00 (SEQ ID No. 2). This corresponds to the partial region of SEQ ID No. 1 between 1 bp and 1578 bp. Also preferred is the fragment TE-08 (SEQ ID No. 10).

By a "derivative" is meant, in the present invention, a nucleic acid molecule (single or double stranded) which has at least 70% sequence identity, preferably at least about 80% sequence identity, particularly preferably at least about 90% sequence identity and most preferably at least about 95% sequence identity with SEQ ID No. 1 or the complementary sequence thereto or with a part or fragment or region of SEQ ID No. 1 or the complementary sequence thereto, and which, on chromosomal integration, leads to an increase in the transcription or expression of a gene of interest. Sequence differences from SEQ ID No. 1 may be based on the one hand on differences in homologous endogenous nucleotide sequences from other organisms. On the other hand they may also be based on deliberate modifications of the nucleotide acid sequence, e.g. on substitution, insertion or deletion of at least one or more nucleotides. Deletion, insertion and substitution mutants can be produced by "site-specific mutagenesis" and/or "PCR-based mutagenesis techniques". Corresponding methods are described by way of example by Lottspeich and Zorbas (1998; Chapter 36.1 with further references). The sequence identity can be brought into conformity with a reference sequence, in this case Sequence ID No. 1, using so-called standard alignment algorithms such as for example "BLAST" (Altschul, S. F., Gish, W., Miller, W., Myers, E. W. & Lipman, D. J. (1990) "Basic local alignment search tool." J. Mol. Biol. 215:403-410; Madden, T. L., Tatusov, R. L. & Zhang, J. (1996) "Applications of network BLAST server" Meth. Enzymol. 266: 131-141; Zhang, J. & Madden, T. L. (1997) "PowerBLAST: A new network BLAST application for interactive or automated sequence analysis and annotation." Genome Res. 7:649-656). Sequences are brought into conformity when they correspond in their succession and can be identified using standard alignment algorithms By a "derivative" is meant, according to the present invention, a nucleic acid molecule (single or double stranded) which hybridises with SEQ ID No. 1 or with the sequence of a fragment or part or region of SEQ ID No. 1 or of a sequence complementary thereto. Preferably the hybridisation is carried out under stringent hybridisation and washing conditions (e.g. hybridisation at 65° C. in a buffer containing 5×SSC; washing at 42° C. with 0.2×SSC/0.1% SDS). Corresponding techniques are described by way of example in Ausubel et al., 1994. Preferably the part or fragment or region of SEQ ID No. 1 includes all or at least parts of the sequence region between nucleotide position 1 bp and 1578 bp. This corresponds to sequence region 5' of the TE-00 sequence (SEQ ID No. 2). The fragment TE-08 (SEQ ID No. 10) is also preferred.

The term "variant" refers to the expression vectors used in the particular transfection mixture. These include both the base vectors (pTE4/MCP-1 or pTE5/MCP-1) or the base vector combination (pBING-LC+pBID-HC) and also the base vectors which contain one or more TE elements in different positions, combinations and orientations.

In the case of primers, the term "orientation" refers to the arrangement of the primers in relation to SEQ ID No. 1. All the primers whose sequence order corresponds to the sequence in the 5'-3' order shown under SEQ ID No. 1 (=forward primer) are in the same orientation as this sequence, which is also referred to as "direct orientation". Primers whose sequence order is complementary to the sequence given under SEQ ID No. 1 (=reverse primer) are in the opposite orientation to this sequence, which is also referred to as "reverse orientation". In connection with TE elements, in the present invention, the term "orientation" refers to the arrangement in relation to the gene of interest. The sequence given under SEQ ID No. 1 represents a genome sequence which is positioned 5' from the region coding for the ubiquitin/S27a gene, which is also referred to as "upstream".

The continuation of this sequence shown in SEQ ID No. 1 in the direction of the coding region of the following ubiquitin/S27a gene would lead to the start codon of this gene. This arrangement is therefore referred to as "direct orientation". Analogously, in the present invention, the TE element is in the direct orientation when the sequence shown in SEQ ID No. 1, or any desired part, fragment, region or derivative thereof, is present in the expression vector on the same DNA strand as the start codon of the gene of interest. If, by contrast, the sequence complementary to SEQ ID No. 1, or any desired part, fragment, region or derivative thereof, is present in the expression vector on the same DNA strand as the start codon of the gene of interest, then the TE element is in a "reverse orientation".

Unless stated otherwise, when a TE element is mentioned, both orientations are always included/meant, i.e. both direct and reverse.

By "chromosomal integration" is meant the integration of any desired nucleic acid sequence into the genome, i.e. into the chromosomes, of a cell, this integration optionally being into one or more chromosomes in any desired number, position and orientation. Moreover, the term "chromosomal integration" also includes the integration of any desired nucleic acid sequence into synthetic, artificial or minichromosomes.

Gene of Interest:

The gene of interest contained in the expression vector according to the invention comprises a nucleotide sequence of any length which codes for a product of interest. The gene product or "product of interest" is generally a protein, polypeptide, peptide or fragment or derivative thereof. However, it may also be RNA or antisense RNA. The gene of interest may be present in its full length, in shortened form, as a fusion gene or as a labelled gene. It may be genomic DNA or preferably cDNA or corresponding fragments or fusions. The gene of interest may be the native gene sequence, or it may be mutated or otherwise modified. Such modifications include codon optimisations for adapting to a particular host cell and humanisation. The gene of interest may, for example, code for a secreted, cytoplasmic, nuclear-located, membrane-bound or cell surface-bound polypeptide.

The term "nucleotide sequence", "nucleotide sequence" or "nucleic acid sequence" indicates an oligonucleotide, nucleotides, polynucleotides and fragments thereof as well as DNA or RNA of genomic or synthetic origin which occur as single or double strands and can represent the coding or non-coding strand of a gene. Nucleic acid sequences may be modified using standard techniques such as site-specific mutagenesis or PCR-mediated mutagenesis (e.g. described in Sambrook et al., 1989 or Ausubel et al., 1994).

By "coding" is meant the property or capacity of a specific sequence of nucleotides in a nucleic acid, for example a gene in a chromosome or an mRNA, to act as a matrix for the synthesis of other polymers and macromolecules such as for example rRNA, tRNA, mRNA, other RNA molecules, cDNA or polypeptides in a biological process. Accordingly, a gene codes for a protein if the desired protein is produced in a cell or another biological system by transcription and subsequent translation of the mRNA. Both the coding strand whose nucleotide sequence is identical to the mRNA sequence and is normally also given in sequence databanks, e.g. EMBL or GenBank, and also the non-coding strand of a gene or cDNA which acts as the matrix for transcription may be referred to as coding for a product or protein. A nucleic acid which codes for a protein also includes nucleic acids which have a different order of nucleotide sequence on the basis of the degenerate genetic code but result in the same amino acid sequence of the protein. Nucleic acid sequences which code for proteins may also contain introns.

The term "cDNA" denotes deoxyribonucleic acids which are prepared by reverse transcription and synthesis of the second DNA strand from a mRNA or other RNA produced from a gene. If the cDNA is present as a double stranded DNA molecule it contains both a coding and a non-coding strand.

The term "intron" denotes non-coding nucleotide sequences of any length. They occur naturally in numerous eukaryotic genes and are eliminated from a previously transcribed mRNA precursor by a process known as splicing. This requires precise excision of the intron at the 5' and 3' ends and correct joining of the resulting mRNA ends so as to produce a mature processed mRNA with the correct reading frame for successful protein synthesis. Many of the splice donor and splice acceptor sites involved in this splicing process, i.e. the sequences located directly at the exon-intron or intron-exon interfaces, have been characterised by now. For an overview see Ohshima et al., 1987.

Protein/Product of Interest

Proteins/polypeptides with a biopharmaceutical significance include for example antibodies, enzymes, cytokines, lymphokines, adhesion molecules, receptors and the derivatives or fragments thereof, but are not restricted thereto. Generally, all polypeptides which act as agonists or antagonists and/or have therapeutic or diagnostic applications may be used. Other proteins of interest are, for example, proteins/polypeptides, which are used to change the properties of host cells within the scope of so-called "Cell Engineering", such as e.g. anti-apoptotic proteins, chaperones, metabolic enzymes, glycosylation enzymes and the derivatives or fragments thereof, but are not restricted thereto.

The term "polypeptides" is used for amino acid sequences or proteins and refers to polymers of amino acids of any length. This term also includes proteins which have been modified post-translationally by reactions such as glycosylation, phosphorylation, acetylation or protein processing. The structure of the polypeptide may be modified, for example, by substitutions, deletions or insertions of amino acids and fusion with other proteins while retaining its biological activity. In addition, the polypeptides may multimerise and form homo- and heteromers.

Examples of therapeutic proteins are insulin, insulin-like growth factor, human growth hormone (hGH) and other growth factors, receptors, tissue plasminogen activator (tPA), erythropoietin (EPO), cytokines, e.g. interleukines (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN)-alpha, -beta, -gamma, -omega or -tau, tumour necrosis factor (TNF) such as TNF-alpha, beta or gamma, TRAIL, G-CSF, GM-CSF, M-CSF, MCP-1 and VEGF. Other examples are monoclonal, polyclonal, multispecific and single chain antibodies and fragments thereof such as for example Fab, Fab', F(ab')$_2$, Fc and Fc' fragments, light (L) and heavy (H) immunoglobulin chains and the constant, variable or hypervariable regions thereof as well as Fv and Fd fragments (Chamov et al., 1999). The antibodies may be of human or non-human origin. Humanised and chimeric antibodies are also possible.

Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')$_2$ fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable=fragment of the variable part). As covalent binding via the cysteine groups of the constant chains is not possible in these Fv fragments, they are often stabilised by some other method. For this purpose the variable regions of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known and described, cf. for example Huston et al., 1988.

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the Leucine Zipper domains. In other strategies the interactions between the VH and VL regions of the scFv fragment are used for multimerisation (e.g. dia, tri- and pentabodies).

The term "diabody" is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted disulphite bridges. Examples of diabodies can be found in the literature, e.g. in Perisic et al., 1994.

The term "minibody" is used in the art to denote a bivalent homodimeric scFv derivative. It consists of a fusion protein which contains the CH3 region of an immunoglobulin, preferably IgG, most preferably IgG1, as dimerisation region. This connects the scFv fragments by means of a hinge region, also of IgG, and a linker region. Examples of such minibodies are described by Hu et al., 1996.

The term "triabody" is used in the art to denote a trivalent homotrimeric scFv derivative (Kortt et al., 1997). The direct fusion of VH-VL without the use of a linker sequence leads to the formation of trimers.

The fragments known in the art as mini antibodies which have a bi, tri- or tetravalent structure are also derivatives of scFv fragments. The multimerisation is achieved by means of di-, tri- or tetrameric coiled coil structures (Pack et al., 1993 and 1995; Lovejoy et al., 1993).

Gene Which Codes for a Fluorescent Protein:

In another embodiment the expression vector according to the invention contains a gene coding for a fluorescent protein, functionally linked to the gene of interest. Preferably, both genes are transcribed under the control of a single heterologous promoter so that the protein/product of interest and the fluorescent protein are coded by a bicistronic mRNA. This makes it possible to identify cells which produce the protein/product of interest in large amounts, by means of the expression rate of the fluorescent protein. Alternatively, the transcription of the gene coding for the fluorescent protein may take place under the control of its own promoter.

The fluorescent protein may be, for example, a green, bluish-green, blue, yellow or other coloured fluorescent protein. One particular example is green fluorescent protein (GFP) obtained from *Aequorea victoria* or *Renilla reniformis* and mutants developed from them; cf. for example Bennet et al., 1998; Chalfie et al., 1994; WO 01/04306 and the literature cited therein.

Other fluorescent proteins and genes coding for them are described in WO 00/34318, WO 00/34326, WO 00/34526 and WO 01/27150 which are incorporated herein by reference. These fluorescent proteins are fluorophores of non-bioluminescent organisms of the species *Anthozoa*, for example *Anemonia majano, Clavularia* sp., *Zoanthus* sp. I, *Zoanthus* sp. II, *Discosoma striata, Discosoma* sp. "red", *Discosoma* sp. "green", *Discosoma* sp. "Magenta", *Anemonia sulcata, Aequorea coerulescens*.

The fluorescent proteins used according to the invention contain in addition to the wild-type proteins natural or genetically engineered mutants and variants, fragments, derivatives or variants thereof which have for example been fused with other proteins or peptides. The mutations used may for example alter the excitation or emission spectrum, the formation of chromophores, the extinction coefficient or the stability of the protein. Moreover, the to expression in mammalian cells or other species can be improved by codon optimisation. According to the invention the fluorescent protein may also be used in fusion with a selectable marker, preferably an amplifiable selectable marker such as dihydrofolate reductase (DHFR).

The fluorescence emitted by the fluorescent proteins makes it possible to detect the proteins, e.g. by throughflow cytometry with a fluorescence-activated cell sorter (FACS) or by fluorescence microscopy.

Other Regulatory Elements:

The expression vector contains at least one heterologous promoter which allows expression of the gene of interest and preferably also of the fluorescent protein.

The term "promoter" denotes a polynucleotide sequence which allows and controls the transcription of the genes or sequences functionally connected therewith. A promoter contains recognition sequences for binding RNA polymerase and the initiation site for transcription (transcription initiation site). In order to express a desired sequence in a certain cell type or a host cell a suitable functional promoter must be chosen. The skilled man will be familiar with a variety of promoters from various sources, including constitutive, inducible and repressible promoters. They are deposited in databanks such as GenBank, for example, and may be obtained as separate elements or elements cloned within polynucleotide sequences from commercial or individual sources. In inducible promoters the activity of the promoter may be reduced or increased in response to a signal. One example of an inducible promoter is the tetracycline (tet) promoter. This contains tetracycline operator sequences (tetO) which can be induced by a tetracycline-regulated transactivator protein (tTA). In the presence of tetracycline the binding of tTA to tetO is inhibited. Examples of other inducible promoters are the jun, fos, metallothionein and heat shock promoter (see also Sambrook et al., 1989; Gossen et al., 1994).

Of the promoters which are particularly suitable for high expression in eukaryotes, there are for example the ubiquitin/S27a promoter of the hamster (WO 97/15664), SV 40 early promoter, adenovirus major late promoter, mouse metallothionein-I promoter, the long terminal repeat region of Rous Sarcoma Virus, the early promoter of human Cytomegalovirus. Examples of other heterologous mammalian promoters are the actin, immunoglobulin or heat shock promoter(s).

A corresponding heterologous promoter can be functionally connected to other regulatory sequences in order to increase/regulate the transcription activity in an expression cassette.

For example, the promoter may be functionally linked to enhancer sequences in order to increase the transcriptional activity. For this, one or more enhancers and/or several copies of an enhancer sequence may be used, e.g. a CMV or SV40 enhancer. Accordingly, an expression vector according to the invention, in another embodiment, contains one or more enhancers/enhancer sequences, preferably a CMV or SV40 enhancer.

The term enhancer denotes a polynucleotide sequence which in the cis location acts on the activity of a promoter and thus stimulates the transcription of a gene functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled man will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

Another possible modification is, for example, the introduction of multiple Sp1 binding sites. The promoter sequences may also be combined with regulatory sequences which allow control/regulation of the transcription activity. Thus, the promoter can be made repressible/inducible. This can be done for example by linking to sequences which are binding sites for up- or down-regulating transcription factors. The above mentioned transcription factor Sp1, for example, has a positive effect on the transcription activity. Another example is the binding site for the activator protein AP1, which may act both positively and negatively on transcription. The activity of AP1 can be controlled by all kinds of factors such as, for example, growth factors, cytokines and serum (Faisst et al., 1992 and references therein). The transcription efficiency can also be increased by changing the promoter sequence by the mutation (substitution, insertion or deletion) of one, two, three or more bases and then determining, in a reporter gene assay, whether this has increased the promoter activity.

Basically, the additional regulatory elements include heterologous promoters, enhancers, termination and polyadenylation signals and other expression control elements. Both inducible and constitutively regulatory sequences are known for the various cell types.

"Transcription-regulatory elements" generally comprise a promoter upstream of the gene sequence to be expressed, transcription initiation and termination sites and a polyadenylation signal.

The term "transcription initiation site" refers to a nucleic acid in the construct which corresponds to the first nucleic acid which is incorporated in the primary transcript, i.e. the mRNA precursor. The transcription initiation site may overlap with the promoter sequences.

The term "transcription termination site" refers to a nucleotide sequence which is normally at the 3' end of the gene of interest or of the gene section which is to be transcribed, and which brings about the termination of transcription by RNA polymerase.

The "polyadenylation signal" is a signal sequence which causes cleavage at a specific site at the 3' end of the eukaryotic mRNA and post-transcriptional incorporation of a sequence of about 100-200 adenine nucleotides (polyA tail) at the cleaved 3' end. The polyadenylation signal comprises the sequence AATAAA about 10-30 nucleotides upstream of the cleavage site and a sequence located downstream. Various polyadenylation elements are known such as tk polyA, SV40 late and early polyA or BGH polyA (described for example in U.S. Pat. No. 5,122,458).

"Translation regulatory elements" comprise a translation initiation site (AUG), a stop codon and a polyA signal for each polypeptide to be expressed. For optimum expression it may be advisable to remove, add or change 5'- and/or 3'-untranslated regions of the nucleic acid sequence which is to be expressed, in order to eliminate any potentially unsuitable additional translation initiation codons or other sequences which might affect expression at the transcription or expression level. In order to promote expression, ribosomal consensus binding sites may alternatively be inserted immediately upstream of the start codon. In order to produce a secreted polypeptide the gene of interest usually contains a signal sequence which codes for a signal precursor peptide which transports the synthesised polypeptide to and through the ER membrane. The signal sequence is often but not always located at the amino terminus of the secreted protein and is cleaved by signal peptidases after the protein has been filtered through the ER membrane. The gene sequence will usually but not necessarily contain its own signal sequence. If the native signal sequence is not present a heterologous signal sequence may be introduced in known manner.

Numerous signal sequences of this kind are known to the skilled man and deposited in sequence databanks such as GenBank and EMBL.

Another regulatory element is the internal ribosomal entry site (IRES). The IRES element comprises a sequence which functionally activates the translation initiation independently of a 5'-terminal methylguanosinium cap (CAP structure) and the upstream gene and in an animal cell allows the translation of two cistrons (open reading frames) from a single transcript. The IRES element provides an independent ribosomal entry site for the translation of the open reading frame located immediately downstream. In contrast to bacterial mRNA which may be multicistronic, i.e. it may code for numerous different polypeptides or products which are translated one after the other by the mRNA, the majority of mRNAs from animal cells are monocistronic and code for only one protein or product. In the case of a multicistronic transcript in a eukaryotic cell the translation would be initiated from the translation initiation site which was closest upstream and would be stopped by the first stop codon, after which the transcript would be released from the ribosome. Thus, only the first polypeptide or product coded by the mRNA would be produced during translation. By contrast, a multicistronic transcript with an IRES element which is functionally linked to the second or subsequent open reading frame in the transcript allows subsequent translation of the open reading frame located downstream thereof, so that two or more polypeptides or products coded by the same transcript are produced in the eukaryotic cell.

The IRES element may be of various lengths and various origins and may originate, for example, from the encephalomyocarditis virus (EMCV) or other Picorna viruses. Various IRES sequences and their use in the construction of vectors are described in the literature, cf. for example Pelletier et al., 1988; Jang et al., 1989; Davies et al., 1992; Adam et al., 1991; Morgan et al., 1992; Sugimoto et al., 1994; Ramesh et al., 1996; Mosser et al., 1997.

The gene sequence located downstream is functionally linked to the 3' end of the IRES element, i.e. the spacing is selected so that the expression of the gene is unaffected or only marginally affected or has sufficient expression for the intended purpose. The optimum permissible distance between the IRES element and the start codon of the gene located downstream thereof for sufficient expression can be determined by simple experiments by varying the spacing and determining the expression rate as a function of the spacing using reporter gene assays.

By the measures described it is possible to obtain an optimum expression cassette which is of great value for the expression of heterologous gene products. An expression cassette obtained by means of one or more such measures is therefore a further subject of the invention.

Hamster-Ubiquitin/S27a Promoter:

In another embodiment the expression vector according to the invention contains the ubiquitin/S27a promoter of the hamster, preferably functionally linked to the gene of interest and even more preferably functionally linked to the gene of interest and the gene which codes for a fluorescent protein or a selectable marker.

The ubiquitin/S27a promoter of the hamster is a powerful homologous promoter which is described in WO 97/15664. Such a promoter preferably has at least one of the following features: GC-rich sequence area, Sp1 binding site, polypyrimidine element, absence of a TATA box. Particularly preferred is a promoter which has an Sp1 binding site but no TATA box. Also preferred is a promoter which is constitutively activated and in particular is equally active under serum-containing, low-serum and serum-free cell culture conditions. In another embodiment it is an inducible promoter, particularly a promoter which is activated by the removal of serum.

A particularly advantageous embodiment is a promoter with a nucleotide sequence as contained in FIG. 5 of WO 97/15664. Particularly preferred are promoter sequences which contain the sequence from position −161 to −45 of FIG. 5.

The promoters used in the examples of the present patent specification each contain a DNA molecule with a sequence which corresponds to the fragment −372 to +111 from FIG. 5 of WO 97/15664 and represents the preferred promoter, i.e a preferred promoter should incorporate this sequence region.

Preparation of Expression Vectors According to the Invention:

The expression vector according to the invention may theoretically be prepared by conventional methods known in the art, as described by Sambrook et al. (1989), for example. Sambrook also describes the functional components of a vector, e.g. suitable promoters (in addition to the hamster ubiquitin/S27a promoter), enhancers, termination and polyadenylation signals, antibiotic resistance genes, selectable markers, replication starting points and splicing signals. Conventional cloning vectors may be used to produce them, e.g. plasmids, bacteriophages, phagemids, cosmids or viral vectors such as baculovirus, retroviruses, adenoviruses, adeno-associated viruses and herpes simplex virus, as well as synthetic or artificial chromosomes/mini chromosomes. The eukaryotic expression vectors typically also contain prokaryotic sequences such as, for example, replication origin and antibiotic resistance genes which allow replication and selection of the vector in bacteria. A number of eukaryotic expression vectors which contain multiple cloning sites for the introduction of a polynucleotide sequence are known and some may be obtained commercially from various companies such as Stratagene, La Jolla, Calif., USA; Invitrogen, Carlsbad, Calif., USA; Promega, Madison, Wis., USA or BD Biosciences Clontech, Palo Alto, Calif., USA.

The heterologous promoter, the gene (or genes) of interest, selectable markers and optionally the gene coding for a fluorescent protein, additional regulatory elements such as the internal ribosomal entry site (IRES), enhancers, a polyadenylation signal and other cis-active elements such as TE elements, for example, are introduced into the expression vector in a manner familiar to those skilled in the art. An expression vector according to the invention contains, at the minimum, a heterologous promoter, the gene of interest and a TE element. Preferably, the expression vector also contains a gene coding for a fluorescent protein. It is particularly preferred according to the invention to use a ubiquitin/S27a promoter as heterologous promoter. Particularly preferred is an expression vector in which the heterologous promoter, preferably a ubiquitin/S27a promoter, the gene of interest and a TE element are functionally linked together or are functionally linked.

Within the scope of the present description the term "functional linking" or "functionally linked" refers to two or more nucleic acid sequences or partial sequences which are positioned so that they can perform their intended function. For example, a promoter/enhancer, a promoter/TE element or a promoter/enhancer/TE element is functionally linked to a coding gene sequence if it is able to control or modulate the transcription of the linked gene sequence in the cis position. Generally, but not necessarily, functionally linked DNA sequences are close together and, if two coding gene sequences are linked or in the case of a secretion signal sequence, in the same reading frame. Although a functionally linked promoter is generally located upstream of the coding gene sequence it does not necessarily have to be close to it. Enhancers need not be close by either, provided that they assist the transcription or expression of the gene sequence. For this purpose they may be both upstream and downstream of the gene sequence, possibly at some distance from it. A polyadenylation site is functionally linked to a gene sequence if it is positioned at the 3' end of the gene sequence in such a way that the transcription progresses via the coding sequence to the polyadenylation signal. Linking may take place according to conventional recombinant methods, e.g. by the PCR technique, by ligation at suitable restriction cutting sites or by splicing. If no suitable restriction cutting sites are available synthetic oligonucleotide linkers or adaptors may be used in a manner known per se.

In one of the embodiments described, the heterologous promoter, preferably a ubiquitin/S27a promoter or CMV promoter, the gene of interest and the gene coding for a fluorescent protein are functionally linked together. This means for example that both the gene of interest and the gene coding for a fluorescent protein are expressed starting from the same heterologous promoter. In a particularly preferred embodiment the functional linking takes place via an IRES element, so that a bicistronic mRNA is synthesised from both genes. The expression vector according to the invention may additionally contain enhancer elements and/or TE elements which act functionally on one or more promoters.

Particularly preferred is an expression vector in which the heterologous promoter, preferably the ubiquitin/S27a promoter or a modified form thereof or the CMV promoter, is linked to an enhancer element, e.g. an SV40 enhancer or a CMV enhancer element, and a TE element.

Fundamentally, the expression of the genes within an expression vector may take place starting from one or more transcription units. The term transcription unit is defined as a region which contains one or more genes to be transcribed. The genes within a transcription unit are functionally linked to one another in such a way that all the genes to within such a unit are under the transcriptional control of the same promoter, promoter/enhancer or promoter/enhancer/TE element. As a result of this transcriptional linking of genes, more than one protein or product can be transcribed from a transcription unit and thus expressed. Each transcription unit contains the regulatory elements which are necessary for the transcription and translation of the gene sequences contained therein. Each transcription unit may contain the same or different regulatory elements. IRES elements or introns may be used for the functional linking of the genes within a transcription unit.

The expression vector may contain a single transcription unit for expressing the gene (or genes) of interest, the selectable marker and optionally the gene which codes for the fluorescent protein. Alternatively, these genes may also be arranged in two or more transcription units. Various combinations of the genes within a transcription unit are possible. In another embodiment of the present invention more than one expression vector consisting of one, two or more transcription units may be inserted in a host cell by cotransfection or in successive transfections in any desired order. Any combination of regulatory elements and genes on each vector can be selected provided that adequate expression of the transcription units is ensured. If necessary, other regulatory elements, such as TE elements, and genes, e.g. additional genes of interest or selectable markers, may be positioned on the expression vectors.

Also preferred according to the invention are those expression vectors which contain one or more TE elements and instead of the gene of interest have only a multiple cloning site which allows the cloning of the gene of interest via recognition sequences for restriction endonucleases. Numerous recognition sequences for all kinds of restriction endonucleases as well as the associated restriction endonucleases are known from the prior art. Preferably, sequences are used which consist of at least six nucleotides as recognition sequence. A list of suitable recognition sequences can be found for example in Sambrook et al., 1989.

Also preferred according to the invention are those expression vectors which instead of the gene of interest have only a multiple cloning site which allows the cloning of the gene of interest via recognition sequences for restriction endonucleases and which moreover have one or more, preferably multiple cloning sites at different positions of the expression vector, which additionally makes it possible to clone TE elements via recognition sequences for restriction endonucleases. Numerous recognition sequences for all kinds of restriction endonucleases as well as the associated restriction endonucleases are known from the prior art. Preferably, sequences are used which consist of at least six nucleotides as recognition sequence. A list of suitable recognition sequences can be found for example in Sambrook et al., 1989.

Host Cells:

For transfection with the expression vector according to the invention eukaryotic host cells are used, preferably mammalian cells and more particularly rodent cells such as mouse, rat and hamster cell lines. The successful transfection of the corresponding cells with an expression vector according to the invention results in transformed, genetically modified, recombinant or transgenic cells, which are also the subject of the present invention.

Preferred host cells for the purposes of the invention are hamster cells such as BHK21, BHK TK⁻, CHO, CHO-K1, CHO-DUKX, CHO-DUKX B1 and CHO-DG44 cells or derivatives/descendants of these cell lines. Particularly preferred are CHO-DG44, CHO-DUKX, CHO-K1 and BHK21 cells, particularly CHO-DG44 and CHO-DUKX cells. Also suitable are myeloma cells from the mouse, preferably NS0 and Sp2/0 cells and derivatives/descendants of these cell lines.

Examples of hamster and mouse cells which can be used according to the invention are given in Table 1 that follows. However, derivatives and descendants of these cells, other mammalian cells including but not restricted to cell lines of humans, mice, rats, monkeys, rodents, or eukaryotic cells, including but not restricted to yeast, insect, bird and plant cells, may also be used as host cells for the production of biopharmaceutical proteins.

TABLE 1

Hamster and Mouse Production Cell Lines

| Cell line | Accession Number |
| --- | --- |
| NS0 | ECASS No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21-derivative) | ATCC CRL-8544 |
| CHO | ECACC No. 8505302 |
| CHO-K1 | ATCC CCL-61 |
| CHO-DUKX (=CHO duk⁻ CHO/dhfr⁻) | ATCC CRL-9096 |
| CHO-DUKX B1 | ATCC CRL-9010 |
| CHO-DG44 | Urlaub et al; Cell 32[2], 405-412, 1983 |
| CHO Pro-5 | ATCC CRL-1781 |
| V79 | ATCC CCC-93 |
| B14AF28-G3 | ATCC CCL-14 |
| CHL | ECACC No. 87111906 |

The transfection of the eukaryotic host cells with a polynucleotide or one of the expression vectors according to the invention is carried out by conventional methods (Sambrook et al., 1989; Ausubel et al., 1994). Suitable methods of transfection include for example liposome-mediated transfection, calcium phosphate coprecipitation, electroporation, polycation- (e.g. DEAE dextran)-mediated transfection, protoplast fusion, microinjection and viral infections. According to the invention stable transfection is preferably carried out in which the constructs are either integrated into the genome of the host cell or an artificial chromosome/minichromosome, or are episomally contained in stable manner in the host cell. The transfection method which gives the optimum transfection frequency and expression of the heterologous gene in the host cell in question is preferred. By definition, every sequence or every gene inserted in a host cell is referred to as a "heterologous sequence" or "heterologous gene" in relation to the host cell. This applies even if the sequence to be introduced or the gene to be introduced is identical to an endogenous sequence or an endogenous gene of the host cell. For example, a hamster actin gene introduced into a hamster host cell is by definition a heterologous gene.

According to the invention, recombinant mammalian cells, preferably rodent cells, most preferably hamster cells such as CHO or BHK cells which have been transfected with one of the expression vectors according to the invention described herein are preferred.

In the recombinant production of heteromeric proteins such as e.g. monoclonal antibodies (mAb), the transfection of suitable host cells can theoretically be carried out by two different methods. mAb's of this kind are composed of a number of subunits, the heavy and light chains. Genes coding for these subunits may be accommodated in independent or multicistronic transcription units on a single plasmid with which the host cell is then transfected. This is intended to secure the stoichiometric representation of the genes after integration into the genome of the host cell. However, in the case of independent transcription units it must hereby be ensured that the mRNAs which encode the different proteins display the same stability and transcriptional and translational efficiency. In the second case, the expression of the genes take place within a multicistronic transcription unit by means of a single promoter and only one transcript is formed. By using IRES elements, a highly efficient internal translation initiation of the genes is obtained in the second and subsequent cistrons. However, the expression rates for these cistrons are lower than that of the first cistron, the translation initiation of which, by means of a so-called "cap"-dependent pre-initiation complex, is substantially more efficient than IRES-dependent translation initiation. In order to achieve a truly equimolar expression of the cistrons, additional inter-cistronic elements may be introduced, for example, which ensure uniform expression rates in conjunction with the IRES elements (WO 94/05785).

Another possible way of simultaneously producing a number of heterologous proteins, which is preferred according to the invention, is cotransfection, in which the genes are separately integrated in different expression vectors. This has the advantage that certain proportions of genes and gene products with one another can be adjusted, thereby balancing out any differences in the mRNA stability and in the efficiency of transcription and translation. In addition, the expression vectors are more stable because of their small size and are easier to handle both during cloning and during transfection.

In one particular embodiment of the invention, therefore, the host cells are additionally transfected, preferably cotransfected, with one or more vectors having genes which code for one or more other proteins of interest. The other vector or vectors used for the cotransfection code, for example, for the other protein or proteins of interest under the control of the same promoter, preferably under the control of the same promoter/enhancer combination or, particularly preferably, under the control of the same promoter/enhancer/TE element combination or under the control of the same promoter/enhancer combination with different TE elements and for at least one selectable marker, e.g. dihydrofolate reductase.

In another embodiment of the invention the vectors used for the transfection may contain one or more TE-elements in any combination, position and orientation.

In another particular embodiment of the invention the host cells are co-transfected with at least two eukaryotic expression vectors, at least one of the two vectors containing at least one gene which codes for at least the protein of interest, while the other vector contains one or more nucleic acids according to the invention in any combination, position and orientation, and optionally also codes for at least one gene of interest, and these nucleic acids according to the invention impart their transcription- or expression-enhancing activity to the genes of interest which are located on the other co-transfected vector, by co-integration with the other vector.

According to the invention the host cells are preferably established, adapted and cultivated under serum-free conditions, optionally in media which are free from animal proteins/peptides. Examples of commercially obtainable media include Ham's F12 (Sigma, Deisenhofen, DE), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif., USA), CHO-S-SFMII (Invitrogen), serum-free CHO-Medium (Sigma) and protein-free CHO-Medium (Sigma). Each of these media may optionally be supplemented with various compounds, e.g. hormones and/or other growth factors (e.g. insulin, transferrin, epidermal growth factor, insulin-like growth factor), salts (e.g. sodium chloride, calcium, magnesium, phosphate), buffers (e.g. HEPES), nucleosides (e.g. adenosine, thymidine), glutamine, glucose or other equivalent nutrients, antibiotics and/or trace elements. Although serum-free media are preferred according to the invention, the host cells may also be cultivated using media which have been mixed with a suitable amount of serum. In order to select genetically modified cells which express one or more selectable marker genes, one or more selecting agents are added to the medium.

The term "selecting agent" refers to a substance which affects the growth or survival of host cells with a deficiency for the selectable marker gene in question. Within the scope of the present invention, geneticin (G418) is preferably used as the medium additive for the selection of heterologous host cells which carry a wild-type or preferably a modified neomycin phosphotransferase gene. Preferably, G418 concentrations of between 100 and 800 µg/ml of medium are used, most preferably 200 to 400 µg G418/ml of medium. If the host cells are to be transfected with a number of expression vectors, e.g. if several genes of interest are to be separately introduced into the host cell, they generally have different selectable marker genes.

A selectable marker gene is a gene which allows the specific selection of cells which contain this gene by the addition of a corresponding selecting agent to the cultivation medium. As an illustration, an antibiotic resistance gene may be used as a positive selectable marker. Only cells which have been transformed with this gene are able to grow in the presence of the corresponding antibiotic and are thus selected. Untransformed cells, on the other hand, are unable to grow or survive under these selection conditions. There are positive, negative and bifunctional selectable markers. Positive selectable markers permit the selection and hence enrichment of transformed cells by conferring resistance to the selecting agent or by compensating for a metabolic or catabolic defect in the host cell. By contrast, cells which have received the gene for the selectable marker can be selectively eliminated by negative selectable markers. An example of this is the thymidine kinase gene of the Herpes Simplex virus, the expression of which in cells with the simultaneous addition of acyclovir or gancyclovir leads to the elimination thereof. The selectable markers used in this invention, including the amplifiable selectable markers, include genetically modified mutants and variants, fragments, functional equivalents, derivatives, homologues and fusions with other proteins or peptides, provided that the selectable marker retains its selective qualities. Such derivatives display considerable homology in the amino acid sequence in the regions or domains which are deemed to be selective. The literature describes a large number of selectable marker genes including bifunctional (positive/negative) markers (see for example WO 92/08796 and WO 94/28143). Examples of selectable markers which are usually used in eukaryotic cells include the genes for aminoglycoside phosphotransferase (APH), hygromycine phosphostransferase (HYG), dihydrofolate reductase (DHFR), thymidine kinase (TK), glutamine synthetase, asparagin synthetase and genes which confer resistance to neomycin (G418), puromycin, histidinol D, bleomycin, phleomycin and zeocin.

The term "modified neomycin-phosphotransferase (NPT)" covers all the mutants described in WO2004/050884, particularly the mutant D227G (Asp227Gly), which is characterised by the substitution of aspartic acid (Asp, D) for glycine (Gly, G) at amino acid position 227 and particularly preferably the mutant F240I (Phe240Ile), which is characterised by the substitution of phenylalanine (Phe, F) for isoleucine (Ile, I) at amino acid position 240.

The present invention therefore includes a method of preparing and selecting recombinant mammalian cells which comprises the following steps: (i) transfecting the host cells with genes which code for at least one protein/product of interest and a neomycin-phosphotransferase, preferably modified, wherein in order to enhance the transcription or expression at least the gene (or genes) of interest is functionally linked to at least one TE element; (ii) cultivating the cells under conditions that enable expression of the different genes; and (iii) selecting these co-integrated genes by cultivating the cells in the presence of a selecting agent such as e.g. G418. Preferably, the transfected cells are cultivated in medium in the absence of serum. Preferably the concentration of G418 is at least 200 µg/mL. However, the concentration may also be at least 400 µg/mL.

Amplifiable Selectable Marker Gene:

In addition, the cells according to the invention may optionally also be subjected to one or more gene amplification steps in which they are cultivated in the presence of a selecting agent which leads to amplification of an amplifiable selectable marker gene.

The prerequisite is that the host cells are additionally transfected with a gene which codes for an amplifiable selectable marker. It is conceivable for the gene which codes for an amplifiable selectable marker to be present on one of the expression vectors according to the invention or to be introduced into the host cell by means of another vector.

The amplifiable selectable marker gene usually codes for an enzyme which is needed for the growth of eukaryotic cells under certain cultivation conditions. For example, the amplifiable selectable marker gene may code for dihydrofolate reductase (DHFR). In this case the gene is amplified if a host cell transfected therewith is cultivated in the presence of the selecting agent methotrexate (MTX).

The following Table 2 gives examples of other amplifiable selectable marker genes and the associated selecting agents which may be used according to the invention, which are described in an overview by Kaufman, Methods in Enzymology, 185:537-566 (1990).

TABLE 2

Amplifiable selectable marker genes

| Amplifiable selectable marker gene | Accession number | Selecting agent |
| --- | --- | --- |
| dihydrofolate reductase | M19869 (hamster) E00236 (mouse) | methotrexate (MTX) |

TABLE 2-continued

Amplifiable selectable marker genes

| Amplifiable selectable marker gene | Accession number | Selecting agent |
|---|---|---|
| metallothionein | D10551 (hamster) M13003 (human) M11794 (rat) | cadmium |
| CAD (carbamoylphosphate synthetase:aspartate transcarbamylase:dihydroorotase) | M23652 (hamster) D78586 (human) | N-phosphoacetyl-L-aspartate |
| adenosine-deaminase | K02567 (human) M10319 (mouse) | Xyl-A- or adenosine, 2'deoxycoformycin |
| AMP (adenylate)-deaminase | D12775 (human) J02811 (rat) | adenine, azaserin, coformycin |
| UMP-synthase | J03626 (human) | 6-azauridine, pyrazofuran |
| IMP 5'-dehydrogenase | J04209 (hamster) J04208 (human) M33934 (mouse) | mycophenolic acid |
| xanthine-guanine-phosphoribosyltransferase | X00221 (*E. coli*) | mycophenolic acid with limiting xanthine |
| mutant HGPRTase or mutant thymidine-kinase | J00060 (hamster) M13542, K02581 (human) J00423, M68489(mouse) M63983 (rat) M36160 (Herpes virus) | hypoxanthine, aminopterine and thymidine (HAT) |
| thymidylate-synthetase | D00596 (human) M13019 (mouse) L12138 (rat) | 5-fluorodeoxyuridine |
| P-glycoprotein 170 (MDR1) | AF016535 (human) J03398 (mouse) | several drugs, e.g. adriamycin, vincristin, colchicine |
| ribonucleotide reductase | M124223, K02927 (mouse) | aphidicoline |
| glutamine-synthetase | AF150961 (hamster) U09114, M60803 (mouse) M29579 (rat) | methionine sulphoximine (MSX) |
| asparagine-synthetase | M27838 (hamster) M27396 (human) U38940 (mouse) U07202 (rat) | β-aspartylhydroxamate, albizziin, 5'azacytidine |
| argininosuccinate-synthetase | X01630 (human) M31690 (mouse) M26198 (bovine) | canavanin |
| ornithine-decarboxylase | M34158 (human) J03733 (mouse) M16982 (rat) | α-difluoro-methylornithine |
| HMG-CoA-reductase | L00183, M12705 (hamster) M11058 (human) | compactin |
| N-acetylglucosaminyl-transferase | M55621 (human) | tunicamycin |
| threonyl-tRNA-synthetase | M63180 (human) | borrelidin |
| $Na^+K^+$-ATPase | J05096 (human) M14511 (rat) | ouabain |

According to the invention the amplifiable selectable marker gene used is preferably a gene which codes for a polypeptide with the function of DHFR, e.g. for DHFR or a fusion protein from the fluorescent protein and DHFR. DHFR is necessary for the biosynthesis of purines. Cells which lack the DHFR genes cannot grow in purine-deficient medium. The DHFR gene is therefore a useful selectable marker for selecting and amplifying genes in cells cultivated in purine-free medium. The selecting medium used in conjunction with the DHFR gene is methotrexate (MTX).

Mammalian cells, preferably mouse myeloma and hamster cells, are preferred host cells for the use of DHFR as an amplifiable selectable marker. The cell lines CHO-DUKX (ATCC CRL-9096) and CHO-GD44 (Urlaub et al., 1983) are particularly preferred as they have no DHFR activity of their own, as a result of mutation. In order to be able to use the DHFR-induced amplification in other cell types as well which have their own endogenous DHFR activity, it is possible to use in the transfection process a mutated DHFR gene which codes for a protein with reduced sensitivity to methotrexate (Simonson et al., 1983; Wigler et al., 1980; Haber et al., 1982).

The DHFR marker is particularly suitable for the selection and subsequent amplification when using DHFR-negative basic cells such as CHO-DG44 or CHO-DUKX, as these cells do not express endogenous DHFR and therefore do not grow in purine-free medium. Consequently, the DHFR gene may be used here as a dominant selectable marker and the transformed cells are selected in hypoxanthine/thymidine-free medium.

The present invention therefore includes a method of preparing and selecting recombinant mammalian cells which comprises the following steps: (i) transfecting the host cells with genes which code for at least one protein/product of interest and the amplifiable selectable marker DHFR, wherein in order to enhance the transcription or expression at least the gene (or genes) of interest is functionally linked to at least one TE element; (ii) cultivating the cells under conditions that enable expression of the different genes; and (iii) amplifying these co-integrated genes by cultivating the cells in the presence of a selecting agent which allows the amplification of at least the amplifiable selectable marker gene, such as methotrexate. Preferably, the transfected cells are cultivated in hypoxanthine/thymidine-free medium in the absence of serum and with the addition of increasing concentrations of MTX. Preferably, the concentration of MTX in the first amplification step is at least 100 nM. The concentration of MTX may, however, also be at least 250 nM and may be increased step by step to 1 µM. In individual cases concentrations of over 1 µM may also be used, e.g. 2 µM.

The present invention also includes a method of preparing and selecting recombinant mammalian cells which comprises the following steps: (i) transfecting the host cells with genes which code for at least one protein/product of interest, a neomycin-phosphotransferase, preferably modified, and the amplifiable selectable marker DHFR, wherein in order to enhance the transcription or expression at least the gene (or genes) of interest is functionally linked to at least one TE element; (ii) cultivating the cells under conditions that enable expression of the different genes; (iii) selecting these co-integrated genes by cultivating the cells in the presence of a selecting agent such as e.g. G418, in hypoxanthine/thymidine-free medium; and (iv) amplifying these co-integrated genes by cultivating the cells in the presence of a selecting agent which allows the amplification of at least the amplifiable selectable marker gene, such as methotrexate. Preferably, the transfected cells are cultivated in hypoxanthine/thymidine-free medium, supplemented with at least 200 µg/mL G418, preferably 400 µg/mL or even more G418, in the absence of serum and with the addition of increasing concentrations of MTX. Preferably, the concentration of MTX in the first amplification step is at least 100 nM. The concentration of MTX may, however, also be at least 250 nM and may be increased step by step to 1 µM. In individual cases concentrations of over 1 µM may also be used, e.g. 2 µM.

It is also possible to select transformed cells by fluorescence-activated cell sorting (FACS). For this, bacterial β-galactosidase, cell surface markers or fluorescent proteins may be used (e.g. green fluorescent protein (GFP) and the variants thereof from *Aequorea victoria* and *Renilla reniformis* or other species; red fluorescent proteins and proteins which fluoresce in other colours and their variants from non-bioluminescent organisms such as e.g. *Discosoma* sp., *Anemonia* sp., *Clavularia* sp., *Zoanthus* sp., *Aequorea coerulescens*) for the selection of transformed cells.

Gene Expression and Selection of High-Producing Host Cells:

The term gene expression relates to the transcription and/or translation of a heterologous gene sequence in a host cell. The expression rate can be generally determined, either on the basis of the quantity of corresponding mRNA which is present in the host cell or on the basis of the quantity of gene product produced which is encoded by the gene of interest. The quantity of mRNA produced by transcription of a selected nucleotide sequence can be determined for example by northern blot hybridisation, ribonuclease-RNA-protection, in situ hybridisation of cellular RNA or by PCR methods (e.g. quantitative PCR) (Sambrook et al., 1989; Ausubel et al., 1994). Proteins which are encoded by a selected nucleotide sequence can also be determined by various methods such as, for example, ELISA, protein A HPLC, western blot, radioimmunoassay, immunoprecipitation, detection of the biological activity of the protein, immune staining of the protein followed by FACS analysis or fluorescence microscopy, direct detection of a fluorescent protein by FACS analysis or fluorescence microscopy (Sambrook et al., 1989; Ausubel et al., 1994). These methods makes it possible for example to investigate whether the TE element of SEQ ID No. 1 according to the invention, or any part, fragment or region thereof or the derivatives or combinations thereof, lead to an increase in the transcription or expression of a gene of interest.

By "enhanced expression, transcription or productivity" is meant an enhancement of the expression or synthesis of a heterologous sequence introduced into a host cell, for example a gene coding for a therapeutic protein, compared to a control. There is enhanced expression, transcription or productivity if a cell according to the invention is cultivated by a method described here according to the invention, and if this cell has at least a doubling of the specific productivity. There is also enhanced expression, transcription or productivity if the cell according to the invention has at least a tripling of the specific productivity. There is particularly enhanced expression, transcription or productivity if the cell according to the invention has at least a quadrupling of the specific productivity. There is particularly enhanced expression, transcription or productivity if the specific productivity of the cell according to the invention is increased at least five-fold. There is particularly enhanced expression, transcription or productivity if the specific productivity of the cell according to the invention is increased at least six-fold. There is particularly enhanced expression, transcription or productivity if the specific productivity of the cell according to the invention is increased at least seven-fold.

Enhanced expression, transcription or productivity can be achieved both by using one of the expression vectors according to the invention and by using one of the methods according to the invention.

The corresponding processes may be combined with a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of cis-active elements for manipulating the chromatin structure (e.g. LCR, UCOE, EASE, isolators, S/MARs, STAR elements), on the use of (artificial) transcription factors, treatment of the cells with natural or synthetic agents for up-regulating endogenous or heterologous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences (Hemann et al., 1994) or in vitro amplification systems based on DNA concatemers (Monaco et al., 1996).

In a further embodiment the present invention thus also relates to processes for obtaining and selecting recombinant mammalian cells which express at least one heterologous gene of interest and are characterised in that (i) recombinant mammalian cells are transfected with an expression vector according to the invention and the gene for an amplifiable selectable marker gene; (ii) the mammalian cells are cultivated under conditions which allow expression of the gene or genes of interest, the modified neomycin phosphotransferase gene and the gene which codes for a fluorescent protein; (iii) the mammalian cells are cultivated in the presence of at least one selecting agent which acts selectively on the growth of mammalian cells and gives preference to the growth of those cells which express the neomycin phosphotransferase gene; (iv) the mammalian cells which exhibit high expression of the fluorescent protein are sorted out by flow-cytometric analysis; (v) the sorted cells are cultivated under conditions under which the amplifiable selectable marker gene is expressed; and (vi) a selecting agent is added to the culture medium which results in the amplification of the amplifiable selectable marker gene.

Also preferred according to the invention is a process in which production cells are replicated and used to prepare the coding gene product of interest. For this, the selected high producing cells are preferably cultivated in a serum-free culture medium and preferably in suspension culture under conditions which allow expression of the gene of interest. The protein/product of interest is preferably obtained from the cell culture medium as a secreted gene product. If the protein is expressed without a secretion signal, however, the gene product may also be isolated from cell lysates. In order to obtain a pure homogeneous product which is substantially free from other recombinant proteins and host cell proteins, conventional purification procedures are carried out. First of all, cells and cell debris are removed from the culture medium or lysate. The desired gene product can then be freed from contaminating soluble proteins, polypeptides and nucleic acids, e.g. by fractionation on immunoaffinity and ion exchange columns, ethanol precipitation, reversed phase HPLC or chromatography on Sephadex, silica or cation exchange resins such as DEAE. Methods which result in the purification of a heterologous protein expressed by recombinant host cells are known to the skilled man and described in the literature, e.g. by Harris et al., 1995 and Scopes 1988.

Compositions According to the Invention

The present invention relates to a nucleic acid which contains TE-13 (SEQ ID No. 15) contains or a fragment of TE-13 (SEQ ID No. 15) or the complementary nucleotide sequences thereof or a derivative of TE-13 (SEQ ID No. 15) or a fragment thereof or the complementary nucleotide sequences thereof, and which on chromosomal integration leads to an increase in the transcription or expression of a gene of interest in an expression system.

The present invention relates to a nucleic acid which contains TE-13 (SEQ ID No. 15) or a fragment of TE-13 (SEQ ID No. 15) or the complementary nucleotide sequences thereof or a derivative of TE-13 (SEQ ID No. 15) or a fragment thereof or the complementary nucleotide sequences thereof, and which on chromosomal integration leads to an increase in the transcription or expression of a gene of interest in an expression system, with the proviso that the fragment comprises at least one sequence region from the nucleic acid region between 1 bp and 1578 bp (in relation to SEQ ID No. 01).

The present invention relates to a nucleic acid which contains TE-13 (SEQ ID No. 15) or a fragment of TE-13 (SEQ ID No. 15) or the complementary nucleotide sequences thereof or a derivative of TE-13 (SEQ ID No. 15) or a fragment thereof or the complementary nucleotide sequences thereof, and which on chromosomal integration leads to an increase in the transcription or expression of a gene of interest in an expression system, with the proviso that the fragment comprises at least one sequence region of TE-09 (SEQ ID No. 11) or TE-08 (SEQ ID No. 11) or TE-13 (SEQ ID No. 15).

By a sequence region is meant a nucleic acid region of at least 10 bp, 15 bp, 20 bp, 50 bp, 100 bp.

The enhanced expression of the gene of interest can be measured for example by measuring the product titre by ELISA.

In a preferred embodiment the invention relates to a nucleic acid which contains TE-08 (SEQ ID No. 10) or a fragment of TE-08 (SEQ ID No. 10) or the complementary nucleotide sequences thereof or a derivative of TE-08 (SEQ ID No. 10) or a fragment thereof or the complementary nucleotide sequences thereof, and which on chromosomal integration leads to an increase in the transcription or expression of a gene of interest in an expression system.

In a preferred embodiment of the above nucleic acid according to the invention the proviso is that the fragment must also include at least one sequence region from the nucleic acid region between 1 bp and 1578 bp (in relation to SEQ ID No. 01).

In a particularly preferred embodiment of the above nucleic acid according to the invention there is the proviso that the fragment also includes at least one sequence region of TE-09 (SEQ ID No. 11) or TE-08 (SEQ ID No. 11) or TE-13 (SEQ ID No. 15).

By a sequence region is meant a nucleic acid region of at least 10 bp, 15 bp, 20 bp, 50 bp, 100 bp.

In another embodiment the invention relates to a nucleic acid which contains SEQ ID No. 1 or a fragment of SEQ ID No. 1 or the complementary nucleotide sequences thereof or a derivative of SEQ ID No. 1 or a fragment thereof or the complementary nucleotide sequences thereof, which on chromosomal integration leads to an increase in the transcription or expression of a gene of interest in an expression system.

In a preferred embodiment of the above-mentioned nucleic acid according to the invention there is the proviso that the fragment also comprises at least one sequence region from the nucleic acid region between 1 bp and 1578 bp (in relation to SEQ ID No. 01).

In a particularly preferred embodiment of the above-mentioned nucleic acid according to the invention there is the proviso that the fragment also comprises at least one sequence region of TE-09 (SEQ ID No. 11) or TE-08 (SEQ ID No. 11) or TE-13 (SEQ ID No. 15).

By a sequence region is meant a nucleic acid region of at least 10 bp, 15 bp, 20 bp, 50 bp, 100 bp.

The present invention also relates to a nucleic acid (=TE element) for increasing the transcription or expression of a gene of interest with SEQ ID No. 1 or a fragment or derivative thereof or the complementary nucleotide sequences thereof, which leads to an increase in the transcription or expression of a gene of interest.

The increase in the expression of the gene of interest can be measured for example by measuring the product titre by ELISA.

The present invention particularly relates to a nucleic acid according to the invention, which hybridises under stringent conditions (a) with the region of nucleic acid sequence TE-13 (SEQ ID No. 15) or TE-08 (SEQ ID No. 10) or (b) the complementary nucleic acid sequences thereof or (c) a nucleic acid sequence which has at least about 70% sequence identity, preferably at least about 80% sequence identity, preferably at least about 85% sequence identity, most preferably at least about 90% sequence identity and most preferably at least about 95% sequence identity with (a) or (b), In a special embodiment the nucleic acid according to the invention has a length of at least 511 bp (=length TE-13, SEQ ID No. 15) or at least 1015 bp (=length TE-08, SEQ ID No. 10).

In a preferred embodiment the present invention relates to the 5' fragment of the TE element TE-00 (SEQ ID No. 2). This corresponds to the part of SEQ ID No. 1 between 1 bp and 1578 bp or the complementary nucleotide sequence thereof.

The present invention particularly relates to a nucleic acid or a transcription-enhancing or expression-enhancing nucleic acid element (TE element), which contains TE-13 (SEQ ID No. 15) or TE-08 (SEQ ID No. 10) or a derivative thereof or the complementary nucleotide sequences thereof, which on chromosomal integration leads to an increase in the transcription or expression of a gene of interest.

The present invention preferably relates to an isolated nucleic acid or an isolated nucleic acid molecule or an isolated nucleic acid sequence or an isolated transcription-enhancing nucleic acid element or an isolated TE element.

The present invention particularly relates to an isolated nucleic acid which contains TE-08 (SEQ ID No. 10) or the complementary nucleotide sequence thereof and which on chromosomal integration leads to an increase in the transcription or expression of a gene of interest in an expression system.

In one embodiment the nucleic acid or the transcription-enhancing nucleic acid element or the isolated nucleic acid contains a derivative of a TE element or of SEQ ID No. 1, which has at least about 70% sequence identity, preferably at least about 80% sequence identity, most preferably at least about 90% sequence identity and most preferably at least about 95% sequence identity with the corresponding part of the TE element sequence or the complementary sequence thereof, particularly with the sequence region between nucleotide position 1 bp and 1578 bp in relation to SEQ ID No. 1, corresponding to the sequence region 5' of the TE-00 sequence, and particularly preferably with TE-13 (SEQ ID No. 15) or TE-08 (SEQ ID No. 10).

In a preferred embodiment the nucleic acid or the transcription-enhancing nucleic acid element or the isolated nucleic acid contains a derivative of a TE-08 nucleic acid (SEQ ID No. 10) or preferably of a TE-13 nucleic acid (SEQ ID No. 15), which has at least about 70% sequence identity, preferably at least about 80% sequence identity, most preferably at least about 90% sequence identity and most preferably at least about 95% sequence identity with the corresponding part of the TE element sequence or the complementary sequence thereof.

In another embodiment the invention relates to a nucleic acid or a transcription-enhancing nucleic acid element or an isolated nucleic acid or a derivative of a TE element, which hybridise(s) with the sequence of a TE element or with the complementary sequence of a TE element, particularly with the sequence region between nucleotide position 1 bp and 1578 bp in relation to SEQ ID No. 1, corresponding to sequence region 5' of the TE-00 sequence (SEQ ID No. 2), or hybridises particularly with the TE-08 element (SEQ ID No. 10). Preferably the hybridisation is carried out under stringent hybridisations and washing conditions.

In another preferred embodiment the nucleic acid according to the invention or the transcription-enhancing element (TE element) is selected from among: TE-00 (SEQ ID No. 2), TE-01 (SEQ ID No. 3), TE-02 (SEQ ID No. 4), TE-03 (SEQ ID No. 5), TE-04 (SEQ ID No. 6), TE-06 (SEQ ID No. 8), TE-07 (SEQ ID No. 9), TE-08 (SEQ ID No. 10), TE-10 (SEQ ID No. 12), TE-11 (SEQ ID No. 13), TE-12 (SEQ ID No. 14), TE-13 (SEQ ID No. 15), TE-14 (SEQ ID No. 16), TE-15 (SEQ ID No. 17), TE-16 (SEQ ID No. 18), TE-17 (SEQ ID No. 19), TE-18 (SEQ ID No. 20) and TE-21 (SEQ ID No. 21).

In another embodiment the nucleic acid or the transcription-enhancing element (TE element) is characterised in that the nucleic acid is TE-00 (SEQ ID No. 2), TE-06 (SEQ ID No. 8), TE-10 (SEQ ID No. 12), TE-11 (SEQ ID No. 13) or TE-12 (SEQ ID No. 14), preferably TE-06 (SEQ ID No. 8).

In a preferred embodiment the nucleic acid or the transcription-enhancing element (TE element) is characterised in that the nucleic acid is TE-01 (SEQ ID No. 3), TE-02 (SEQ ID No. 4), TE-03 (SEQ ID No. 5), TE-07 (SEQ ID No. 9), TE-08 (SEQ ID No. 10).

In a particularly preferred embodiment the nucleic acid or the transcription-enhancing element is TE-08 (SEQ ID No. 10).

In another embodiment the nucleic acid or the transcription-enhancing element (TE element) is characterised in that it is a fragment or derivative of TE-01 (SEQ ID No. 3) is, preferably TE-13 (SEQ ID No. 15), TE-14 (SEQ ID No. 16), TE-15 (SEQ ID No. 17), TE-16 (SEQ ID No. 18), TE-17 (SEQ ID No. 19), TE-18 (SEQ ID No. 20).

In a preferred embodiment the nucleic acid according to the invention is TE-13 (SEQ ID No. 15).

In another embodiment the nucleic acid according to the invention or the fragment or the derivative is an isolated nucleic acid.

The present invention also relates to a nucleic acid according to the invention according to one of claims 1 to 12, characterised in that a nucleic acid containing TE-13 (SEQ ID No. 15) or TE-08 (SEQ ID No. 10) or TE-07 (SEQ ID No. 9) or TE-06 (SEQ ID No. 8) or a fragment of these sequences or the complementary nucleotide sequences thereof or a derivative of these sequences or a derivative of fragments of these sequences, preferably TE-13 (SEQ ID No. 15) or TE-08 (SEQ ID No. 10) or a fragment of these sequences or a derivative of these sequences or a derivative of fragments of these sequences or the complementary nucleotide sequences thereof, is linked to a heterologous sequence.

The nucleic acid linked to a heterologous gene sequence may in a preferred embodiment be an expression vector, for example plasmids, bacteriophages, phagemids, cosmids, viral vectors or particularly a targeting vector.

The nucleic acid linked to a heterologous gene sequence may however also be any other synthetic nucleic acid molecule such as e.g. synthetic, artificial or mini-chromosomes.

The present invention further relates to a eukaryotic expression vector, characterised in that this expression vector contains one or more nucleic acids according to the invention or one or more transcription-enhancing elements (TE element) according to the invention.

In a special embodiment the eukaryotic expression vector is characterised in that it contains a promoter and/or a heterologous gene of interest and/or a selectable marker and/or optionally an enhancer.

The present invention further relates to a eukaryotic expression vector characterised in that this expression vector contains one or more nucleic acids according to the invention or one or more transcription-enhancing elements (TE element) and a promoter and/or a heterologous gene of interest and/or a selectable marker and/or optionally an enhancer according to the invention.

In another embodiment the eukaryotic expression vector is characterised in that it is a targeting vector for the deliberate integration of the gene of interest.

In a preferred embodiment the eukaryotic expression vector is characterised in that the promoter is a heterologous promoter such as the early promoter of human cytomegaly virus (CMV-promoter), SV40 early promoter, adenovirus major late promoter, mouse metallothionein-I promoter, the long terminal repeat region of Rous Sarcoma Virus, actin-, immunoglobulin or heat-shock-promoter(s), preferably CMV-promoter.

In another preferred embodiment the eukaryotic expression vector is characterised in that the promoter is a heterologous promoter, preferably ubiquitin/S27a-promoter, most preferably hamster ubiquitin/S27a-promoter.

In a special embodiment the eukaryotic expression vector is characterised in that it contains a combination of several identical or different nucleic acids or TE-elements according to the invention in any orientation to one another, wherein one or more nucleic acids or TE-elements are positioned in front of (i.e. 5' of) and/or one or more nucleic acids or TE-elements are positioned (i.e. 3' of) the gene of interest.

In a preferred embodiment the eukaryotic expression vector is characterised in that the combined nucleic acids or TE elements are TE-06 (SEQ ID No. 8) and particularly preferably TE-08 (SEQ ID No. 10).

Preferred combinations of nucleic acids or TE elements are a TE-06 element (SEQ ID No. 8) in front of (i.e. 5' of) and a TE-06 element (SEQ ID No. 8) behind (i.e. 3' of) the gene of interest and three TE-06-elements (SEQ ID No. 8) behind (i.e. 3' of) the gene of interest (cf also FIG. 13).

In a particularly preferred embodiment the eukaryotic expression vector is characterised in that one or more TE-08-nucleic acid(s) or element(s) (SEQ ID No. 10) are positioned in front of (i.e. 5' of) and one or more behind (i.e. 3' of) the gene of interest, preferably one TE-08 element (SEQ ID No. 10) in front and one behind (cf also FIG. 13).

Other preferred combinations of TE-nucleic acids or elements are 2 TE-08 nucleic acids/elements (SEQ ID No. 10) before and/or after the gene of interest.

In another embodiment the eukaryotic expression vector is characterised in that a plurality of TE-06-nucleic acids or elements (SEQ ID No. 8) are positioned behind (3' of) the gene of interest, preferably 3 (cf FIG. 13).

In a preferred embodiment the eukaryotic expression vector is characterised in that a combination of one or more TE-08-nucleic acid(s) or element(s) (SEQ ID No. 10) with one or more TE-06 nucleic acids or element(s) (SEQ ID No. 8) are positioned in front of (i.e. 5' of) and/or behind (i.e. 3' of) the gene of interest; the preferred combination is a combination of a TE-08 nucleic acid or element (SEQ ID No. 10) followed by a TE-06-nucleic acid or element (SEQ ID No. 8) in front of (i.e. 5' of) the gene of interest. (Cf also FIG. 13).

In a preferred embodiment the eukaryotic expression vector is characterised in that it additionally contains an integrase.

In another preferred embodiment the host cells are co-transfected with at least two eukaryotic expression vectors, while at least one of the two vectors contains at least one gene which codes for at least one protein of interest and the other vector contains one or more nucleic acid according to the inventions in any combination, position and orientation, and optionally also codes for at least one gene of interest, and these nucleic acids according to the invention impart their transcription- or expression-enhancing effect to the genes of interest which are located on the other co-transfected vector, by co-integration with the other vector.

In a special embodiment the eukaryotic expression vector is characterised in that the selectable marker is DHFR or Neo, for example Neo F240I.

The invention further relates to a method of preparing a eukaryotic expression vector, characterised by the integration of a nucleic acid according to the invention in an expression vector.

The invention further relates to a eukaryotic host cell characterised in that it contains a eukaryotic expression vector according to the invention.

In a special embodiment the eukaryotic host cell is characterised in that it is a high producer, i.e. it has a higher specific productivity than a comparable eukaryotic host cell without a TE element or nucleic acid according to the invention, this host cell having an expression level which is increased two-fold, three-fold, four-fold, five-fold, six-fold, seven-fold or ten-fold or one which is increased more than two-fold, more than three-fold, more than four-fold, more than five-fold, more than seven-fold or more than ten-fold, preferably up to five-fold or more than three-fold.

In a particularly preferred embodiment the eukaryotic host cell is characterised in that the expression vector is stably integrated in the genome.

In another embodiment the eukaryotic host cell is a hamster or mouse cell such as for example a CHO, NS0, Sp2/0-Ag14, BHK21, BHK TK$^-$, HaK, 2254-62.2 (BHK-21-derivative), CHO-K1, CHO-DUKX (=CHO duk$^-$, CHO/dhfr$^-$), CHO-DUKX B1, CHO-DG44, CHO Pro-5, V79, B14AF28-G3, CHL cell, preferably a CHO cell and particularly preferably a CHO-DG44 cell.

In another embodiment the eukaryotic host cell is a mammalian cell, including but not restricted to human, mouse, rat, monkey or rodent cell lines.

In another embodiment the host cell is a eukaryotic cell including but not restricted to yeast, insect, bird and plant cells.

In another special embodiment the eukaryotic host cell is characterised in that it additionally contains an anti-apoptosis gene such as BCL-xL, BCL-2, BCL-w, BFL-1, A1, MCL-1, BOO, BRAG-1, NR-13, CDN-1, CDN-2, CDN-3, BHRF-1, LMW5-HL or CED-9, preferably Bcl-xL or BCL-2, most preferably BCL-xL.

The present invention further relates to a method of developing a high-producing stably transfected eukaryotic host cell line, characterised by the following steps:

(a) integrating at least one nucleic acid according to the invention or one TE element according to the invention in a eukaryotic expression vector containing a gene of interest, (b) transfecting a eukaryotic host cell with this expression vector, (c) selecting a highly-productive transfected host cell.

The present invention further relates to a method of developing a high-producing stably transfected eukaryotic host cell line, characterised by the following steps:

(a) integrating a gene (genes) of interest in a eukaryotic expression vector containing at least one nucleic acid according to the invention or a TE element according to the invention (b) transfecting a eukaryotic host cell with this expression vector, (c) selecting a highly-productive transfected host cell.

In a special embodiment the method is characterised by at least one additional amplification step.

The present invention also relates to a method of preparing and selecting recombinant mammalian cells, characterised by the following steps:

(a) transfecting the host cells with genes that codes at least for a protein/product of interest, a neomycin-phosphotransferase, preferably modified, and the amplifiable selectable marker DHFR, wherein in order to enhance the transcription or expression at least the gene (or genes) of interest is or are functionally linked to at least one nucleic acid according to the invention, (b) cultivating the cells under conditions which enable expression of the different genes, (c) selecting these co-integrated genes by cultivating the cells in the presence of a selecting agent, such as e.g. G418, in a hypoxanthine/thymidine-free medium and (d) amplifying these co-integrated genes by cultivating the cells in the presence of a selecting agent which allows the amplification of at least the amplifiable selectable marker gene, such as e.g. methotrexate.

In a particular embodiment this method is characterised in that the transfected cells are cultivated in hypoxanthine/thymidine-free medium, supplemented with at least 200 µg/mL G418, preferably 400 µg/mL or more G418, in the absence of serum and with the addition of increasing concentrations of MTX.

In another particular embodiment this method is characterised in that the concentration of MTX in the first amplification step is at least 100 nM or at least 250 nM and is increased stepwise to 1 µM or above. In individual cases, the MTX concentration may be 2 µM.

In another special embodiment the method is characterised by an additional cloning step.

In another embodiment of the method according to the invention the host cell is a rodent/hamster cell such as for example a CHO, NS0, Sp2/0-Ag14, BHK21, BHK TK$^-$, HaK, 2254-62.2 (BHK-21-derivative), CHO-K1, CHO-DUKX (=CHO duk$^-$, CHO/dhfr$^-$), CHO-DUKX B1, CHO-DG44, CHO Pro-5, V79, B14AF28-G3, CHL cell, preferably a CHO cell and particularly preferably a CHO-DG44 cell.

In a preferred method according to the invention the expression vector contains a selectable marker such as DHFR or NPT, for example NPT F240I or NPT D227G.

In a particularly preferred embodiment of the method according to the invention the proportion of high producers is increased up to two-fold, three-fold, four-fold, five-fold, six-fold, seven-fold or ten-fold or more than two-fold, more than three-fold, more than four-fold, more than five-fold, more than seven-fold or more than ten-fold, preferably up to five-fold or more than three-fold.

The present invention further relates to a method of preparing a biopharmaceutical product, characterised by the following steps:

(a) integrating at least one nucleic acid according to the invention or one TE element according to the invention in a eukaryotic expression vector containing a gene of interest, (b) transfecting a eukaryotic host cell with this expression vector, (c) selecting a highly-productive transfected host cell and (d) cultivating the highly-productive transfected host cell obtained under conditions which allow expression of the gene(s) of interest.

The present invention further relates to a method of developing a high-producing stably transfected eukaryotic host cell line, characterised by the following steps:

(a) integrating a gene (genes) of interest in a eukaryotic expression vector containing at least one nucleic acid according to the invention or one TE element according to the invention (b) transfecting a eukaryotic host cell with this expression vector, (c) selecting a highly-productive transfected host cell and (d) cultivating the highly-productive transfected host cell obtained under conditions which allow expression of the gene(s) of interest.

In a special embodiment the method according to the invention is characterised by at least one additional amplification step.

In a special embodiment the method according to the invention is characterised by the following additional step:

(e) harvesting and purifying the protein of interest.

The present invention further relates to the use of a nucleic acid according to the invention or of a transcription-enhancing element (TE element) according to the invention in a eukaryotic expression vector, for increasing the transcription or expression of a gene of interest in an expression system in a eukaryotic host cell or for preparing a biopharmaceutical product.

The present invention also relates to the use of a nucleic acid according to the invention or of a transcription-enhancing element (TE element) according to the invention for producing transgenic animals or plants.

The present invention further relates to the use of a nucleic acid according to the invention or of a transcription-enhancing element (TE element) according to the invention in gene therapy.

The present invention particularly relates to the use of a nucleic acid according to the invention or of a transcription-enhancing element (TE element) according to the invention as a medicament or in a pharmaceutical composition.

The present invention further relates to a kit consisting of a nucleic acid according to the invention or (a) TE element(s) according to the invention, optionally expression vector(s), optionally host cell(s) and optionally transfection reagent(s).

In a preferred embodiment the present invention relates to a nucleic acid, particularly an isolated nucleic acid, more precisely a transcription-enhancing or expression-enhancing nucleic acid element (TE element) with SEQ ID No. 1 or a fragment or a derivative thereof, which on chromosomal integration leads to an increase in the transcription or expression of a gene of interest, with the exclusion of the TE element TE-00 (SEQ ID No. 2).

In another embodiment the present invention relates to a nucleic acid according to the invention with the exclusion of the TE elements TE-00 (SEQ ID No. 2), TE-04 (SEQ ID No. 6) and TE-06 (SEQ ID No. 8).

In another embodiment the present invention relates to a nucleic acid according to the invention with the exclusion of the TE elements TE-00 (SEQ ID No. 2), TE-04 (SEQ ID No. 6), TE-05 (SEQ ID No. 7) and TE-06 (SEQ ID No. 8).

The increase in the expression of the gene of interest can be measured for example by measuring the product titre using ELISA.

Another embodiment of the present invention relates to a TE element, fragment or derivative according to the invention, which is over 160 bp long, preferably over 170 bp long. In a special embodiment the TE element fragment is between 160 bp and 1.2 kb or between 170 bp and 1 kb, preferably over 200 bp and between 200 bp and 1 kb long.

In a preferred embodiment the TE element fragment is in the part of SEQ ID No. 1 between 1 bp and 1578 bp (this corresponds to a fragment 5' of the element TE-00 (SEQ ID No. 2) and is over 113 bp long or over 132 bp and preferably over 160 bp or over 170 bp long. In a special embodiment the TE element fragment is between 113 bp and 1.2 kb or between 132 bp and 1.2 kb or between 160 bp and 1.2 kb, preferably over 200 bp and between 200 bp and 1 kb long.

In another embodiment the TE element fragment is present without any adjacent sequences. By this is meant that the fragment is not part of a larger sequence or a sequence region, for example no other sequences are attached in front of (5') or behind (3') it.

In another special embodiment the present invention relates to a nucleic acid according to the invention which does not contain any CpG islands.

It is apparent from the following experiments that when eukaryotic host cells with and without TE element are compared, an up to seven-fold increase in the relative change in the specific productivity of the gene of interest can be shown.

The collection of data on the product titre and specific productivity showed that on average almost all the cell pools with TE elements which were fragments or derivatives of SEQ ID No. 1 expressed more genes of interest than cell pools without a TE element. The TE-elements 01 (SEQ ID No. 3), 02 (SEQ ID No. 4) and 08 (SEQ ID No. 10) yielded the highest productivity in two independent transfection series in which a different selectable marker (NPT or DHFR) was used in each case. They are capable of increasing the productivity by a factor of 4-7. Certainly, the TE elements 01 (SEQ ID No. 3) and 02 (SEQ ID No. 4) at 3 kb and 2.5 kb are very large for additionally attaching to an expression vector. Of more interest, on the other hand, is the TE element 08 (SEQ ID No. 10), which is only 1 kb in size, which is capable of increasing expression by a factor of 5-6. The TE element 06 (SEQ ID No. 8) in two transfection series yielded a tripling of the specific productivity with a size of only 381 bp. It is highly advantageous to leave the expression vectors as small as possible, as smaller vectors are generally more stable and are easier to handle both during cloning and during transfection. Therefore, the TE-elements 06 (SEQ ID No. 8) and 08 (SEQ ID No. 10) are particularly interesting for use as transcription-promoting elements.

The following Examples also show that the cell pools which contained the TE element 03 (SEQ ID No. 5), 04 (SEQ ID No. 6) or 07 (SEQ ID No. 9) showed an approximately 3- to 3.5-fold expression of the gene of interest and cell pools with the TE elements 10 (SEQ ID No. 12), 11 (SEQ ID No. 13) or 12 (SEQ ID No. 14) showed an approximately doubled expression of the gene of interest The TE element 08 (SEQ ID No. 10) in conjunction with NPT F240I as selectable marker, at factor 5, demonstrated the greatest increase in the specific productivity of the gene of interest compared with the control pools with no TE element. In conjunction with DHFR as selectable marker the TE element 08 (SEQ ID No. 10) shows an even better increase of about factor 6.0.

Furthermore, TE element 02 (SEQ ID No. 4) in the test series with DHFR as selectable marker shows an increase in the productivity of the gene of interest by a factor 6.8.

The Examples that follow also show that pools with the TE elements 05 (SEQ ID No. 7) and 09 (SEQ ID No. 11) in one test series exhibited no increase in the expression of the gene of interest and in one test series even showed a lower expression of the gene of interest than the control pools. These two elements and possibly partial fragments in these sequence regions can thus have a repressive effect under certain circumstances, although this is not necessarily the case.

Moreover, in the Examples that follow, the relative changes in the specific productivity for the different TE-elements tested are achieved largely independently of the vector system, i.e. independently of the selectable marker used or independently of the particular gene of interest.

The Examples that follow also show that the change in the expression of the marker gene correlates with the changes in the expression of the gene of interest.

It is also apparent from the following Examples that none of the TE elements tested has an enhancing effect. It is thus clear that the TE-elements only cause an increase in the expression of the gene of interest at a chromosomal level.

The Examples that follow also show that the combination or concatenation of a plurality of identical or different short TE-elements such as e.g. TE element 06 and 08 can lead to an additional expression-enhancing effect.

The following Examples are provided to illustrate the present invention, and should not be construed as limiting thereof.

All references cited herein are incorporated by reference in the application in their entireties.

EXAMPLES

Abbreviations
AP: alkaline phosphatase
Asp (=D): aspartic acid
bp: base pair
CHO: Chinese Hamster Ovary
DHFR: dihydrofolate-reductase
ELISA: enzyme-linked immunosorbant assay
FACS: fluorescence-activated cell sorter
GFP: green fluorescent protein
Gly (=G): glycine
HT: hypoxanthine/thymidine
IgG: Immunoglobulin G
Ile (=I): isoleucine
IRES: internal ribosomal entry site
kb: kilobase
mAb: monoclonal antibody
MCP-1: monocyte chemoattractant protein-1
MTX: methotrexate
NPT: neomycin-phosphotransferase
PCR: polymerase chain reaction
Phe (=F): phenylalanine
SEAP: secreted alkaline phosphatase
Ub: ubiquitin
UTR: untranslated region Methods
Cell Culture and Transfection The cells CHO-DG44/dhfr$^{-/-}$ (Urlaub et al., 1983) were permanently cultivated as suspension cells in serum-free CHO-S-SFMII medium supplemented with hypoxanthine and thymidine (HT) (Invitrogen GmbH, Karlsruhe, DE) in cell culture flasks at 37° C. in a damp atmosphere and 5% $CO_2$. The cell counts and viability were determined with a Coulter Counter Z2 (Beckmann Coulter) or with a Cedex (Innovatis) and the cells were then seeded in a concentration of $1-3\times10^5$/mL and run every 2-3 days.

Lipofectamine Plus Reagent (Invitrogen GmbH) was used for the transfection of CHO-DG44. For each transfection mixture a total of 1.0-1.3 µg of plasmid-DNA, 4 µL of lipofectamine and 6 µL of Plus reagent were mixed together according to the manufacturer's instructions and added in a volume of 200 µL to $6\times10^5$ cells in 0.8 mL of HT-supplemented CHO-S-SFMII medium. After three hours' incubation at 37° C. in a cell incubator 2 mL of HT-supplemented CHO-S-SFMII medium was added. After a cultivation time of 48 hours, the transfection mixtures were either harvested (transient transfection) or subjected to selection. For the NPT-based selection the cells were transferred 2 days after transfection into HT-supplemented CHO-S-SFMII medium with 400 µg/mL of G418 (Invitrogen). For the DHFR-based selection, the cells were transferred 2 days after transfection into HT-free CHO-S-SFMII medium. In DHFR- and NPT-based selection in the event of co-transfection, in which one expression vector contained a DHFR and the other expression vector contained an NPT selectable marker, the cells were transferred 2 days after transfection into CHO-S-SFMII medium without the addition of hypoxanthine and thymidine and also G418 (Invitrogen) was added to the medium in a concentration of 400 µg/mL.

A DHFR-based gene amplification of the integrated heterologous genes can be obtained by the addition of the selecting agent MTX (Sigma, Deisenhofen, DE) in a concentration of 5-2000 nM to an HT-free CHO-S-SFMII medium.

Expression Vectors

To analyse the expression, eukaryotic expression vectors were used which are based on the pAD-CMV vector (Werner et al., 1998) and mediate the expression of a heterologous gene by the combination of CMV enhancer/hamster ubiquitin/S27a promoter (WO 97/15664) or CMV enhancer/CMV promoter. While the base vector pBID contains the dhfr-minigene which acts as an amplifiable selectable marker (cf e.g. EP-0-393-438), in the vector pBING the dhfr-minigene has been replaced by a modified NPT gene. This is the NPT variant D227G (Asp227Gly). The cloning of pBING with the NPT variant D227G and the IRES-GFP gene region was carried out as described in (WO2004/050884). The base plasmid pTE4 contains the NPT variant F240I (Phe240Ile) as selectable marker and is a derivative of the plasmid pBING. Apart from the replacement of the NPT variant D227G by the NPT variant F240I the GFP was also replaced by the red fluorescent protein DsRed2 from the vector pDsRed2 (Clontech, Palo Alto, Calif., USA). The base plasmid pTE5 contains DHFR as selectable marker and is a derivative of the vector pBIDG (WO2004/050884), in which again the GFP has been replaced by the red fluorescent protein DsRed2 from the vector pDsRed2 (Clontech, Palo Alto, Calif., USA).

In order to express a monoclonal humanised IgG1 antibody the heavy chain was cloned as a 1.4 kb SalI/SpeI fragment into the plasmid pBID digested with XbaI and SalI, to obtain the plasmid pBID-HC (FIG. 1A). The light chain on the other hand was cloned as a 0.7 kb BamHI/HindIII fragment into the cutting sites of the plasmid pBING, producing the plasmid pBING-LC (FIG. 1A).

Human MCP-1 cDNA (Yoshimura et al., 1989) was cloned into the corresponding cutting sites of the vector pTE4 or pTE5 as a 0.3 kb HindIII/EcoRI fragment, resulting in the plasmids pTE4/MCP-1 and pTE5/MCP-1 (FIG. 1B and FIG. 2 respectively).

FACS (Fluorescence-Activated Cell Sorter)

The flow-cytometric analyses were carried out with a BD FACSCalibur (BD Bioscience). The FACS is fitted with a helium-argon laser with an excitation wavelength of 488 nm.

The fluorescence intensity is absorbed at a wavelength suited to the particular fluorescence protein and processed by means of the attached software Cell Quest Pro.

ELISA (Enzyme-Linked Immunosorbant Assay)

The MCP-1 titres in supernatants of stably or transiently transfected CHO-DG44 cells were quantified by ELISA using the OptEIA Human MCP-1 Set kit in accordance with the manufacturer's instructions (BD Biosciences Pharmingen, Heidelberg, DE).

The IgG1 mAb in the supernatants from stably transfected CHO-DG44 cells was quantified by ELISA according to standard procedures (Current Protocols in Molecular Biology, Ausubel et al., 1994, updated), using on the one hand a goat anti human IgG Fc fragment (Dianova, Hamburg, DE) and on the other hand an AP-conjugated goat anti human kappa light chain antibody (Sigma). Purified IgG1 antibody was used as the standard.

Productivities (pg/cell/day) were calculated by the formula $pg/((Ct-Co)t/\ln(Ct-Co))$, where Co and Ct are the cell count on seeding and harvest, respectively, and t is the cultivation time.

SEAP Assay

The SEAP titre in culture supernatants from transiently transfected CHO-DG44 cells was quantified using the SEAP reporter gene assays in accordance with the manufacturer's instructions (Roche Diagnostics GmbH, Mannheim, DE).

Example 1: Isolation and Cloning of the TE Element TE-A

Starting from the sequence from the hamster genome described in WO97/15664, which comprises, in addition to the coding region for the ubiquitin/S27a gene, adjacent 5'UTR regions including the Ub/S27a-promoter, hitherto unknown sequence regions were isolated further upstream. For this, adapter-ligated genomic CHO-DG44 DNA was used as the matrix for "nested PCRs". The first PCR was carried out with a combination of primers with complementarity to the adapter or to a hamster sequence in the 5' region of the sequence listed in WO97/15664 under SEQ ID No. 5 (primer Ub20: 5'-CTCCACACATTTACACATGGACAC-3' (SEQ ID No. 39)); corresponds to nucleotides 62 to 85 (complementary sequence) of SEQ ID No. 5 from WO 97/15664). Then a second PCR was carried out with a second primer combination, consisting of an inner adapter primer and an inner ("nested") hamster-specific primer (primer Ub21: 5'-GGGTTTCTCTGTGTAATAGCCATG-3' (SEQ ID No. 40); corresponds to nucleotides 16 to 39 (complementary sequence) of SEQ ID No. 5 from WO97/15664). The resulting overlapping DNA fragments which started at the hamster-specific primer end with a known sequence and then merged into new unknown sequence regions located upstream were subcloned into pCR2.1 TOPO vectors (Invitrogen) and analysed by sequencing. In all 348 bp of a new, hitherto unknown sequence were obtained upstream of the hamster Ub/S27a gene.

On the basis of this new sequence information, another further upstream DNA region was isolated using the "nested PCR" described above. This time, the first PCR was carried out with an adapter primer and the primer Ub33 (5'-ATCT-CACTGTGTCTACCAACTTAG-3' (SEQ ID No. 41); situated in the 5' region of the newly isolated 384 bp sequence; corresponds to nucleotide 1268-1291 (complementary sequence) of SEQ ID No. 1) and the second PCR with an inner adapter primer and the hamster-specific primer Ub32a located further inwards (5'-TCTGCACCACCACTACCT-GACT-3' (SEQ ID No. 42); located upstream from the primer Ub33 within the newly isolated 384 bp sequence; corresponds to nucleotide 1243-1264 (complementary sequence) of SEQ ID No. 1). The amplified material obtained was subcloned into the pCR2.1 TOPO vector (Invitrogen) and sequenced. It contained another 1239 bp of a new, hitherto unknown sequence upstream from the hamster Ub/S27a-gene.

The sequence information from the overlapping PCR fragments was used to amplify a cohesive sequence region from the genomic DNA of CHO-DG44 by PCR, which comprised all the partial fragments hitherto isolated and extended 383 bp into the 5' sequence region of SEQ ID No. 5 from WO 97/15664, using the primers Ub34 (5'-CTAAGAGTACTTGCCATGAGAGCCTGAA-3' (SEQ ID No. 43); located at the outermost 5' end of the newly isolated 1239 bp sequence; only partially present in SEQ ID No. 1 (nucleotides 1 to 14))

and

Ub35 (5'-CATTGATACACCACCAAAGAACTTG-3' (SEQ ID No. 44); corresponds to nucleotides 1941 to 1965 (complementary sequence) of SEQ ID No. 1).

The resulting 2 kb DNA fragment was ligated with the 5' UTR region of sequence ID No. 5 described in WO 97/15664 via the endogenous EcoRI cutting site (position 353-358), although this cutting site was eliminated by a filling reaction with Klenow DNA polymerase. A second endogenous EcoRI cutting site in the newly isolated genome region was eliminated in the same way, resulting in the nucleotides 326 to 329 in SEQ ID No. 1 which are additional to the original genome sequence. In all, in this way, 8 additional nucleotides were inserted into SEQ ID No. 1 compared with the endogenous hamster sequence. The resulting 3788 bp DNA fragment from a sequence region located upstream from the hamster Ub/S27a gene was designated TE element A with the sequence ID No. 1 and subcloned into the vector pBluescript SKM (Stratagene, La Jolla, Calif.).

Example 2: Generation of Diverse TE Expression Vectors

Starting from the 3.8 kb TE-element TE-A (FIG. 3, Sequence ID No. 1) from the CHO genome various fragments were produced by PCR which had deletions at either the 5'- or 3'-end, compared with the TE element TE-A (FIG. 4 and FIG. 5). To synthesise these fragments combinations of direct and one reverse primer were used (FIG. 5 and FIG. 6). For cloning purposes a BamHI cutting site was attached at the 5'-end of the fragment and a BsrGI cutting site was attached at the 3'-end of the fragment by the primers. In this way 12 TE-elements of different lengths designated TE-01 to TE-12 were generated (FIGS. 4 and 5). After digestion with BsrGI and BamHI these were cloned in direct orientation into the adapter region of the base plasmids pTE4/MCP-1 (FIG. 1B) or pTE5/MCP-1 (FIG. 2).

The fragment TE-00 (SEQ ID No. 2) was isolated from a subclone of TE-A by SacII-restriction enzyme digestion and cloned into the base vectors pBING-LC (FIG. 1A) or pBID-HC (FIG. 1A) in both direct and reverse orientation via the SpeI cutting site located 5' of the promoter/enhancer element.

Sequences of the TE-Elements

TE-A (SEQUENCE ID NO. 1)
ccatgagagcctgaagacctgagttgatacccagaacccagatcaagatg gaggagagaaccagccccactaagctgtccctgaccccataaatgcct ccctgtccagttatgccacacaatgataggtgaatacagaaaaacaccct tcctttagacactaagcggattcctcttacgcataccagttaagtgatag ttcttaggcttcaactcagcacttttaaaaagtttatattttgcaatgctg gggactaaattaggggttgtgcacatgctaagtaagcactctactttttgta tcacattttaataattgtaagaattaattcgtgaaatagtagctgagaca atagatttgtttctttcatgtgggaactgctgtgtgtgcttcttgctgat gcaaacaaggtcaaatactttattccccagtgtctgcctagccctgtaac acctctctattatacaatgaccacaaataattaggtgagtgggttttgtt tcattttaaattgttgctattttagagacaggatttcttgcaaacctggt tggtcttaaactccgtatgtagctgagaatgaccttgaaaaccttcctgt cccaccctcaaattccagaattatagacacccaccacatggcttaataa gtaaacaacaacaataaaagcatgacttctgggtctggagggagggcttg ccagttaagagcaatggatactttcccatagaacctgggtttgactccca gcactaacctacatggtgatagtgatgcagcagacatacatgagggcaac acacacatgggcacatacacacgcacccgcccaccatggcttttcccca tcacttagacagccatatttaaacgtagtggagccaggctggggtggtgg cccacacctttaatcccagcactccagaaggcagaggtaggcggatctct gtgggtttgagaccagcctggtctacaagagctagttccaggacagcctc caaagccatagagaaaccctatctcaaaaaactgaaacaacaacaacaac aaaacaaaataaaaaaacaacaaaagaatcttagtggttcagtggttcca cacacaggaaagtagaaagggccttgatgggaaggttttcagagggagga gtatggatgagacaggatgatagtgaaaagaactcaaattaattaaatat ttgaaactatctaagaataaaagctaaaatatttaaaattacagtcaggt agtggtggtgcagagggctaagttggtagacacagtgagatccaggccag ccagggctacctagtgagaccttgttcaaataactaataaaatatacaaa ataaaggagacaccacaataattttgaaatgtaaaagactaaatttacct tttatattgatgagttggataaaaaaatcaatttaccagagaacataaag tagtcccatcaaagacaaaagcaatatatgattaaactctaatttaaaag tttgttagagcctggcaacgtggcacatacctttaatcccagcaccaggg agacagaggccatcctggtctaaaaagtgatctccaggacagccatggct attacacagagaaaccctgtctggaaaaacaaaaaattagtgtccatgtg taaatgtgtggagtatgcttgtcatgccacatacagaggtagagggcagt -continued ttatgggagtcagttcctattcttcctttatgggggacctggggactgaa ctcaggtcatcaggcttggcagaaagtgcattagctcacggagccttatc attggcgaaagctctctcaagtagaaaatcaatgtgtttgctcatagtgc aatcattatgtttcgagaggggaagggtacaatcgttggggcatgtgtgg tcacatctgaatagcagtagctccctaggagaattaattccaagttcttt ggtggtgtatcaatgcccttaaagggggtcaacaacttttttttccctctga caaaactatcttcttatgtccttgtccctcatatttgaagtattttattc tttgcagtgttgaatatcaattctagcacctcagacatgttaggtaagta ccctacaactcaggttaactaatttaatttaactaatttaaccccaacac ttttctttgtttatccacatttgtggagtgtgtgtgtgtgtgtgtgtgt gtgtgtgtgtgtgtgtgtgtgtgtgtgtgtgtgtgtgtgcgcgcgcgc gcgcgctcggatcattctaccttttgtttaaaaaatgttagtccagggt ggggtgcactgtgaaagtctgagggtaacttgctggggtcagttctttcc actataggacagaactccaggtgtcaactctttactgacagaaccatcca aatagccctatctaattttagtttttttatttatttattttttgtttttcg agacagggtttctctgtggctttggaggctgtcctggaactagctcttgt agaccaggctggtctcgaactcagagatccacctgcctctgcctcctgag tgctgggattaaaggcatgcgccaccaacgcttggctctacctaattta aaagagattgtgtgtcacaagggtgtcatgtcgccctgcaaccacccccc ccccaaaaaaaaaaaaaaaaaaaacttcactgaagctgaagcacgatgatt tggttactctggctggccaatgagctctagggagtctcctgtcaaacaga atctcaacaggcgcagcagtcttttttaaagtggggttacaacacaggtt tttgcatatcaggcattttatctaagctatttcccagccaaaaatgtgta ttttggaggcagcagagctaatagattaaaatgagggaagagcccacaca ggttattaggaagataagcatcttctttatataaaacaaaaccaaaccaa actggaggaggtctacctttagggatggaagaaaagacatttagagggtg caatagaaagggcactgagtttgtgaggtggaggactgggagagggcgca accgctttaactgtcctgttttgcctatttttggggacagcacatgttc ctattttcccaggatgggcaatctccacgtccaaacttgcggtcgagga ctacagtcattttgcaggtttccttactgtatggcttttaaaacgtgcaa aggtgaccattaaccgtttcacgctggagggcacgtgcggctcagatgc ttcctctgactgagggccaggagggggctacacggaagaggccacacccg cacttgggaagactcgatagggcttcagctggctgagacgcccagcagg ctcctcggctacaccttcagccccgaatgccttccggcccataacccttc ccttctaggcatttccggcgaggacccaccctcgcgccaaacattcggcc ccatcccccggtcctcacctgaatctctaactctgactccagagtttaga gactataaccagatagcccggatgtgtggaactgcatcttgggacgagta gttttagcaaaaagaaagcgacgaaaaactacaattcccagacagacttg tgttacctctcttctcatgctaaacaagccccctttaaaggaaagcccct cttagtcgcatcgactgtgtaagaaaggcgtttgaaacattttaatgttg ggcacaccgtttcgaggaccgaaatgagaaagagcatagggaaacggagc gcccgagctagtctggcactgcgttagacagccgcgg

TE ELEMENT 00

(SEQUENCE ID NO. 2)

gatctccaggacagccatggctattacacagagaaaccctgtctggaaaa acaaaaaattagtgtccatgtgtaaatgtgtggagtatgcttgtcatgcc acatacagaggtagagggcagtttatgggagtcagttcctattcttcctt tatggggacctggggactgaactcaggtcatcaggcttggcagaaagtg cattagctcacggagccttatcattggcgaaagctctctcaagtagaaaa tcaatgtgtttgctcatagtgcaatcattatgtttcgagaggggaagggt acaatcgttggggcatgtgtggtcacatctgaatagcagtagctccctag gagaattaattccaagttctttggtggtgtatcaatgcccttaaaggggt caacaacttttttccctctgacaaaactatcttcttatgtccttgtccc tcatatttgaagtatttattctttgcagtgttgaatatcaattctagca cctcagacatgttaggtaagtaccctacaactcaggttaactaatttaat ttaactaatttaaccccaacacttttcttgtttatccacatttgtgga gtgtgtgtgtgtgtgtgtgtgtgtgtgtgtgtgtgtgtgtgtgtgtgt gtgtgtgtgtgcgcgcgcgcgcgcgctcggatcattctaccttttgtt taaaaatgttagtccaggggtggggtgcactgtgaaagtctgagggtaa cttgctgggtcagttcttccactataggacagaactccaggtgtcaac tctttactgacagaaccatccaaatagccctatctaattttagtttttta tttatttattttttgtttttcgagacagggtttctctgtggctttggagg ctgtcctggaactagctcttgtagaccaggctggtctcgaactcagagat ccacctgcctctgcctcctgagtgctgggattaaaggcatgcgccaccaa cgcttggctctacctaattttaaaagagattgtgtgtcacaagggtgtca tgtcgccctgcaaccacccccccccaaaaaaaaaaaaaaaaaaaacttca ctgaagctgaagcacgatgatttggttactctggctggccaatgagctct agggagtctcctgtcaaacagaatctcaacaggcgcagcagtcttttta aagtgggggttacaacacaggttttgcatatcaggcatttatctaagct atttcccagccaaaaatgtgtattttggaggcagcagagctaatagatta aaatgagggaagagcccacacaggttattaggaagataagcatcttcttt atataaaacaaaaccaaaccaaactggaggaggtctaccttagggatgg aagaaaagacatttagagggtgcaatagaaagggcactgagtttgtgagg tggaggactgggagagggcgcaaccgctttaactgtcctgttttgcctat ttttggggacagcacatgttcctattttcccaggatgggcaatctcca cgtccaaacttgcggtcgaggactacagtcattttgcaggttttccttact gtatggcttttaaaacgtgcaaaggtgaccattaaccgtttcacgctggg agggcacgtgcggctcagatgcttcctctgactgagggccaggagggggc tacacggaagaggccacacccgcacttgggaagactcgatttgggcttca gctggctgagacgcccagcaggctcctcggctacaccttcagccccgaa tgccttccggcccataaccctcccttctaggcatttccggcgaggaccc accctcgcgccaaacattcggccccatcccccggtcctcacctgaatctc taactctgactccagagtttagagactataaccagatagcccggatgtgt ggaactgcatcttgggacgagtagttttagcaaaaagaaagcgacgaaaa actacaattcccagacagacttgtgttacctctcttctcatgctaaacaa gccccctttaaaggaaagcccctcttagtcgcatcgactgtgtaagaaag gcgtttgaaacattttaatgttgggcacaccgtttcgaggaccgaaatga gaaagagcatagggaaacggagcgcccgagctagtctggcactgcgttag acagccgcgg

TE ELEMENT 01

(SEQUENCE ID NO. 3)

gttgctatttagagacaggattcttgcaaacctggttggtcttaaact ccgtatgtagctgagaatgaccttgaaaaccttcctgtcccacccctcaa attccagaattatagacacccaccacatggcttaataagtaaacaacaac aataaaagcatgacttctgggtctggagggagggcttgccagttaagagc aatggatactttcccatagaacctgggtttgactcccagcactaacctac atggtgatagtgatgcagcagacatacatgagggcaacacacacatgggc acatacacgcacccgcccaccatggcttttccccccatcacttagacag ccatatttaaacgtagtggagccaggctggggtggtggcccacacccttta atcccagcactccagaaggcagaggtaggcggatctctgtgggtttgaga ccagcctggtctacaagagctagttccaggacagcctccaaagccataga gaaaccctatctcaaaaaactgaaacaacaacaacaacaaaacaaaataa aaaaacaacaaaagaatcttagtggttcagtggttccacacacaggaaag tagaaagggccttgatgggaaggttttcagagggaggagtatggatgaga caggatgatagtgaaaagaactcaaattaattaaatatttgaaactatct aagaataaaagctaaaatatttaaaattacagtcaggtagtggtggtgca gagggctaagttggtagacacagtgagatccaggccagccagggctacct agtgagaccttgttcaaataactaataaaatatacaaaataaaggagaca ccacaataattttgaaatgtaaaagactaaatttacctttatattgatg agttggataaaaaaatcaatttaccagagaacataaagtagtcccatcaa agacaaaagcaatatatgattaaactctaatttaaaagtttgttagagcc tggcaacgtggcacatacctttaatcccagcaccagggagacagaggcca tcctggtctaaaaagtgatctccaggacagccatggctattacacagaga aaccctgtctggaaaaacaaaaaattagtgtccatgtgtaaatgtgtgga gtatgcttgtcatgccacatacagaggtagagggcagtttatgggagtca gttcctattcttcctttatggggacctggggactgaactcaggtcatca ggcttggcagaaagtgcattagctcacggagccttatcattggcgaaagc tctctcaagtagaaaatcaatgtgtttgctcatagtgcaatcattatgtt tcgagaggggaagggtacaatcgttggggcatgtgtggtcacatctgaat agcagtagctccctaggagaattaattccaagttctttggtggtgtatca atgcccttaaaggggtcaacaacttttttccctctgacaaaactatctt cttatgtccttgtccctcatatttgaagtatttattctttgcagtgttg aatatcaattctagcacctcagacatgttaggtaagtaccctacaactca ggttaactaatttaatttaactaatttaaccccaacacttttcttgttt

```
atccacatttgtggagtgtgtgtgtgtgtgtgtgtgtgtgtgtgtg tgtgtgtgtgtgtgtgtgtgtgtgcgcgcgcgcgcgctcggatc attctacctttgtttaaaaaatgttagtccaggggtggggtgcactgtg aaagtctgagggtaacttgctggggtcagttctttccactataggacaga actccaggtgtcaactctttactgacagaaccatccaaatagccctatct aattttagtttttatttattttattttttgtttttcgagacagggtttct ctgtggctttggaggctgtcctggaactagctcttgtagaccaggctggt ctcgaactcagagatccacctgcctctgcctcctgagtgctgggattaaa ggcatgcgccaccaacgcttggctctacctaattttaaaagagattgtgt gtcacaagggtgtcatgtcgccctgcaaccaccccccccaaaaaaaaa aaaaaaaaaacttcactgaagctgaagcacgatgatttggttactctggc tggccaatgagctctagggagtctcctgtcaaacagaatctcaacaggcg cagcagtcttttttaaagtggggttacaacacaggttttttgcatatcagg cattttatctaagctatttcccagccaaaaatgtgtattttggaggcagc agagctaatagattaaaatgagggaagagcccacacaggttattaggaag ataagcatcttcttatataaaacaaaaccaaaccaaactggaggaggtc tacctttagggatggaagaaaagacatttagagggtgcaatagaaagggc actgagtttgtgaggtggaggactgggagagggcgcaaccgctttaactg tcctgttttgcctattttttggggacagcacatgttcctattttttcccag gatgggcaatctccacgtccaaacttgcggtcgaggactacagtcatttt gcaggtttccttactgtatggcttttaaaacgtgcaaaggtgaccattaa ccgtttcacgctgggagggcacgtgcggctcagatgcttcctctgactga gggccaggaggggctacacggaagaggccacacccgcacttgggaagac tcgatttgggcttcagctggctgagacgccccagcaggctcctcggctac accttcagccccgaatgccttccggcccataacccttcccttctaggcat ttccggcgaggacccaccctcgcgccaaacattcggccccatccccggt cctcacctgaatctctaactctgactccagagtttagagactataaccag atag

TE ELEMENT 02

(SEQUENCE ID NO. 4)
caaagccatagagaaaccctatctcaaaaaactgaaacaacaacaacaac aaaacaaaataaaaaaacaacaaaagaatcttagtggttcagtggttcca cacacaggaaagtagaaagggccttgatgggaaggttttcagaggggagga gtatggatgagacaggatgatagtgaaaagaactcaaattaattaaaatat ttgaaactatctaagaataaaagctaaaatatttaaaattacagtcaggt agtggtggtgcagagggctaagttggtagacacagtgagatccaggccag ccagggctacctagtgagaccttgacaaataactaataaaatatacaaaa taaaggagacaccacaataattttgaaatgtaaaagactaaatttaccttt ttatattgatgagaggtaaaaaaatcaatttaccagagaacataaagta gtcccatcaaagacaaaagcaatatatgattaaactctaattttaaaagtt tgttagagcctggcaacgtggcacataccttttaatcccagcaccaggag acagaggccatcctggtctaaaaagtgatctccaggacagccatggctat
```

```
tacacagagaaaccctgtctggaaaaacaaaaaattagtgtccatgtgta aatgtgtggagtatgcttgtcatgccacatacagaggtagagggcagttt atgggagtcagttcctattcttcctttatgggggacctggggactgaact caggtcatcaggcttggcagaaagtgcattagctcacggagccttatcat tggcgaaagctctctcaagtagaaaatcaatgtgtttgctcatagtgcaa tcattatgtttcgagaggggaagggtacaatcgttgggcatgtgtggtc acatctgaatagcagtagctccctaggagaattaattccaagttctttgg tggtgtatcaatgcccttaaaggggtcaacaacttttttttccctctgaca aaactatcttcttatgtccttgtccctcatatttgaagtattttattctt tgcagtgttgaatatcaattctagcacctcagacatgttaggtaagtacc ctacaactcaggttaactaatttaatttaactaatttaaccccaacactt tttctttgtttatccacatttgtggagtgtgtgtgtgtgtgtgtgtgtgt gtgtgtgtgtgtgtgtgtgtgtgtgtgtgtgtgtgtgcgcgcgcgc gcgctcggatcattctacctttttgtttaaaaaatgttagtccaggggtgg ggtgcactgtgaaagtctgagggtaacttgctggggtcagttctttccac tataggacagaactccaggtgtcaactctttactgacagaaccatccaaa tagccctatctaattttagttttttatttattttttgttttttcgag acagggtttctctgtggctttggaggctgtcctggaactagctcttgtag accaggctggtctcgaactcagagatccacctgcctctgcctcctgagtg ctgggattaaaggcatgcgccaccaacgcttggctctacctaattttaaa agagattgtgtgtcacaagggtgtcatgtcgccctgcaaccaccccccc ccaaaaaaaaaaaaaaaaaaacttcactgaagctgaagcacgatgatttg gttactctggctggccaatgagctctagggagtctcctgtcaaacagaat ctcaacaggcgcagcagtcttttttaaagtggggttacaacacaggtttt tgcatatcaggcattttatctaagctatttcccagccaaaaatgtgtatt ttggaggcagcagagctaatagattaaaatgagggaagagcccacacagg ttattaggaagataagcatcttctttatataaaacaaaaccaaaccaaac tggaggaggtctacctttagggatggaagaaaagacatttagagggtgca atagaaagggcactgagtttgtgaggtggaggactgggagagggcgcaac cgctttaactgtcctgttttgcctattttttggggacagcacatgttcct attttttcccaggatgggcaatctccacgtccaaacttgcggtcgaggact acagtcattttgcaggtttccttactgtatggcttttaaaacgtgcaaag gtgaccattaaccgtttcacgctgggagggcacgtgcggctcagatgctt cctctgactgagggccaggaggggctacacggaagaggccacacccgca cttgggaagactcgatttgggcttcagctggctgagacgccccagcaggc tcctcggctacaccttcagccccgaatgccttccggcccataacccttcc cttctaggcatttccggcgaggacccaccctcgcgccaaacattcggccc catccccggtcctcacctgaatctctaactctgactccagagtttagag actataaccagatag
```

TE ELEMENT 03

(SEQUENCE ID NO. 5)

```
acctttaatcccagcaccagggagacagaggccatcctggtctaaaagt
gatctccaggacagccatggctattacacagagaaaccctgtctggaaaa
acaaaaaattagtgtccatgtgtaaatgtgtggagtatgcttgtcatgcc
acatacagaggtagagggcagtttatggggagtcagttcctattcttcctt
tatggggggacctggggactgaactcaggtcatcaggcttggcagaaagtg
cattagctcacggagccttatcattggcgaaagctctctcaagtagaaaa
tcaatgtgtttgctcatagtgcaatcattatgtttcgagaggggaagggt
acaatcgttgggcatgtgtggtcacatctgaatagcagtagctccctag
gagaattaattccaagttctttggtggtgtatcaatgcccttaaagggt
caacaacttttttttccctctgacaaaactatcttcttatgtccttgtccc
tcatatttgaagtattttattctttgcagtgttgaatatcaattctagca
cctcagacatgttaggtaagtaccctacaactcaggttaactaatttaat
ttaactaatttaaccccaacactttttctttgtttatccacatttgtgga
gtgtgtgtgtgtgtgtgtgtgtgtgtgtgtgtgtgtgtgtgtgtgtgt
gtgtgtgtgtgcgcgcgcgcgcgctcggatcattctacctttttgtt
taaaaaatgttagtccaggggtggggtgcactgtgaaagtctgagggtaa
cttgctggggtcagttctttccactataggacagaactccaggtgtcaac
tctttactgacagaaccatccaaatagccctatctaattttagtttttta
tttatttattttttgttttttcgagacagggtttctctgtggctttggagg
ctgtcctggaactagctcttgtagaccaggctggtctcgaactcagagat
ccacctgcctctgcctcctgagtgctgggattaaaggcatgcgccaccaa
cgcttggctctacctaattttaaaagagattgtgtgtcacaagggtgtca
tgtcgccctgcaaccaccccccccaaaaaaaaaaaaaaaaaaacttca
ctgaagctgaagcacgatgatttggttactctggctggccaatgagctct
agggagtctcctgtcaaacagaatctcaacaggcgcagcagtcttttttta
aagtgggggttacaacacaggttttgcatatcaggcattttatctaagct
atttcccagccaaaaatgtgtattttggaggcagcagagctaatagatta
aaatgagggaagagcccacacaggttattaggaagataagcatcttcttt
atataaaacaaaaccaaaccaaactggaggaggtctacctttagggatgg
aagaaaagacatttagagggtgcaatagaaagggcactgagtttgtgagg
tggaggactgggagagggcgcaaccgctttaactgtcctgttttgcctat
tttttggggacagcacatgttcctattttccccaggatgggcaatctcca
cgtccaaacttgcggtcgaggactacagtcattttgcaggtttccttact
gtatggcttttaaaacgtgcaaaggtgaccattaaccgtttcacgctggg
agggcacgtgcggctcagatgcttcctctgactgagggccaggagggggc
tacacggaagaggccacacccgcacttgggaagactcgatttgggcttca
gctggctgagacgcccagcaggctcctcggctacaccttcagccccgaa
tgccttccggcccataaccctttcccttctaggcatttccggcgaggaccc
accctcgcgccaaacattcggccccatccccggtcctcacctgaatctc
taactctgactccagagtttagagactataaccagatag
```

TE ELEMENT 04

(SEQUENCE ID NO. 6)

```
ctatcttcttatgtccttgtccctcatatttgaagtattttattctttgc
agtgttgaatatcaattctagcacctcagacatgttaggtaagtaccctta
caactcaggttaactaatttaatttaactaatttaaccccaacactttttt
ctttgtttatccacatttgtggagtgtgtgtgtgtgtgtgtgtgtgtgtg
tgtgtgtgtgtgtgtgtgtgtgtgtgtgtgtgtgtgcgcgcgcgcgcg
ctcggatcattctacctttttgtttaaaaaatgttagtccaggggtgggt
gcactgtgaaagtctgagggtaacttgctggggtcagttctttccactat
aggacagaactccaggtgtcaactctttactgacagaaccatccaaatag
ccctatctaattttagttttttatttatttatttttttgttttttcgagaca
gggtttctctgtggctttggaggctgtcctggaactagctcttgtagacc
aggctggtctcgaactcagagatccacctgcctctgcctcctgagtgctg
ggattaaaggcatgcgccaccaacgcttggctctacctaattttaaaaga
gattgtgtgtcacaagggtgtcatgtcgccctgcaaccaccccccccca
aaaaaaaaaaaaaaaacttcactgaagctgaagcacgatgatttggtt
actctggctggccaatgagctctagggagtctcctgtcaaacagaatctc
aacaggcgcagcagtcttttttaaagtgggggttacaacacaggttttgc
atatcaggcattttatctaagctatttcccagccaaaaatgtgtatttg
gaggcagcagagctaatagattaaaatgagggaagagcccacacaggtta
ttaggaagataagcatcttctttatataaaacaaaaccaaaccaaactgg
aggaggtctacccttagggatggaagaaaagacatttagagggtgcaata
gaaagggcactgagtttgtgaggtggaggactgggagagggcgcaaccgc
tttaactgtcctgttttgcctattttttggggacagcacatgttcctatt
ttcccaggatgggcaatctccacgtccaaacttgcggtcgaggactaca
gtcattttgcaggtttccttactgtatggcttttaaaacgtgcaaaggtg
accattaaccgtttcacgctgggagggcacgtgcggctcagatgcttcct
ctgactgagggccaggagggggctacacggaagaggccacacccgcactt
gggaagactcgatttgggcttcagctggctgagacgcccagcaggctcc
tcggctacaccttcagccccgaatgccttccggcccataaccctttcccttt
ctaggcatttccggcgaggacccaccctcgcgccaaacattcggcccat
cccccggtcctcacctgaatctctaactctgactccagagtttagagact
ataaccagatag
```

TE ELEMENT 05

(SEQUENCE ID NO. 7)

```
caggctggtctcgaactcagagatccacctgcctctgcctcctgagtgct
gggattaaaggcatgcgccaccaacgcttggctctacctaattttaaaag
agattgtgtgtcacaagggtgtcatgtcgccctgcaaccaccccccccc
aaaaaaaaaaaaaaaaaacttcactgaagctgaagcacgatgatttggt
tactctggctggccaatgagctctagggagtctcctgtcaaacagaatct
caacaggcgcagcagtcttttttaaagtgggggttacaacacaggttttgc
catatcaggcattttatctaagctatttcccagccaaaaatgtgtatttt
ggaggcagcagagctaatagattaaaatgagggaagagcccacacaggtt
```

-continued
attaggaagataagcatcttctttatataaaacaaaaccaaaccaaactg
gaggaggtctacctttagggatggaagaaaagacatttagagggtgcaat
agaaagggcactgagtttgtgaggtggaggactgggagagggcgcaaccg
ctttaactgtcctgttttgcctattttttggggacagcacatgttcctat
ttttcccaggatgggcaatctccacgtccaaacttgcggtcgaggactac
agtcattttgcaggtttccttactgtatggcttttaaaacgtgcaaaggt
gaccattaaccgtttcacgctgggagggcacgtgcggctcagatgcttcc
tctgactgagggccaggaggggggctacacggaagaggccacaccccgcact
tgggaagactcgatttgggcttcagctggctgagacgccccagcaggctc
ctcggctacaccttcagccccgaatgccttccggcccataaccctccct
tctaggcatttccggcgaggacccacccctcgcgcaaacattcggcccca
tcccccggtcctcacctgaatctctaactctgactccagagtttagagac
tataaccagatag TE ELEMENT 06
(SEQUENCE ID NO. 8)
Cttgcggtcgaggactacagtcattttgcaggtttccttactgtatggct
tttaaaacgtgcaaaggtgaccattaaccgtttcacgctgggagggcacg
tgcggctcagatgcttcctctgactgagggccaggaggggggctacacgga
agaggccacaccccgcacttgggaagactcgatttgggcttcagctggctg
agacgccccagcaggctcctcggctacaccttcagccccgaatgccttcc
ggcccataaccctccttctaggcatttccggcgaggacccacccctcgc
gccaaacattcggccccatcccccggtcctcacctgaatctctaactctg
actccagagtttagcgactataaccagatag TE ELEMENT 07
(SEQUENCE ID NO. 9)
Gcctgaagacctgagttgatacccagaacccagatcaagatggaggagag
aaccagccccactaagctgtccctgaccccataaatgcctccctgtcc
agttatgccacacaatgataggtgaatacagaaaaacacccttcctttag
acactaagcggattcctcttacgcataccagttaagtgatagttcttagg
cttcaactcagcacttaaaaagtttatattttgcaatgctggggactaa
attagggttgtgcacatgctaagtaagcactctacttttgtatcacattt
taataattgtaagaattaattcgtgaaatagtagctgagacaatagattt
gtttctttcatgtgggaactgctgtgtgtgcttcttgctgatgcaaacaa
ggtcaaatactttattcccagtgtctgcctagccctgtaacacttctct
attatacaatgaccacaaataattaggtgagtgggttttgtttcattta
aattgttgctattttagagacaggatttc TE ELEMENT 08
(SEQUENCE ID NO. 10)
Gcctgaagacctgagttgatacccagaacccagatcaagatggaggagag
aaccagccccactaagctgtccctgaccccataaatgcctccctgtcc
agttatgccacacaatgataggtgaatacagaaaaacacccttcctttag
acactaagcggattcctcttacgcataccagttaagtgatagttcttagg
cttcaactcagcacttaaaaagtttatattttgcaatgctggggactaa
attagggttgtgcacatgctaagtaagcactctacttttgtatcacattt -continued
taataattgtaagaattaattcgtgaaatagtagctgagacaatagattt
gtttctttcatgtgggaactgctgtgtgtgcttcttgctgatgcaaacaa
ggtcaaatactttattcccagtgtctgcctagccctgtaacacttctct
attatacaatgaccacaaataattaggtgagtgggttttgtttcattta
aattgttgctattttagagacaggatttcttgcaaacctggttggtctta
aactccgtatgtagctgagaatgaccttgaaaaccttcctgtcccacccc
tcaaattccagaattatagacacccaccacatggcttaataagtaaacaa
caacaataaaagcatgacttctgggtctggagggagggcttgccagttaa
gagcaatggatactttcccatagaacctgggtttgactcccagcactaac
ctacatggtgatagtgatgcagcagacatacatgagggcaacacacacat
gggcacatacacacgcacccgcccaccatggcttttcccccatcacttag
acagccatatttaaacgtagtggagccaggctggggtggtggcccacacc
tttaatcccagcactccagaaggcagaggtaggcggatctctgtgggttt
gagaccagcctggtctacaagagctagttccaggacagcctccaaagcca
tagagaaaccctatc TE ELEMENT 09
(SEQUENCE ID NO. 11)
gcctgaagacctgagttgatacccagaacccagatcaagatggaggagag
aaccagccccactaagctgtccctgaccccataaatgcctccctgtcc
agttatgccacacaatgataggtgaatacagaaaaacacccttcctttag
acactaagcggattcctcttacgcataccagttaagtgatagttcttagg
cttcaactcagcacttaaaaagtttatattttgcaatgctggggactaa
attagggttgtgcacatgctaagtaagcactctacttttgtatcacattt
taataattgtaagaattaattcgtgaaatagtagctgagacaatagattt
gtttctttcatgtgggaactgctgtgtgtgcttcttgctgatgcaaacaa
ggtcaaatactttattcccagtgtctgcctagccctgtaacacttctct
attatacaatgaccacaaataattaggtgagtgggttttgtttcattta
aattgttgctattttagagacaggatttcttgcaaacctggttggtctta
aactccgtatgtagctgagaatgaccttgaaaaccttcctgtcccacccc
tcaaattccagaattatagacacccaccacatggcttaataagtaaacaa
caacaataaaagcatgacttctgggtctggagggagggcttgccagttaa
gagcaatggatactttcccatagaacctgggtttgactcccagcactaac
ctacatggtgatagtgatgcagcagacatacatgagggcaacacacacat
gggcacatacacacgcacccgcccaccatggcttttcccccatcacttag
acagccatatttaaacgtagtggagccaggctggggtggtggcccacacc
tttaatcccagcactccagaaggcagaggtaggcggatctctgtgggttt
gagaccagcctggtctacaagagctagttccaggacagcctccaaagcca
tagagaaaccctatctcaaaaaactgaaacaacaacaacaaaaacaaa
ataaaaaacaacaaaagaatcttagtggttcagtggttccacacacagg
aaagtagaaagggccttgatgggaaggttttcagagggaggagtatggat
gagacaggatgatagtgaaaagaactcaaattaattaaatatttgaaact
atctaagaataaaagctaaaatatttaaaattacagtcaggtagtggtgg -continued tgcagagggctaagttggtagacacagtgagatccaggccagccagggct acctagtgagaccttgttcaaataactaataaaatatacaaaataaagga gacaccacaataattttgaaatgtaaaagactaaatttaccttttatatt gatgagttggataaaaaaatcaatttaccagagaacataaagtagtccca tcaaagacaaaagcaatatatgattaaactctaatttaaaagtttgttag agcctggcaacgtggcatacctttaatcccagcaccagg

TE ELEMENT 10

(SEQUENCE ID NO. 12)

gcctgaagacctgagttgatacccagaacccagatcaagatggaggagag aaccagccccactaagctgtcccctgaccccataaatgcctccctgtcc agttatgccacacaatgataggtgaatacagaaaaacacccttcctttag acactaagcggattcctcttacgcataccagttaagtgatagttcttagg cttcaactcagcacttttaaaaagtttatattttgcaatgctggggactaa attagggttgtgcacatgctaagtaagcactctacttttgtatcacattt taataattgtaagaattaattcgtgaaatagtagctgagacaatagattt gtttctttcatgtgggaactgctgtgtgtgcttcttgctgatgcaaacaa ggtcaaatactttattccccagtgtctgcctagccctgtaacacttctct attatacaatgaccacaaataattaggtgagtgggttttgtttcatttta aattgttgctattttagagacaggatttcttgcaaacctggttggtctta aactccgtatgtagctgagaatgaccttgaaaaccttcctgtcccacccc tcaaattccagaattatagacacccaccacatggcttaataagtaaacaa caacaataaaagcatgacttctgggtctggagggagggcttgccagttaa gagcaatggatactttcccatagaacctgggtttgactcccagcactaac ctacatggtgatagtgatgcagcagacatacatgagggcaacacacacat gggcacatacacacgcacccgcccaccatggcttttcccccatcacttag acagccatatttaaacgtagtggagccaggctggggtggtggcccacacc cttaatcccagcactccagaaggcagaggtaggcggatctctgtgggttt gagaccagcctggtctacaagagctagttccaggacagcctccaaagcca tagagaaaccctatctcaaaaaactgaaacaacaacaacaacaaaacaaa ataaaaaaacaacaaaagaatcttagtggttcagtggttccacacacagg aaagtagaaagggccttgatgggaaggttttcagagggaggagtatggat gagacaggatgatagtgaaaagaactcaaattaattaaatatttgaaact atctaagaataaaagctaaatatttaaaattacagtcaggtagtggtgg tgcagagggctaagttggtagacacagtgagatccaggccagccagggct acctagtgagaccttgttcaaataactaataaaatatacaaaataaagga gacaccacaataattttgaaatgtaaaagactaaatttaccttttatatt gatgagttggataaaaaaatcaatttaccagagaacataaagtagtccca tcaaagacaaaagcaatatatgattaaactctaatttaaaagtttgttag agcctggcaacgtggcatacctttaatcccagcaccagggagacagag gccatcctggtctaaaagtgatctccaggacagccatggctattacaca gagaaaccctgtctggaaaaacaaaaaattagtgtccatgtgtaaatgtg tggagtatgcttgtcatgccacatacagaggtagagggcagtttatggga -continued gtcagttcctattcttcctttatgggggacctggggactgaactcaggtc atcaggcttggcagaaagtgcattagctcacggagccttatcattggcga aagctctctcaagtagaaaatcaatgtgtttgctcatagtgcaatcatta tgtttcgagaggggaagggtacaatcgttggggcatgtgtggtcacatct gaatagcagtagctccctaggagaattaattccaagttctttggtggtgt atcaatgcccttaaagggtcaacaactttttttccctctgacaaaacta tcttcttatgtccttgtccc

TE ELEMENT 11

(SEQUENCE ID NO. 13)

gcctgaagacctgagttgatacccagaacccagatcaagatggaggagag aaccagccccactaagctgtcccctgaccccataaatgcctccctgtcc agttatgccacacaatgataggtgaatacagaaaaacacccttcctttag acactaagcggattcctcttacgcataccagttaagtgatagttcttagg cttcaactcagcacttttaaaaagtttatattttgcaatgctggggactaa attagggttgtgcacatgctaagtaagcactctacttttgtatcacattt taataattgtaagaattaattcgtgaaatagtagctgagacaatagattt gtttctttcatgtgggaactgctgtgtgtgcttcttgctgatgcaaacaa ggtcaaatactttattccccagtgtctgcctagccctgtaacacttctct attatacaatgaccacaaataattaggtgagtgggttttgtttcatttta aattgttgctattttagagacaggatttcttgcaaacctggttggtctta aactccgtatgtagctgagaatgaccttgaaaaccttcctgtcccacccc tcaaattccagaattatagacacccaccacatggcttaataagtaaacaa caacaataaaagcatgacttctgggtctggagggagggcttgccagttaa gagcaatggatactttcccatagaacctgggtttgactcccagcactaac ctacatggtgatagtgatgcagcagacatacatgagggcaacacacacat gggcacatacacacgcacccgcccaccatggcttttcccccatcacttag acagccatatttaaacgtagtggagccaggctggggtggtggcccacacc tttaatcccagcactccagaaggcagaggtaggcggatctctgtgggttt gagaccagcctggtctacaagagctagttccaggacagcctccaaagcca tagagaaaccctatctcaaaaaactgaaacaacaacaacaacaaaacaaa ataaaaaaacaacaaaagaatcttagtggttcagtggttccacacacagg aaagtagaaagggccttgatgggaaggttttcagagggaggagtatggat gagacaggatgatagtgaaaagaactcaaattaattaaatatttgaaact atctaagaataaaagctaaatatttaaaattacagtcaggtagtggtgg tgcagagggctaagttggtagacacagtgagatccaggccagccagggct acctagtgagaccttgttcaaataactaataaaatatacaaaataaagga gacaccacaataattttgaaatgtaaaagactaaatttaccttttatatt gatgagttggataaaaaaatcaatttaccagagaacataaagtagtccca tcaaagacaaaagcaatatatgattaaactctaatttaaaagtttgttag agcctggcaacgtggcatacctttaatcccagcaccagggagacagag gccatcctggtctaaaagtgatctccaggacagccatggctattacaca gagaaaccctgtctggaaaaacaaaaaattagtgtccatgtgtaaatgtg -continued tggagtatgcttgtcatgccacatacagaggtagagggcagtttatggga gtcagttcctattcttcctttatgggggacctggggactgaactcaggtc atcaggcttggcagaaagtgcattagctcacggagccttatcattggcga aagctctctcaagtagaaaatcaatgtgtttgctcatagtgcaatcatta tgtttcgagaggggaagggtacaatcgttggggcatgtgtggtcacatct gaatagcagtagctccctaggagaattaattccaagttctttggtggtgt atcaatgcccttaaaggggtcaacaactttttttccctctgacaaaacta tcttcttatgtccttgtccctcatatttgaagtattttattctttgcagt gttgaatatcaattctagcacctcagacatgttaggtaagtaccctacaa ctcaggttaactaatttaatttaactaatttaaccccaacacttttttctt tgtttatccacatttgtggagtgtgtgtgtgtgtgtgtgtgtgtgtgt gtgtgtgtgtgtgtgtgtgtgtgtgtgtgcgcgcgcgcgcgcgctc ggatcattctaccttttgtttaaaaaatgttagtccaggggtggggtgca ctgtgaaagtctgagggtaacttgctggggtcagttcttttccactatagg acagaactccaggtgtcaactctttactgacagaaccatccaaatagccc tatctaattttagttttttatttatttattttttgttttttcgagacaggg tttctctgtggctttggaggctgtcctggaactagctcttgtagaccagg ctggtctcgaactcag

TE ELEMENT 12

(SEQUENCE ID NO. 14)

gcctgaagacctgagttgatacccagaacccagatcaagatggaggagag aaccagccccactaagctgtcccctgaccccataaatgcctccctgtcc agttatgccacacaatgataggtgaatacagaaaaacacccttcctttag acactaagcggattcctcttacgcataccagttaagtgatagttcttagg cttcaactcagcacttttaaaaagtttatattttgcaatgctggggactaa attagggttgtgcacatgctaagtaagcactctacttttgtatcacattt taataattgtaagaattaattcgtgaaatagtagctgagacaatagattt gtttctttcatgtgggaactgctgtgtgtgcttcttgctgatgcaaacaa ggtcaaatactttattccccagtgtctgcctagccctgtaacacttctct attatacaatgaccacaaataattaggtgagtgggttttgtttcattta aattgttgctattttagagacaggatttcttgcaaacctggttggtctta aactccgtatgtagctgagaatgaccttgaaaaccttcctgtcccacccc tcaaattccagaattatagacacccaccacatggcttaataagtaaacaa caacaataaaagcatgacttctgggtctggagggagggcttgccagttaa gagcaatggatactttcccatagaacctgggtttgactcccagcactaac ctacatggtgatagtgatgcagcagacatacatgagggcaacacacacat gggcacatacacacgcacccgcccaccatggcttttcccccatcacttag acagccatatttaaacgtagtggagccaggctggggtggtggcccacacc tttaatcccagcactccagaaggcagaggtaggcggatctctgtgggttt gagaccagcctggtctacaagagctagttccaggacagcctccaaagcca tagagaaaccctatctcaaaaaactgaaacaacaacaacaacaaaacaaa ataaaaaaacaacaaaagaatcttagtggttcagtggttccacacacagg aaagtagaaagggccttgatgggaaggttttcagagggaggagtatggat gagacaggatgatagtgaaaagaactcaaattaattaaatatttgaaact atctaagaataaaagctaaaatatttaaaattacagtcaggtagtggtgg tgcagagggctaagttggtagacacagtgagatccaggccagccagggct acctagtgagaccttgttcaaataactaataaaatatacaaaataaagga gacaccacaataattttgaaatgtaaaagactaaatttacctttttatatt gatgagttggataaaaaaatcaatttaccagagaacataaagtagtccca tcaaagacaaaagcaatatatgattaaactctaatttaaaagtttgttag agcctggcaacgtggcacatacctttaatcccagcaccagggagacagag gccatcctggtctaaaaagtgatctccaggacagccatggctattacaca gagaaaccctgtctggaaaaacaaaaaattagtgtccatgtgtaaatgtg tggagtatgcttgtcatgccacatacagaggtagagggcagtttatggga gtcagttcctattcttcctttatgggggacctggggactgaactcaggtc atcaggcttggcagaaagtgcattagctcacggagccttatcattggcga aagctctctcaagtagaaaatcaatgtgtttgctcatagtgcaatcatta tgtttcgagaggggaagggtacaatcgttggggcatgtgtggtcacatct gaatagcagtagctccctaggagaattaattccaagttctttggtggtgt atcaatgcccttaaaggggtcaacaactttttttccctctgacaaaacta tcttcttatgtccttgtccctcatatttgaagtattttattctttgcagt gttgaatatcaattctagcacctcagacatgttaggtaagtaccctacaa ctcaggttaactaatttaatttaactaatttaaccccaacacttttttctt tgtttatccacatttgtggagtgtgtgtgtgtgtgtgtgtgtgtgtgtgt gtgtgtgtgtgtgtgtgtgtgtgtgtgtgtgcgcgcgcgcgcgcgctc ggatcattctaccttttgtttaaaaaatgttagtccaggggtggggtgca ctgtgaaagtctgagggtaacttgctggggtcagttcttttccactatagg acagaactccaggtgtcaactctttactgacagaaccatccaaatagccc tatctaattttagttttttatttatttattttttgttttttcgagacaggg tttctctgtggctttggaggctgtcctggaactagctcttgtagaccagg ctggtctcgaactcagagatccacctgcctctgcctcctgagtgctggga ttaaaggcatgcgccaccaacgcttggctctacctaattttaaaagagat tgtgtgtcacaagggtgtcatgtcgccctgcaaccacccccccccaaaa aaaaaaaaaaaaaaacttcactgaagctgaagcacgatgatttggttact ctggctggccaatgagctctagggagtctcctgtcaaacagaatctcaac aggcgcagcagtctttttttaaagtgggggttacaacacaggttttgcata tcaggcattttatctaagctatttcccagccaaaaatgtgtattttggag gcagcagagctaatagattaaaatgagggaagagcccacacaggttatta ggaagataagcatcttctttatataaaacaaaaccaaaccaaactggagg aggtctacctttagggatggaagaaaagacatttagagggtgcaatagaa agggcactgagtttgtgaggtggaggactgggagagggcgcaaccgcttt aactgtcctgttttgcctattttttgggggacagcacatgttcctattttt cccaggatgggcaatctccacgtccaaacttgcggtcgaggactacag

Example 3: Influence of the TE Element Variant TE-00 on the Expression of GFP and Immunoglobulin G1 (IgG1)

The effect of the TE element TE-00 on the expression of the cytoplasmically located GFPs (green fluorescent protein) and a secreted monoclonal IgG1-antibody was investigated in two independent stable transfection series with CHO-DG44 cells. For this, CHO-DG44 cells were co-transfected with the following plasmid combinations or plasmid variants:

control plasmids pBING-LC (FIG. 1A) and pBID-HC (FIG. 1A) without TE element pBING-LC and pBID-HC with a TE element TE-00 integrated upstream from the promoter/enhancer in direct orientation pBING-LC and pBID-HC with a TE element TE-00 integrated upstream from the promoter/enhancer in reverse orientation In transfection series A four pools were produced, in transfection series B ten pools were produced per variant. Equimolar amounts of the two plasmids were used. In order to arrive at the same total number of molecules, the total amount of DNA used in series A in the control mixtures was 1 µg, while in the mixtures containing TE element the amount was 1.3 µg. This difference resulted from the different plasmid sizes, as the plasmids with TE element were larger than the control plasmids by a factor of 1.3. As the amount of DNA used in the transfection mix can have an effect on transfection efficiency, in series B the total amount of DNA was balanced out with 300 ng of "mock DNA" (=vector without product gene, TE element and eukaryotic selectable marker), so that the mixture with the control plasmids also contained 1.3 µg DNA in total. As a negative control, a mock-transfected pool was also run in each transfection series, i.e. treated in the same way, but without the addition of DNA in the transfection mixture. The selection of stably transfected cells took place two days after the transfection with −HT/+G418 (400 µg/mL). After the selection the proportion of GFP-expressing cells was determined by FACS. The comparison of the variants in the plot overlay in both transfection series yielded a larger proportion of GFP-expressing cells for pools with TE element 00 than in pools with control plasmids (FIG. 7). Between the pools in which the TE element was present in the plasmid in either direct or reverse orientation, no differences of any kind could be found. The effect of the TE element 00, namely increasing the proportion of cells with higher productivity in a mixed population, was consequently independent of the orientation thereof.

In addition, the IgG1 titre and the specific productivity of the pools were determined over a period of six to eight passages (passaging rhythm 2-2-3 days). Here again it was confirmed that the cell pools containing the TE element 00 on average expressed more than the cell pools without TE element (FIG. 9, series A and B). In both series, a doubling of the pool productivity could be demonstrated as a result of the presence of the TE element, while the orientation in which the element was cloned in the expression plasmid was of no relevance.

Example 4: Influence of the TE Elements TE-01 to TE-12 on the Expression of MCP-1

The effect of the TE elements TE-01 to TE-12 on the expression of the secreted MCP-1 was investigated in three stable transfection series (Series C, D and E) of CHO-DG44 cells compared with expression without the TE element. In all three series, 6 pools were produced per plasmid variant. The base plasmid was pTE4/MCP-1 in Series C and D (FIG. 1B; Selectable Marker NPT—Neomycin-phosphotransferase F240I), pTE5/MCP-1 in Series E (FIG. 2; Selectable Marker DHFR=Dihydrofolate-reductase). These contained either no TE element (=control mixtures) or one of the TE elements TE-01 to TE-12 in direct orientation upstream of the promoter/enhancer. In order to minimise the influence on transfection efficiency caused by different amounts of DNA in the transfection mixture, 1.2 µg of plasmid-DNA were used in total. Depending on the size of the TE element introduced, the plasmid size varied between 6.7 kb and 10.7 kb. However, to ensure that the total number of molecule of test plasmids could be kept constant in all the mixtures, in the mixtures with smaller plasmid molecules the total amount of DNA was balanced out with a so-called mock plasmid which contained neither product gene and TE element nor any eukaryotic selectable marker. As a negative control, for each transfection series, a mock-transfected pool was also run, i.e. treated in the same way but without the addition of DNA to the transfection mixture. The selection of stably transfected cells was carried out two days after transfection, with HT-supplemented CHO-S-SFMII +G418 (400 µg/mL) in Series C and D and with HT-free CHO-S-SFMII in Series E.

After the selection, the proportion of dsRed2-expressing cells was determined by FACS. FIG. 8 shows the relative percentage fluorescence of the living transfected cells from Series C. Compared with the control pools, the pools which contained the TE elements TE-01, TE-02 or TE-08, contained about 3 to 3.5 times more dsRed2-expressing cells and pools with the element TE-06 contained approximately twice as many dsRed2-expressing cells. In pools with the fragments TE-05 and TE-09, on the other hand, there was no apparent increase in the proportion of dsRed2-expressing cells compared with the control.

In addition, the MCP-1 product titre and the specific productivity were also raised over a period of 6 passages (passaging rhythm 2-2-3 days). FIG. 9 (Series C and D) and FIG. 10 (Series E) shows a relative specific MCP-1 productivities. The element TE-08 in conjunction with NPT-F240I as selectable marker with factor 5.3 showed the greatest increase in the specific MCP-1 productivity compared with the control pools without TE element (FIG. 9). Combined with DHFR as selectable marker, a 6-fold increase was achieved with this variant (FIG. 10). The TE elements 01, 02 and 03 resulted in a 4 to 4.5-fold increase in productivity in the NPT-selected pools (FIG. 9) and a 2.6 to 6.8-fold increase in productivity in the DHFR-selected pools (FIG. 10) compared with the control pools. The TE element 06 which is only 300 bp long was also able to increase productivity in all the series by a factor 2.5 to 3.2 (FIGS. 9 and 10). The increases achieved with fragments TE-04 and TE-07 were also of this order of magnitude (FIG. 10). Pools in which the somewhat longer fragments TE-10, TE-11 and TE-12 were used, showed a doubling of MCP-1 expression (FIGS. 9 and 10). Obviously, in all these pools, the number of cells expressing little or no product was reduced and thus overall the proportion of high producers in the cell population was increased. This is an indication that the TE elements are able to suppress, shield or cancel out negative chromosomal positional effects.

By contrast, the expression could not be increased compared with the control by the use of fragments TE-05 and TE-09, as has already been seen with dsRed2-expression (FIG. 8), and in some cases was even less (FIGS. 9 and 10).

These elements, or partial fragments in these sequence regions, could possibly thus even have a repressing effect.

In all, the change in MCP-1 expression observed correlated with the proportion of dsRed2-expressing cells in the stable cell pools.

Example 5: Test of the TE Elements TE-01 to TE-12 on Enhancer Activity

By transient transfection of CHO-DG44 cells a test was carried out to see whether the observed increase in product expression is actually based on a chromatin-opening effect of the TE elements or whether it is based on an enhancer activity. As the plasmid is not integrated into the genome in transient transfection, the genetic information is read off directly from the plasmid. Thus, no chromosomal positional effects can occur. If nevertheless there are positive effects on gene expression these can be put down to enhancers present in the TE element. Such enhancers can act on the activity of a promoter in the cis location irrespective of position and orientation and stimulate the transcription of a functionally linked gene.

In the transient expression study shown in FIG. 11 6 pools were transfected with the base plasmid pTE4/MCP-1 (=control; FIG. 1B) or derivatives thereof, each additionally containing one of the TE elements TE-01 to TE-12 upstream of the promoter/enhancer. After 48 hours cultivation in a total volume of 3 mL harvesting and determination of the MCP-1 titre were carried out in the cell culture supernatant by ELISA. Differences in transfection efficiency were corrected by co-transfection with an SEAP expression plasmid (addition of 100 ng of plasmid DNA per transfection mixture) and subsequent measurement of the SEAP activity. FIG. 11 shows the average from the 6 parallel pools. The data show that the MCP-1 titre in the cell culture supernatant were very similar in all the pools and there were no significant differences in expression from the control plasmid pTE4/MCP-1 without a TE element. Thus the increase on productivity of more than factor 2 brought about by some TE elements in stably transfected cell pools is not based on the presence of an enhancer in the TE sequence. Thus for the enhanced expression obtained by TE elements chromosomal integration is absolutely essential.

Example 6: Production of Other TE Elements and Testing of Different TE Element Positions and Combinations Analogously to the method described in Example 2, other partial fragments of Sequence ID No. 1 or derivatives thereof can be generated and tested for their positive effect on productivity as described in Examples 3 and 5. Some Examples of possible fragments are shown in FIG. 12. The results obtained hitherto indicate for example that the regions of Sequence ID No. 1 shown in FIG. 12 could also bring about an increase in gene expression. In stable transfection series these new TE elements are to be characterised more closely with regard to their effect on specific productivity in order to locate and further narrow down the sequence regions which are important for the function. Narrowing down of the function to specific sequence regions and the associated possible reduction in the fragment length is advantageous for efficient use in expression vectors, as smaller expression plasmids are more stable and are easier to manipulate both during cloning and during transfection.

Furthermore, it is possible to arrange similar or different fragment regions in any orientation to one another and also in any position within the plasmid. The investigation as to which of the combinations results in the best possible increase in expression can also be carried out in stable transfection series. Some embodiments, which are in no way restrictive, are shown in FIG. 13. Thus, for example, the investigation should determine whether the TE elements TE-06 and TE-08 are able to bring about an additional increase in expression when they flank the product gene on both sides or are arranged one after another. Also, it is conceivable that the concatination of short TE elements, be they identical or different, such as TE element 06 and 08, for example, could also lead to an additional expression-enhancing effect.

Further TE Elements

TE-ELEMENT 13

(SEQUENCE ID NO. 15)

gttgctattttagagacaggatttcttgcaaacctggttggtcttaaact ccgtatgtagctgagaatgaccttgaaaaccttcctgtcccacccctcaa attccagaattatagacacccaccacatggcttaataagtaaacaacaac aataaaagcatgacttctgggtctggagggagggcttgccagttaagagc aatggatactttcccatagaacctgggtttgactcccagcactaacctac atggtgatagtgatgcagcagacatacatgagggcaacacacacatggc acatacacacgcacccgcccaccatggcttttcccccatcacttagacag ccatatttaaacgtagtggagccaggctggggtggtggcccacacctta atcccagcactccagaaggcagaggtaggcggatctctgtgggtttgaga ccagcctggtctacaagagctagttccaggacagcctccaaagccataga gaaaccctatc

TE-ELEMENT 14

(SEQUENCE ID NO. 16)

caaagccatagagaaaccctatctcaaaaaactgaaacaacaacaacaac aaaacaaaataaaaaaacaacaaaagaatcttagtggttcagtggttcca cacacaggaaagtagaaagggccttgatgggaaggttttcagagggagga gtatggatgagacaggatgatagtgaaaagaactcaaattaattaaatat ttgaaactatctaagaataaaagctaaaatatttaaaattacagtcaggt agtggtggtgcagagggctaagttggtagacacagtgagatccaggccag ccagggctacctagtgagaccttgttcaaataactaataaaatatacaaa ataaaggagacaccacaataattttgaaatgtaaaagactaaatttacct tttatattgatgagttggataaaaaaatcaatttaccagagaacataaag tagtcccatcaaagacaaaagcaatatatgattaaactctaatttaaaag tttgttagagcctggcaacgtggcacatacctttaatcccagcaccagg

TE-ELEMENT 15

(SEQUENCE ID NO. 17)

gttgctattttagagacaggatttcttgcaaacctggttggtcttaaact ccgtatgtagctgagaatgaccttgaaaaccttcctgtcccacccctcaa attccagaattatagacacccaccacatggcttaataagtaaacaacaac aataaaagcatgacttctgggtctggagggagggcttgccagttaagagc aatggatactttcccatagaacctgggtttgactcccagcactaacctac atggtgatagtgatgcagcagacatacatgagggcaacacacacatggc

```
acatacacacgcacccgcccaccatggcttttcccccatcacttagacag ccatatttaaacgtagtggagccaggctggggtggtggcccacacccttta atcccagcactccagaaggcagaggtaggcggatctctgtgggtttgaga ccagcctggtctacaagagctagttccaggacagcctccaaagccataga gaaaccctatctcaaaaaactgaaacaacaacaacaacaaaacaaaataa aaaaacaacaaaagaatcttagtggttcagtggttccacacacaggaaag tagaaagggccttgatgggaaggttttcagagggaggagtatggatgaga caggatgatagtgaaaagaactcaaattaattaaatatttgaaactatct aagaataaaagctaaaatatttaaaattacagtcaggtagtggtggtgca gagggctaagttggtagacacagtgagatccaggccagccagggctacct agtgagaccttgttcaaataactaataaaatatacaaaataaaggagaca ccacaataattttgaaatgtaaaagactaaatttaccttttatattgatg agttggataaaaaaatcaatttaccagagaacataaagtagtcccatcaa agacaaaagcaatatatgattaaactctaattttaaaagtttgttagagcc tggcaacgtggcacatacctttaatcccagcaccagg TE-ELEMENT 16
                              (SEQUENCE ID NO. 18)
acctttaatcccagcaccagggagacagaggccatcctggtctaaaaagt gatctccaggacagccatggctattacacagagaaaccctgtctggaaaa acaaaaaattagtgtccatgtgtaaatgtgtggagtatgcttgtcatgcc acatacagaggtagagggcagtttatgggagtcagacctattcttcctttt atggggacctggggactgaactcaggtcatcaggcttggcagaaagtgc attagctcacggagccttatcattggcgaaagctctctcaagtagaaaat caatgtgtttgctcatagtgcaatcattatgtttcgagaggggaagggta caatcgttggggcatgtgtggtcacatctgaatagcagtagctccctagg agaattaattccaagttctttggtggtgtatcaatgcccttaaagggtc aacaacttttttttccctctgacaaaactatcttcttatgtccttgtccc TE-ELEMENT 17
                              (SEQUENCE ID NO. 19)
caaagccatagagaaaccctatctcaaaaaactgaaacaacaacaacaac aaaacaaaataaaaaaacaacaaaagaatcttagtggttcagtggttcca cacacaggaaagtagaaagggccttgatgggaaggttttcagagggagga gtatggatgagacaggatgatagtgaaaagaactcaaattaattaaatat ttgaaactatctaagaataaaagctaaaatatttaaaattacagtcaggt agtggtggtgcagagggctaagttggtagacacagtgagatccaggccag ccagggctacctagtgagaccttgttcaaataactaataaaatatacaaa ataaaggagacaccacaataattttgaaatgtaaaagactaaatttacct tttatattgatgagttggataaaaaaatcaatttaccagagaacataaag tagtcccatcaaagacaaaagcaatatatgattaaactctaattttaaaag tttgttagagcctggcaacgtggcacatacctttaatcccagcaccaggg agacagaggccatcctggtctaaaaagtgatctccaggacagccatggct attacacagagaaaccctgtctggaaaaacaaaaaattagtgtccatgtg taaatgtgtggagtatgcttgtcatgccacatacagaggtagagggcagt ttatgggagtcagacctattcttcctttatggggacctggggactgaac tcaggtcatcaggcaggcttgaaagtgcattagctcacggagccttatca ttggcgaaagctctctcaagtagaaaatcaatgtgtttgctcatagtgca atcattatgtttcgagaggggaagggtacaatcgttggggcatgtgtggt cacatctgaatagcagtagctccctaggagaattaattccaagttctttg gtggtgtatcaatgcccttaaaggggtcaacaacttttttttccctctgac aaaactatcttcttatgtccttgtccc TE-ELEMENT 18
                              (SEQUENCE ID NO. 20)
gttgctattttagagacaggattcttgcaaacctggttggtcttaaact ccgtatgtagctgagaatgaccttgaaaaccttcctgtcccacccctcaa attccagaattatagacacccaccacatggcttaataagtaaacaacaac aataaaagcatgacttctgggtctggagggagggcttgccagttaagagc aatggatactttcccatagaacctgggtttgactcccagcactaacctac atggtgatagtgatgcagcagacatacatgagggcaacacacacatggc acatacacacgcacccgcccaccatggcttttcccccatcacttagacag ccatatttaaacgtagtggagccaggctggggtggtggcccacacccttta atcccagcactccagaaggcagaggtaggcggatctctgtgggtttgaga ccagcctggtctacaagagctagttccaggacagcctccaaagccataga gaaaccctatctcaaaaaactgaaacaacaacaacaacaaaacaaaataa aaaaacaacaaaagaatcttagtggttcagtggttccacacacaggaaag tagaaagggccttgatgggaaggttttcagagggaggagtatggatgaga caggatgatagtgaaaagaactcaaattaattaaatatttgaaactatct aagaataaaagctaaaatatttaaaattacagtcaggtagtggtggtgca gagggctaagttggtagacacagtgagatccaggccagccagggctacct agtgagaccttgttcaaataactaataaaatatacaaaataaaggagaca ccacaataattttgaaatgtaaaagactaaatttaccttttatattgatg agttggataaaaaaatcaatttaccagagaacataaagtagtcccatcaa agacaaaagcaatatatgattaaactctaattttaaaagtttgttagagcc tggcaacgtggcacatacctttaatcccagcaccagggagacagaggcca tcctggtctaaaaagtgatctccaggacagccatggctattacacagaga aaccctgtctggaaaaacaaaaaattagtgtccatgtgtaaatgtgtgga gtatgcttgtcatgccacatacagaggtagagggcagtttatgggagtca gttcctattcttcctttatggggacctggggactgaactcaggtcatca ggcttggcagaaagtgcattagctcacggagccttatcattggcgaaagc tctctcaagtagaaaatcaatgtgtttgctcatagtgcaatcattatgtt tcgagaggggaagggtacaatcgttggggcatgtgtggtcacatctgaat agcagtagctccctaggagaattaattccaagttctttggtggtgtatca atgcccttaaaggggtcaacaacttttttttccctctgacaaaactatctt cttatgtccttgtccc TE-ELEMENT 21
                              (SEQUENCE ID NO. 21)
cttgcggtcgaggactacagtcattttgcaggtttccttactgtatggct
```

-continued

```
tttaaaacgtgcaaaggtgaccattaaccgtttcacgctgggagggcacg tgcggctcagatgcttcctctgactgagggccaggagggggctacacgga agaggccacaccccgcacttgggaagactcgatttgggcttcagctggctg agacgcccagcaggctcctcggctacaccttcagccccgaatgccttcc ggcccataaccct tcccttctaggcatttccggcgaggacccaccctcgc gccaaacattcggccccatcccccggtcctcacctgaatctctaactctg actccagagtttagagactataaccagatag
```

Example 7: Influence of TE Elements RE-13 to TE-18 on the Expression of MCP-1

The effect of the TE elements TE-13 to TE-18 on the expression of the secreted MCP-1 was investigated in a stable transfection series (Series F) of CHO-DG44 cells by comparison with expression without the TE element. Four pools were produced per plasmid variant. The base plasmid was pTE4/MCP-1 in all the series (FIG. 1B; Selectable Marker NPT—Neomycin-phosphotransferase F240I). The various plasmid variants contained either no TE element (=control mixtures) or one of TE elements TE-13 to TE-18 in direct orientation upstream from the promoter/enhancer (FIG. 12). In order to minimise any influence on transfection efficiency caused by different amounts of DNA in the transfection mixture, 1.2 µg of plasmid DNA were used in total in each case. Depending on the size of the TE element introduced, the plasmid size varied between 6.7 kb and 8.2 kb. As a negative control, a mock-transfected pool was run at the same time in each transfection series, i.e. treated the same, but without the addition of DNA in the transfection mixture. The selection of stably transfected cells took place two days after transfection, using HT-supplemented CHO-S-SFMII +G418 (400 µg/mL).

MCP-1 product titres and the specific productivity were obtained over a period of 5 to 6 passages (passaging rhythm 2-2-3 days). FIG. 14 (Series F) shows the relative specific MCP-1 productivities. Each of the elements leads to an increase in the average MCP-1 expression. The greatest increase (15-fold) was obtained using element 13, which even exceeds the 10-fold increase produced by element 08.

Example 8: Influence of the TE Elements at Various Positions and in Various Combinations on the Expression of MCP-1

The effect of the TE elements TE-06 and TE-08 in various combinations and at various positions in the expression plasmid on the expression of the secreted MCP-1 was investigated in two stable transfection series (Series G and H) of CHO-DG44 cells compared with expression without the TE element. In both series, 6 pools were produced per plasmid variant. The base plasmid was pTE4/MCP-1 (FIG. 1B; Selectable Marker NPT=Neomycin=phosphotransferase F240I). The different plasmid variants contained either no TE element (=control mixtures) or TE-08 or TE-A in front of the enhancer/promoter element or the combination of TE-0-6 and TE-08 in front of the enhancer/promoter element or TE-08 or TE-09 in reverse orientation in front of the enhancer/promoter element (Series G). In Series H the elements TE-06 and TE-21 or TE-08 are used in front of the enhancer/promoter element (E/P) and additionally after the termination signal (T) (FIG. 13). In order to minimise any effect on transfection efficiency caused by different amounts of DNA in the transfection mixture, 1.2 µg of plasmid DNA were used in total in each case. Depending on the size of the TE element introduced the plasmid size varied between 6.7 kb and 10.2 kb. As a negative control, a mock-transfected pool was run at the same time as each transfection series, i.e. treated the same but without the addition of DNA in the transfection mixture. The selection of stably transfected cells took place two days after transfection, with HT-supplemented CHO-S-SFMII +G418 (300 µg/mL).

The MCP-1 product titre and specific productivity in Series G were obtained over a period of 6 passages (passaging rhythm 2-2-3 days). The same procedure is used in Series H as well. FIG. 15 shows the relative specific MCP-1 productivities of Series G. All the elements lead to an increase in the average MCP-1 expression. The greatest increase (4-fold) was produced by the element TE-A. The use of the elements TE-06 and TE-21 or TE-08 before and after the expression cassette gave rise to an increase.

Example 9: Influence of TE Element TE-08 on the Expression of Two Immunoglobulins G-4(IgG-4)

The effect of TE element TE-08 on the expression of two IgG-4 antibodies is investigated in a stable transfection series (Series J) of CHO-DG44 cells by comparison with the expression without the TE element. 24 pools are produced with the base plasmids pBIN-LC2 or. pBIN-LC3 and pBID-HC2 or. pBID-HC3 and 24 pools are produced with pBIN-LC2/TE08 or. pBIN-LC3/TE08 and pBID-HC2/TE08 or. pBID-HC3/TE08 (FIG. 16; Selectable Marker NPT=Neomycin-phosphotransferase F240I and dhfr=Dihydrofolate-reductase). In order to minimise any influence on transfection efficiency caused by varying amounts of DNA in the transfection mixture, 1.2 µg of plasmid DNA are used in total in each case. Depending on the size of the TE element introduced, the plasmid size varies between 6.1 kb and 7.5 kb. As a negative control, a mock-transfected pool is run at the same time with each transfection series, i.e. treated the same, but without the addition of DNA to the transfection mixture. The selection of stably transfected cells is carried out two days after transfection, using HT-free CHO-S-SFMII +G418 (400 µg/mL). IgG-4 product titres and the specific productivity are obtained over a period of 4 passages (passaging rhythm 2-2-3 days). The element 08 leads to an increase in the average expression rate in the expression of IgG4 antibodies. Moreover, the chance of finding a high producing cell pool can be increased by the presence of the element TE-08.

Example 10: Influence of TE Elements on Protein Expression in 293F Cells

The effect of various TE elements on the expression of the secreted MCP-1 is investigated in a stable transfection series (Series K) of HEK293 freestyle cells by comparison with MCP-1 expression without a TE element. The base plasmid is pTE-4/MCP-1 (FIG. 1B; Selectable Marker NPT=Neomycin-phosphotransferase F240I). The elements TE-08, TE-13 and TE-A are used in direct orientation upstream from the enhancer/promoter and 7-10 pools are produced per plasmid variant. In order to minimise any effect on transfection efficiency caused by different amounts of DNA in the transfection mixture, 1.2 µg of plasmid DNA are used in total in each case. Depending on the size of the TE element introduced the plasmid size varies between 6.7 kb and 10.2 kb. As a negative control a mock-transfected pool is run at the same time as each transfection series, i.e.

treated the same but without the addition of DNA to the transfection mixture. The selection of stably transfected cells takes place two days after the transfection with 293 SFM II medium+4 mM glutamin+G418 (100 µg/ml).

MCP-1 product titre and the specific productivity are obtained over a period of 5 to 6 passages (passaging rhythm 2-2-3 days).

Example 11: Influence of the TE Element TE-08 on the Expression of an Enzyme (SEAP)

The effect of the TE element TE-08 on the expression of an enzyme (SEAP) is investigated in a stable transfection series (Series L) of CHO-DG44 cells compared with SEAP expression without the TE element. Six pools are produced per plasmid variant. The base plasmid is pTE-4/SEAP. It is generated by exchanging MCP-1-IRES-DsRed2-expression cassette for SEAP. The element TE-08 is cloned into the adaptor A (FIG. 1B; Selectable Marker NPT=Neomycin-phosphotransferase F240I). In order to minimise any effect on the transfection efficiency caused by varying amounts of DNA in the transfection mixture, 1.2 µg of plasmid DNA are used in total in each case. Depending on the size of the TE element introduced the plasmid size varies between 6.6 kb and 7.6 kb. As a negative control a mock-transfected pool is run at the same time as each transfection series, i.e. treated the same but without the addition of DNA to the transfection mixture. The selection of stably transfected cells takes place two days after transfection, with HT-supplemented CHO-S-SFMII +G418 (400 µg/mL).

The relative SEAP expression is determined using the commercially obtainable SEAP assay (Clontech) and obtained over a period of 6 passages (passaging rhythm 2-2-3 days).

LIST OF REFERENCES

Adam, M. A. et al., *J Virol* 1991, 65, 4985-4990
Altschul, S. F. et al., *Nucleic Acids Res.* 1997, 25, 3389-3402
Altschul, S. F. et al., *J Mol Biol* 1990, 215, 403-410
Aronow, B. J. et al., *Mol. Cell. Biol.* 1995, 15, 1123-1135.
Ausubel, F. M. et al., Current Protocols in molecular biology. New York: Greene Publishing Associates and Wiley-Interscience 1994 (updated)
Baker, J. E., *Journal of Experimental Medicine* 1999, 190, 669-679.
Bell, A. C. and Felsenfeld, G., *Current Opinion in Genetics & Development* 1999, 9, 191-198.
Bennett, R. P. et al., *BioTechniques* 1998, 24, 478-482
Chalfie, M. et al., *Science* 1994, 263, 802-805
Chamov, S. M. et al., Antibody Fusion Proteins, Wiley-Liss Inc., 1999
Davies, M. V. et al., *J Virol* 1992, 66, 1924-1932
Delgado, S. et al., *EMBO Journal* 1998, 17, 2426-2435.
Faisst, S. et al., *Nucleic Acids Research* 1992, 20, 3-26
Gossen, M. et al., *Curr Opi Biotech* 1994, 5, 516-520
Haber, D. A. et al., *Somatic Cell Genetics* 1982, 8, 499-508
Harris et al., Protein Purification: A Practical Approach, Pickwood and Hames, eds., IRL Press, 1995
Hemann, C. et al., *DNA Cell Biol* 1994, 13 (4), 437-445
Hu, S. et al., *Cancer Res.* 1996, 56 (13), 3055-3061
Huston, C. et al., *Proc Natl Acad Sci USA* 1988, 85 (16), 5879-5883
Jang, S. K. et al., *J Virol* 1989, 63, 1651-1660
Jenuwein, T. et al., *Nature* 1997, 385, 269-272.
Kaufman, R. J., *Methods in Enzymology* 1990, 185, 537-566
Klehr, D. et al., *Biochemistry* 1991, 30, 1264-1270.
Kortt, A. A. et al., *Protein Engineering* 1997, 10 (4), 423-433
Kwaks, T. H. J. et al., *Nature Biotechnology* 2003, 21, 553-558.
Li, Q. et al., *Blood* 2002, 100, 3077-3086.
Lottspeich F. and Zorbas H. eds., Bioanalytic, Spektrum Akad. Verl., 1998
Lovejoy, B. et al., *Science* 1993, 259, 1288-1293
McKnight, R. A. et al., *PNAS* 1992, 89, 6943-6947.
Monaco, L. et al., *Gene* 1996, 180, 145-15
Morgan, R. A. et al., *Nucleic Acids Research* 1992, 20, 1293-1299
Mosser, D. D. et al., *BioTechniques* 1997, 22, 150-161
Ortiz, B. D. et al., *Molecular & Cellular Biology* 1999, 19, 1901-1909.
Ortiz, B. D. et al., *EMBO J* 1997, 16, 5037-5045.
Ohshima, Y. et al., *J Mol Biol* 1987, 195, 247-259
Pack, P. et al., *Biotechnology* 1993, 11, 1271-1277
Pack, P. et al., *J Mol Biol* 1995, 246 (11), 28-34
Pelletier, J. et al., *Nature* 1988, 334, 320-325
Perisic, O. et al., *Structure* 1994, 2, 1217-1226
Pikaart, M. J. et al., *Genes Dev* 1998, 12, 2852-2862.
Poljak, L. et al., *Nucl. Acids. Res* 1994, 22, 4386-4394.
Ramesh, N. et al., *Nucleic Acids Research* 1996, 24, 2697-2700
Sambrook, J. et al., Molecular Cloning: A Laboratory Manual Cold Spring Harbor Laboratory, Cold Spring Harbor, N.Y., 1989
Sautter, K. and Enenkel, B., *Biotechnology and Bioengineering* 2005, 89, 530-538.
Scopes, R., Protein Purification, Springer Verlag, 1988
Simonson, C. C. et al., *Proc Natl Acad Sci USA* 1983, 80, 2495-2499
Stief, A. et al., *Nature* 1989, 341, 343-345.
Sugimoto et al., *Biotechnology* 1994, 12, 694-698
Udvardy, A. et al., *Journal of Molecular Biology* 1985, 185, 341-358.
Udvardy, A., *EMBO J* 1999, 18, 1-8.
Urlaub, G. et al., *Cell* 1983, 33, 405-412
Urlaub, G. et al., *Somatic Cell & Molecular Genetics* 1986, 12, 555-566.
Werner, R. G. et al., *Arzneimittel-Forschung* 1998, 48, 870-880.
Wigler, M. et al., *Proc Natl Acad Sci USA* 1980, 77, 3567-3570
Yoshimura, T., *FEBS Letters* 1989, 244, 487-493.
Zahn-Zabal, M. et al., *Journal of Biotechnology* 2001, 87, 29-42.
WO97/15664
EP-0-393-438
WO2004/050884
WO02/081677
U.S. Pat. No. 6,027,915
U.S. Pat. No. 6,309,851
WO01/04306
WO00/34318
WO00/34326
WO00/34526
WO01/27150
U.S. Pat. No. 5,122,458
WO94/05785
WO92/08796
WO94/28143
WO03/004704

What is claimed is:

1. A method of preparing a biopharmaceutical product comprising the steps of:
   (a) integrating at least one nucleic acid comprising a TE element comprising SEQ ID No. 15 or the complementary nucleotide sequence thereof into an expression vector comprising a gene of interest,
   (b) transfecting a eukaryotic host cell with the expression vector obtained in step (a), wherein a chromosomal integration of the expression vector leads to an increased transcription or expression of the gene of interest in the eukaryotic host cell,
   (c) selecting a transfected host cell obtained in step (b), wherein said transfected host cell has a higher expression of the gene of interest than a comparable eukaryotic host cell that lacks the TE element and
   (d) cultivating the transfected host cell selected in step (c) under conditions which allow expression of the gene of interest and
   (e) harvesting and purifying biopharmaceutical product encoded by the gene of interest.

2. The method according to claim 1, wherein the transfected host cell selected in step (c) expresses the gene of interest at a level which is increased up to, about or more than two-fold when compared to a comparable cell that lacks the TE element.

3. The method according to claim 1, wherein the transfected host cell selected in step (c) expresses the gene of interest at a level which is increased up to, about or more than three-fold when compared to a comparable cell that lacks the TE element.

4. The method according to claim 1, wherein the transfected host cell selected in step (c) expresses the gene of interest at a level which is increased up to, about or more than four-fold when compared to a comparable cell that lacks the TE element.

5. The method according to claim 1, wherein the transfected host cell selected in step (c) expresses the gene of interest at a level which is increased up to, about or more than five-fold when compared to a comparable cell that lacks the TE element.

6. The method according to claim 1, wherein the transfected host cell selected in step (c) expresses the gene of interest at a level which is increased up to, about or more than six-fold when compared to a comparable cell that lacks the TE element.

7. The method according to claim 1, wherein the transfected host cell selected in step (c) expresses the gene of interest at a level which is increased up to, about or more than seven-fold when compared to a comparable cell that lacks the TE element.

8. The method according to claim 1, wherein the transfected host cell selected in step (c) expresses the gene of interest at a level which is increased up to, about or more than ten-fold when compared to a comparable cell that lacks the TE element.

* * * * *

SEQUENCE LISTING

<160> NUMBER OF SEQ ID NOS: 44

<210> SEQ ID NO 1
<211> LENGTH: 3788
<212> TYPE: DNA
<213> ORGANISM: Artificial
<220> FEATURE:
<223> OTHER INFORMATION: Cricetulus griseus derivative, additional 8
      nucleotides

<400> SEQUENCE: 1

| | | | | | |
|---|---|---|---|---|---|
| ccatgagagc | ctgaagacct | gagttgatac | ccagaaccca | gatcaagatg | gaggagagaa | 60 |
| ccagccccac | taagctgtcc | cctgaccccc | ataaatgcct | ccctgtccag | ttatgccaca | 120 |
| caatgatagg | tgaatacaga | aaaacaccct | tcctttagac | actaagcgga | ttcctcttac | 180 |
| gcataccagt | taagtgatag | ttcttaggct | tcaactcagc | actttaaaaa | gtttatattt | 240 |
| tgcaatgctg | gggactaaat | tagggttgtg | cacatgctaa | gtaagcactc | tacttttgta | 300 |
| tcacatttta | ataattgtaa | gaattaattc | gtgaaatagt | agctgagaca | atagatttgt | 360 |
| ttctttcatg | tgggaactgc | tgtgtgtgct | tcttgctgat | gcaaacaagg | tcaaatactt | 420 |
| tattccccag | tgtctgccta | gccctgtaac | acttctctat | tatacaatga | ccacaaataa | 480 |
| ttaggtgagt | gggttttgtt | tcattttaaa | ttgttgctat | tttagagaca | ggatttcttg | 540 |
| caaacctggt | tggtcttaaa | ctccgtatgt | agctgagaat | gaccttgaaa | accttcctgt | 600 |
| cccacccctc | aaattccaga | attatagaca | cccaccacat | ggcttaataa | gtaaacaaca | 660 |
| acaataaaag | catgacttct | gggtctggag | ggagggcttg | ccagttaaga | gcaatggata | 720 |
| cttttcccata | gaacctgggt | ttgactccca | gcactaacct | acatggtgat | agtgatgcag | 780 |
| cagacataca | tgagggcaac | acacacatgg | gcacatacac | acgcacccgc | ccaccatggc | 840 |
| ttttccccca | tcacttagac | agccatattt | aaacgtagtg | gagccaggct | ggggtggtgg | 900 |
| cccacacctt | taatcccagc | actccagaag | gcagaggtag | gcggatctct | gtgggtttga | 960 |
| gaccagcctg | gtctacaaga | gctagttcca | ggacagcctc | caaagccata | gagaaaccct | 1020 |
| atctcaaaaa | actgaaacaa | caacaacaac | aaaacaaaat | aaaaaacaa | caaagaatc | 1080 |
| ttagtggttc | agtggttcca | cacacaggaa | agtagaaagg | gccttgatgg | gaaggttttc | 1140 |
| agagggagga | gtatggatga | gacaggatga | tagtgaaaag | aactcaaatt | aattaaaatat | 1200 |
| ttgaaactat | ctaagaataa | aagctaaaat | atttaaaatt | acagtcaggt | agtggtggtg | 1260 |
| cagagggcta | agttggtaga | cacagtgaga | tccaggccag | ccagggctac | ctagtgagac | 1320 |
| cttgttcaaa | taactaataa | aatatacaaa | ataaaggaga | caccacaata | atttttgaaat | 1380 |
| gtaaaagact | aaatttacct | tttatattga | tgagttggat | aaaaaaatca | atttaccaga | 1440 |
| gaacataaag | tagtcccatc | aaagacaaaa | gcaatatatg | attaaactct | aatttaaaag | 1500 |
| tttgttagag | cctggcaacg | tggcacatac | ctttaatccc | agcaccaggg | agacagaggc | 1560 |
| catcctggtc | taaaaagtga | tctccaggac | agccatggct | attacacaga | gaaaccctgt | 1620 |
| ctggaaaaac | aaaaaattag | tgtccatgtg | taaatgtgtg | gagtatgctt | gtcatgccac | 1680 |
| atacagaggt | agagggcagt | ttatgggagt | cagttcctat | tcttccttta | tgggggacct | 1740 |
| ggggactgaa | ctcaggtcat | caggcttggc | agaaagtgca | ttagctcacg | gagccttatc | 1800 |
| attggcgaaa | gctctctcaa | gtagaaaatc | aatgtgtttg | ctcatagtgc | aatcattatg | 1860 |
| tttcgagagg | ggaagggtac | aatcgttggg | gcatgtgtgg | tcacatctga | atagcagtag | 1920 |
| ctccctagga | gaattaattc | caagttcttt | ggtggtgtat | caatgcccctt | aaaggggtca | 1980 |

| | |
|---|---:|
| acaactttttt tcccctctga caaaactatc ttcttatgtc cttgtccctc atatttgaag | 2040 |
| tattttattc tttgcagtgt tgaatatcaa ttctagcacc tcagacatgt taggtaagta | 2100 |
| ccctacaact caggttaact aatttaattt aactaattta accccaacac ttttctttg | 2160 |
| tttatccaca tttgtggagt gtgtgtgtgt gtgtgtgtgt gtgtgtgtgt gtgtgtgtgt | 2220 |
| gtgtgtgtgt gtgtgtgtgt gcgcgcgcgc gcgcgctcgg atcattctac cttttgttta | 2280 |
| aaaaatgtta gtccaggggt ggggtgcact gtgaaagtct gagggtaact tgctggggtc | 2340 |
| agttctttcc actataggac agaactccag gtgtcaactc tttactgaca gaaccatcca | 2400 |
| aatagcccta tctaatttta gtttttatt tatttatttt ttgttttcg agacaggggtt | 2460 |
| tctctgtggc tttggaggct gtcctggaac tagctcttgt agaccaggct ggtctcgaac | 2520 |
| tcagagatcc acctgcctct gcctcctgag tgctgggatt aaaggcatgc gccaccaacg | 2580 |
| cttggctcta cctaatttta aagagattg tgtgtcacaa gggtgtcatg tcgccctgca | 2640 |
| accaccccc cccaaaaaa aaaaaaaaaa aaacttcact gaagctgaag cacgatgatt | 2700 |
| tggttactct ggctggccaa tgagctctag ggagtctcct gtcaaacaga atctcaacag | 2760 |
| gcgcagcagt ctttttttaaa gtggggttac aacacaggtt tttgcatatc aggcattta | 2820 |
| tctaagctat ttcccagcca aaaatgtgta ttttggaggc agcagagcta atagattaaa | 2880 |
| atgagggaag agcccacaca ggttattagg aagataagca tcttctttat ataaaacaaa | 2940 |
| accaaaccaa actggaggag gtctacccttt agggatggaa gaaaagacat ttagagggtg | 3000 |
| caatagaaag ggcactgagt ttgtgaggtg gaggactggg agagggcgca accgctttaa | 3060 |
| ctgtcctgtt ttgcctattt tttggggaca gcacatgttc ctattttcc caggatgggc | 3120 |
| aatctccacg tccaaacttg cggtcgagga ctacagtcat tttgcaggtt tccttactgt | 3180 |
| atggcttta aaacgtgcaa aggtgaccat taaccgtttc acgctgggag ggcacgtgcg | 3240 |
| gctcagatgc ttcctctgac tgagggccag gagggggcta cacggaagag gccacacccg | 3300 |
| cacttgggaa gactcgattt gggcttcagc tggctgagac gccccagcag gctcctcggc | 3360 |
| tacaccttca gccccgaatg ccttccggcc cataacccctt cccttctagg catttccggc | 3420 |
| gaggacccac cctcgcgcca aacattcggc cccatccccc ggtcctcacc tgaatctcta | 3480 |
| actctgactc cagagtttag agactataac cagatagccc ggatgtgtgg aactgcatct | 3540 |
| tgggacgagt agttttagca aaagaaagc gacgaaaaac tacaattccc agacagactt | 3600 |
| gtgttacctc tcttctcatg ctaaacaagc cccctttaaa ggaaagcccc tcttagtcgc | 3660 |
| atcgactgtg taagaaaggc gttttgaaaca ttttaatgtt gggcacaccg tttcgaggac | 3720 |
| cgaaatgaga aagagcatag ggaaacggag cgcccgagct agtctggcac tgcgttagac | 3780 |
| agccgcgg | 3788 |

<210> SEQ ID NO 2
<211> LENGTH: 2210
<212> TYPE: DNA
<213> ORGANISM: Cricetulus griseus

<400> SEQUENCE: 2

| | |
|---|---:|
| gatctccagg acagccatgg ctattacaca gagaaaccct gtctggaaaa acaaaaaatt | 60 |
| agtgtccatg tgtaaatgtg tggagtatgc ttgtcatgcc acatacagag gtagagggca | 120 |
| gtttatggga gtcagttcct attcttcctt tatggggac ctggggactg aactcaggtc | 180 |
| atcaggcttg gcagaaagtg cattagctca cggagcctta tcattggcga aagctctctc | 240 |
| aagtagaaaa tcaatgtgtt tgctcatagt gcaatcatta tgtttcgaga ggggaagggt | 300 |

```
acaatcgttg gggcatgtgt ggtcacatct gaatagcagt agctccctag gagaattaat      360
tccaagttct ttggtggtgt atcaatgccc ttaaagggt caacaactt ttttcccctct      420
gacaaaacta tcttcttatg tccttgtccc tcatatttga agtattttat tctttgcagt      480
gttgaatatc aattctagca cctcagacat gttaggtaag taccctacaa ctcaggttaa      540
ctaatttaat ttaactaatt taaccccaac acttttttctt tgtttatcca catttgtgga     600
gtgtgtgtgt gtgtgtgtgt gtgtgtgtgt gtgtgtgtgt gtgtgtgtgt gtgtgtgtgt      660
gtgcgcgcgc gcgcgcgctc ggatcattct accttttgtt taaaaaatgt tagtccaggg      720
gtggggtgca ctgtgaaagt ctgagggtaa cttgctgggg tcagttcttt ccactatagg      780
acagaactcc aggtgtcaac tctttactga cagaaccatc caaatagccc tatctaattt      840
tagttttttta tttatttatt ttttgttttt cgagacaggg tttctctgtg gctttggagg     900
ctgtcctgga actagctctt gtagaccagg ctggtctcga actcagagat ccacctgcct      960
ctgcctcctg agtgctggga ttaaaggcat gcgccaccaa cgcttggctc tacctaatttt    1020
taaaagagat tgtgtgtcac aagggtgtca tgtcgccctg caaccacccc cccccaaaa     1080
aaaaaaaaaa aaaaacttca ctgaagctga agcacgatga tttggttact ctggctggcc    1140
aatgagctct agggagtctc ctgtcaaaca gaatctcaac aggcgcagca gtcttttttta   1200
aagtggggtt acaacacagg ttttttgcata tcaggcattt tatctaagct atttcccagc    1260
caaaaatgtg tattttggag gcagcagagc taatagatta aaatgaggga agagcccaca    1320
caggttatta ggaagataag catcttcttt atataaaaca aaaccaaacc aaactggagg    1380
aggtctacct ttagggatgg aagaaaagac atttagaggg tgcaatagaa agggcactga    1440
gtttgtgagg tggaggactg ggagagggcg caaccgcttt aactgtcctg ttttgcctat    1500
ttttttgggga cagcacatgt tcctattttt cccaggatgg gcaatctcca cgtccaaact    1560
tgcggtcgag gactacagtc attttgcagg tttccttact gtatggcttt taaaacgtgc    1620
aaaggtgacc attaaccgtt tcacgctggg agggcacgtg cggctcagat gcttcctctg    1680
actgagggcc aggaggggggc tacacggaag aggccacacc cgcacttggg aagactcgat    1740
ttgggcttca gctggctgag acgccccagc aggctcctcg gctacacctt cagccccgaa    1800
tgccttccgg cccataaccc ttcccttcta ggcatttccg gcgaggaccc accctcgcgc    1860
caaacattcg gccccatccc ccggtcctca cctgaatctc taactctgac tccagagttt    1920
agagactata accagatagc ccggatgtgt ggaactgcat cttgggacga gtagttttag    1980
caaaaagaaa gcgacgaaaa actacaattc ccagacagac ttgtgttacc tctcttctca    2040
tgctaaacaa gccccctttta aaggaaagcc cctcttagtc gcatcgactg tgtaagaaag    2100
gcgtttgaaa cattttaatg ttgggcacac cgtttcgagg accgaaatga gaaagagcat    2160
agggaaacgg agcgcccgag ctagtctggc actgcgttag acagccgcgg                2210
```

<210> SEQ ID NO 3
<211> LENGTH: 3005
<212> TYPE: DNA
<213> ORGANISM: Artificial
<220> FEATURE:
<223> OTHER INFORMATION: Cricetulus griseus with manipulation of the
      endogenous EcoR1 site by substitution of 4 bases

<400> SEQUENCE: 3

```
gttgctattt tagagacagg atttcttgca aacctggttg gtcttaaact ccgtatgtag       60
ctgagaatga ccttgaaaac cttcctgtcc caccccctcaa attccagaat tatagacacc     120
```

-continued

```
caccacatgg cttaataagt aaacaacaac aataaaagca tgacttctgg gtctggaggg    180
agggcttgcc agttaagagc aatggatact ttcccataga acctgggttt gactcccagc    240
actaacctac atggtgatag tgatgcagca gacatacatg agggcaacac acacatgggc    300
acatacacac gcacccgccc accatggctt ttcccccatc acttagacag ccatatttaa    360
acgtagtgga gccaggctgg ggtggtggcc cacacccttta atcccagcac tccagaaggc    420
agaggtaggc ggatctctgt gggtttgaga ccagcctggt ctacaagagc tagttccagg    480
acagcctcca aagccataga gaaaccctat ctcaaaaaac tgaaacaaca acaacaacaa    540
aacaaaataa aaaacaaca aaagaatctt agtggttcag tggttccaca cacaggaaag    600
tagaaagggc cttgatggga aggttttcag agggaggagt atggatgaga caggatgata    660
gtgaaaagaa ctcaaattaa ttaaatattt gaaactatct aagaataaaa gctaaaatat    720
ttaaaattac agtcaggtag tggtggtgca gagggctaag ttggtagaca cagtgagatc    780
caggccagcc agggctacct agtgagacct tgttcaaata actaataaaa tatacaaaat    840
aaaggagaca ccacaataat tttgaaatgt aaaagactaa atttaccttt tatattgatg    900
agttggataa aaaaatcaat ttaccagaga acataaagta gtcccatcaa agacaaaagc    960
aatatatgat taaactctaa tttaaaagtt tgttagagcc tggcaacgtg gcacatacct   1020
ttaatcccag caccagggag acagaggcca tcctggtcta aaaagtgatc tccaggacag   1080
ccatggctat tacacagaga aaccctgtct ggaaaaacaa aaaattagtg tccatgtgta   1140
aatgtgtgga gtatgcttgt catgccacat acagaggtag agggcagttt atgggagtca   1200
gttcctattc ttcctttatg ggggacctgg ggactgaact caggtcatca ggcttggcag   1260
aaagtgcatt agctcacgga gccttatcat tggcgaaagc tctctcaagt agaaaatcaa   1320
tgtgtttgct catagtgcaa tcattatgtt tcgagagggg aagggtacaa tcgttggggc   1380
atgtgtggtc acatctgaat agcagtagct ccctaggaga attaattcca agttctttgg   1440
tggtgtatca atgcccttaa aggggtcaac aacttttttt ccctctgaca aaactatctt   1500
cttatgtcct tgtccctcat atttgaagta ttttattctt tgcagtgttg aatatcaatt   1560
ctagcacctc agacatgtta ggtaagtacc ctacaactca ggttaactaa tttaatttaa   1620
ctaatttaac cccaacactt tttctttgtt tatccacatt tgtggagtgt gtgtgtgtgt   1680
gtgtgtgtgt gtgtgtgtgt gtgtgtgtgt gtgtgtgtgt gtgtgtgtgc gcgcgcgcgc   1740
gcgctcggat cattctacct tttgtttaaa aaatgttagt ccaggggtgg ggtgcactgt   1800
gaaagtctga gggtaacttg ctggggtcag ttcttttccac tataggacag aactccaggt   1860
gtcaactctt tactgacaga accatccaaa tagccctatc taattttagt ttttatttta   1920 tttattttt gttttttcgag acagggtttc tctgtggctt tggaggctgt cctgaaacta   1980
gctcttgtag accaggctgg tctcgaactc agagatccac ctgcctctgc ctcctgagtg   2040
ctgggattaa aggcatgcgc caccaacgct tggctctacc taattttaaa agagattgtg   2100
tgtcacaagg gtgtcatgtc gccctgcaac cacccccccc ccaaaaaaaa aaaaaaaaaa   2160
acttcactga agctgaagca cgatgatttg gttactctgg ctggccaatg agctctaggg   2220
agtctcctgt caaacagaat ctcaacaggc gcagcagtct ttttttaaagt ggggttacaa   2280 cacaggtttt tgcatatcag gcattttatc taagctattt cccagccaaa aatgtgtatt   2340
ttggaggcag cagagctaat agattaaaat gagggaagag cccacacagg ttattaggaa   2400
gataagcatc ttctttatat aaaacaaaac caaaccaaac tggaggaggt ctacctttag   2460
ggatggaaga aaagacattt agagggtgca atagaaaggg cactgagttt gtgaggtgga   2520
```

```
ggactgggag agggcgcaac cgctttaact gtcctgtttt gcctatttt tggggacagc    2580 acatgttcct attttccca ggatgggcaa tctccacgtc caaacttgcg gtcgaggact    2640
acagtcattt tgcaggttc cttactgtat ggcttttaaa acgtgcaaag gtgaccatta    2700
accgtttcac gctgggaggg cacgtgcggc tcagatgctt cctctgactg agggccagga    2760 ggggctaca cggaagaggc cacacccgca cttgggaaga ctcgatttgg gcttcagctg    2820
gctgagacgc cccagcaggc tcctcggcta caccttcagc cccgaatgcc ttccggccca    2880
taacccttcc cttctaggca tttccggcga ggacccaccc tcgcgccaaa cattcggccc    2940 catccccgg tcctcacctg aatctctaac tctgactcca gagtttagag actataacca    3000
gatag                                                                3005

<210> SEQ ID NO 4
<211> LENGTH: 2517
<212> TYPE: DNA
<213> ORGANISM: Cricetulus griseus

<400> SEQUENCE: 4
caaagccata gagaaaccct atctcaaaaa actgaaacaa caacaacaac aaaacaaaat     60
aaaaaaacaa caaagaatc ttagtggttc agtggttcca cacacaggaa agtagaaagg    120
gccttgatgg gaaggttttc agagggagga gtatggatga acaggatga tagtgaaaag    180 aactcaaatt aattaaatat ttgaaactat ctaagaataa aagctaaaat atttaaaatt    240
acagtcaggt agtggtggtg cagagggcta agttggtaga cacagtgaga tccaggccag    300
ccagggctac ctagtgagac cttgttcaaa taactaataa aatatacaaa ataaaggaga    360
caccacaata attttgaaat gtaaaagact aaatttacct tttatattga tgagttggat    420
aaaaaaatca attaccaga gaacataaag tagtcccatc aaagacaaaa gcaatatatg    480
attaaactct aatttaaaag tttgttagag cctggcaacg tggcacatac ctttaatccc    540
agcaccaggg agacagaggc catcctggtc taaaaagtga tctccaggac agccatggct    600
attacacaga gaaaccctgt ctggaaaaac aaaaaattag tgtccatgtg taaatgtgtg    660
gagtatgctt gtcatgccac atacagaggt agagggcagt tatgggagt cagttcctat    720 tcttcctta tggggaccct ggggactgaa ctcaggtcat caggcttggc agaaagtgca    780
ttagctcacg gagccttatc attggcgaaa gctctctcaa gtagaaaatc aatgtgtttg    840
ctcatagtgc aatcattatg tttcgagagg ggaagggtac aatcgttggg gcatgtgtgg    900
tcacatctga atagcagtag ctccctagga gaattaattc caagttcttt ggtggtgtat    960
caatgccctt aaagggtca acaacttttt ttccctctga caaaactatc ttcttatgtc    1020
cttgtccctc atatttgaag tatttattc tttgcagtgt tgaatatcaa ttctagcacc    1080
tcagacatgt taggtaagta ccctacaact caggttaact aatttaattt aactaattta    1140
accccaacac tttttctttg tttatccaca tttgtggagt gtgtgtgtgt gtgtgtgtgt    1200
gtgtgtgtgt gtgtgtgtgt gtgtgtgtgt gtgtgtgtgt gcgcgcgcgc gcgcgctcgg    1260
atcattctac cttttgttta aaaaatgtta gtccaggggt ggggtgcact gtgaaagtct    1320
gagggtaact tgctggggtc agttcttcc actataggac agaactccag gtgtcaactc    1380
tttactgaca gaaccatcca aatagcccta tctaatttta gttttttatt tatttatttt    1440 ttgttttcg agacagggtt tctctgtggc tttggaggct gtcctggaac tagctcttgt    1500
agaccaggct ggtctcgaac tcagagatcc acctgcctct gcctcctgag tgctgggatt    1560
```

| | |
|---|---|
| aaaggcatgc gccaccaacg cttggctcta cctaatttta aaagagattg tgtgtcacaa | 1620 |
| gggtgtcatg tcgccctgca accaccccc ccccaaaaaa aaaaaaaaaa aaacttcact | 1680 |
| gaagctgaag cacgatgatt tggttactct ggctggccaa tgagctctag ggagtctcct | 1740 |
| gtcaaacaga atctcaacag gcgcagcagt cttttttaaa gtggggttac aacacaggtt | 1800 |
| tttgcatatc aggcatttta tctaagctat ttcccagcca aaaatgtgta ttttggaggc | 1860 |
| agcagagcta atagattaaa atgagggaag agcccacaca ggttattagg aagataagca | 1920 |
| tcttctttat ataaaacaaa accaaaccaa actggaggag gtctaccttt agggatggaa | 1980 |
| gaaaagacat ttagagggtg caatagaaag ggcactgagt ttgtgaggtg gaggactggg | 2040 |
| agagggcgca accgctttaa ctgtcctgtt ttgcctatt tttggggaca gcacatgttc | 2100 |
| ctatttttcc caggatgggc aatctccacg tccaaacttg cggtcgagga ctacagtcat | 2160 |
| tttgcaggtt tccttactgt atggcttta aaacgtgcaa aggtgaccat taaccgtttc | 2220 |
| acgctgggag ggcacgtgcg gctcagatgc ttcctctgac tgagggccag gaggggcta | 2280 |
| cacggaagag gccacacccg cacttgggaa gactcgattt gggcttcagc tggctgagac | 2340 |
| gccccagcag gctcctcggc tacaccttca gccccgaatg ccttccggcc cataacccttt | 2400 |
| cccttctagg catttccggc gaggaccac cctcgcgcca acattcggc cccatccccc | 2460 |
| ggtcctcacc tgaatctcta actctgactc cagagtttag agactataac cagatag | 2517 |

<210> SEQ ID NO 5
<211> LENGTH: 1989
<212> TYPE: DNA
<213> ORGANISM: Cricetulus griseus

<400> SEQUENCE: 5

| | |
|---|---|
| acctttaatc ccagcaccag ggagacagag gccatcctgg tctaaaaagt gatctccagg | 60 |
| acagccatgg ctattacaca gagaaaccct gtctggaaaa acaaaaaatt agtgtccatg | 120 |
| tgtaaatgtg tggagtatgc ttgtcatgcc acatacagag gtagagggca gtttatggga | 180 |
| gtcagttcct attcttcctt tatggggggac ctggggactg aactcaggtc atcaggcttg | 240 |
| gcagaaagtg cattagctca cggagcctta tcattggcga aagctctctc aagtagaaaa | 300 |
| tcaatgtgtt tgctcatagt gcaatcatta tgtttcgaga ggggaagggt acaatcgttg | 360 |
| gggcatgtgt ggtcacatct gaatagcagt agctccctag gagaattaat tccaagttct | 420 |
| ttggtggtgt atcaatgccc ttaaaggggt caacaacttt ttttccctct gacaaaacta | 480 |
| tcttcttatg tccttgtccc tcatatttga agtatttat tctttgcagt gttgaatatc | 540 |
| aattctagca cctcagacat gttaggtaag taccctacaa ctcaggttaa ctaatttaat | 600 |
| ttaactaatt taaccccaac acttttctt tgtttatcca catttgtgga gtgtgtgtgt | 660 |
| gtgtgtgtgt gtgtgtgtgt gtgtgtgtgt gtgtgtgtgt gtgtgtgtgt gtgcgcgcgc | 720 |
| gcgcgcgctc ggatcattct accttttgtt taaaaaatgt tagtccaggg gtggggtgca | 780 |
| ctgtgaaagt ctgagggtaa cttgctgggg tcagttcttt ccactatagg acagaactcc | 840 |
| aggtgtcaac tctttactga cagaaccatc caaatagccc tatctaattt tagttttta | 900 |
| tttatttatt ttttgttttt cgagacaggg tttctctgtg gctttggagg ctgtcctgga | 960 |
| actagctctt gtagaccagg ctggtctcga actcagagat ccacctgcct ctgcctcctg | 1020 |
| agtgctggga ttaaaggcat gcgccaccaa cgcttggctc tacctaattt taaaagagat | 1080 |
| tgtgtgtcac aagggtgtca gtcgccctg caaccacccc cccccaaaa aaaaaaaaaa | 1140 |
| aaaaacttca ctgaagctga agcacgatga tttggttact ctggctggcc aatgagctct | 1200 |

```
agggagtctc ctgtcaaaca gaatctcaac aggcgcagca gtcttttta aagtggggtt    1260
acaacacagg ttttgcata tcaggcattt tatctaagct atttcccagc caaaaatgtg    1320
tattttggag gcagcagagc taatagatta aaatgaggga agagcccaca caggttatta   1380
ggaagataag catcttcttt atataaaaca aaaccaaacc aaactggagg aggtctacct   1440
ttagggatgg aagaaaagac atttagaggg tgcaatagaa agggcactga gtttgtgagg   1500
tggaggactg ggagagggcg caaccgcttt aactgtcctg ttttgcctat ttttttggga   1560
cagcacatgt tcctatttt cccaggatgg gcaatctcca cgtccaaact gcggtcgag    1620
gactacagtc attttgcagg tttccttact gtatggcttt taaaacgtgc aaaggtgacc   1680
attaaccgtt tcacgctggg agggcacgtg cggctcagat gcttcctctg actgagggcc   1740
aggagggggc tacacggaag aggccacacc cgcacttggg aagactcgat ttgggcttca   1800
gctggctgag acgccccagc aggctcctcg gctacacctt cagccccgaa tgccttccgg   1860
cccataaccc ttcccttcta ggcatttccg gcgaggaccc accctcgcgc caaacattcg   1920
gccccatccc ccggtcctca cctgaatctc taactctgac tccagagttt agagactata   1980
accagatag                                                           1989

<210> SEQ ID NO 6
<211> LENGTH: 1512
<212> TYPE: DNA
<213> ORGANISM: Cricetulus griseus

<400> SEQUENCE: 6
ctatcttctt atgtccttgt ccctcatatt tgaagtattt tattctttgc agtgttgaat     60
atcaattcta gcacctcaga catgttaggt aagtacccta caactcaggt taactaattt    120
aattaacta atttaacccc aacactttt ctttgtttat ccacatttgt ggagtgtgtg     180
tgtgtgtgtg tgtgtgtgtg tgtgtgtgtg tgtgtgtgtg tgtgtgcgcg              240
cgcgcgcgcg ctcggatcat tctacctttt gtttaaaaaa tgttagtcca ggggtggggt    300
gcactgtgaa agtctgaggg taacttgctg gggtcagttc tttccactat aggacagaac    360
tccaggtgtc aactctttac tgacagaacc atccaaatag ccctatctaa ttttagtttt    420
ttatttattt attttttgtt tttcgagaca gggtttctct gtggcttgg aggctgtcct    480
ggaactagct cttgtagacc aggctggtct cgaactcaga gatccacctg cctctgcctc    540
ctgagtgctg ggattaaagg catgcgccac caacgcttgg ctctacctaa ttttaaaaga    600
gattgtgtgt cacaagggtg tcatgtcgcc ctgcaaccac cccccccca aaaaaaaaa    660
aaaaaaaact tcactgaagc tgaagcacga tgatttggtt actctggctg gccaatgagc    720
tctagggagt ctcctgtcaa acagaatctc aacaggcgca gcagtctttt ttaaagtggg    780
gttacaacac aggttttgc atatcaggca ttttatctaa gctatttccc agccaaaaat    840
gtgtattttg gaggcagcag agctaataga ttaaaatgag ggaagagccc acacaggtta    900
ttaggaagat aagcatcttc tttatataaa acaaaaccaa accaaactgg aggaggtcta    960
cctttaggga tggaagaaaa gacatttaga ggtgcaata gaaagggcac tgagtttgtg   1020
aggtggagga ctgggagagg gcgcaaccgc tttaactgtc ctgttttgcc tattttttgg   1080
ggacagcaca tgttcctatt tttcccagga tgggcaatct ccacgtccaa acttgcggtc   1140
gaggactaca gtcattttgc aggtttcctt actgtatggc ttttaaaacg tgcaaaggtg   1200
accattaacc gtttcacgct gggagggcac gtgcggctca gatgcttcct ctgactgagg   1260
```

```
gccaggaggg ggctacacgg aagaggccac acccgcactt gggaagactc gatttgggct    1320
tcagctggct gagacgcccc agcaggctcc tcggctacac cttcagcccc gaatgccttc    1380
cggcccataa cccttcccttc ctaggcattt ccggcgagga cccaccctcg cgccaaacat   1440
tcggccccat ccccggtcc tcacctgaat ctctaactct gactccagag tttagagact    1500
ataaccagat ag                                                        1512
```

<210> SEQ ID NO 7
<211> LENGTH: 1013
<212> TYPE: DNA
<213> ORGANISM: Cricetulus griseus

<400> SEQUENCE: 7

```
caggctggtc tcgaactcag agatccacct gcctctgcct cctgagtgct gggattaaag     60
gcatgcgcca ccaacgcttg gctctaccta attttaaaag agattgtgtg tcacaagggt    120
gtcatgtcgc cctgcaacca cccccccccc aaaaaaaaaa aaaaaaaaac ttcactgaag    180
ctgaagcacg atgatttggt tactctggct ggccaatgag ctctagggag tctcctgtca    240
aacagaatct caacaggcgc agcagtcttt tttaaagtgg ggttacaaca caggttttg     300 catatcaggc attttatcta agctatttcc cagccaaaaa tgtgtatttt ggaggcagca    360
gagctaatag attaaaatga gggaagagcc cacacaggtt attaggaaga taagcatctt    420
ctttatataa aacaaaacca aaccaaactg gaggaggtct acctttaggg atggaagaaa    480
agacatttag agggtgcaat agaaagggca ctgagtttgt gaggtggagg actgggagag    540
ggcgcaaccg ctttaactgt cctgttttgc ctattttttg gggacagcac atgttcctat    600
ttttcccagg atgggcaatc tccacgtcca aacttgcggt cgaggactac agtcattttg    660
caggtttcct tactgtatgg cttttaaaac gtgcaaaggt gaccattaac cgtttcacgc    720
tgggagggca cgtgcggctc agatgcttcc tctgactgag ggccaggagg gggctacacg    780
gaagaggcca cacccgcact tgggaagact cgatttgggc ttcagctggc tgagacgccc    840
cagcaggctc tcggctaca ccttcagccc cgaatgcctt ccggcccata cccttccct     900 tctaggcatt tccggcgagg acccaccctc gcgccaaaca ttcggcccca tccccggtc    960 ctcacctgaa tctctaactc tgactccaga gtttagagac tataaccaga tag          1013
```

<210> SEQ ID NO 8
<211> LENGTH: 381
<212> TYPE: DNA
<213> ORGANISM: Artificial
<220> FEATURE:
<223> OTHER INFORMATION: mutant /point mutation in a Cricetulus griseus
      sequence

<400> SEQUENCE: 8

```
cttgcggtcg aggactacag tcattttgca ggtttcctta ctgtatggct tttaaaacgt     60
gcaaaggtga ccattaaccg tttcacgctg gagggcacg tgcggctcag atgcttcctc    120
tgactgaggg ccaggagggg gctacacgga agaggccaca cccgcacttg gaagactcg    180 atttgggctt cagctggctg agacgcccca gcaggctcct cggctacacc ttcagccccg    240
aatgccttcc ggcccataac ccttcccttc taggcatttc cggcgaggac ccaccctcgc    300
gccaaacatt cggccccatc ccccggtcct cacctgaatc tctaactctg actccagagt    360
ttagcgacta taaccagata g                                              381
```

<210> SEQ ID NO 9

<211> LENGTH: 529
<212> TYPE: DNA
<213> ORGANISM: Cricetulus griseus

<400> SEQUENCE: 9

```
gcctgaagac ctgagttgat acccagaacc cagatcaaga tggaggagag aaccagcccc      60
actaagctgt cccctgaccc ccataaatgc ctccctgtcc agttatgcca cacaatgata     120
ggtgaataca gaaaaacacc cttcctttag acactaagcg gattcctctt acgcatacca     180
gttaagtgat agttcttagg cttcaactca gcactttaaa aagtttatat tttgcaatgc     240
tggggactaa attagggttg tgcacatgct aagtaagcac tctacttttg tatcacattt     300
taataattgt aagaattaat tcgtgaaata gtagctgaga caatagattt gtttctttca     360
tgtgggaact gctgtgtgtg cttcttgctg atgcaaacaa ggtcaaatac tttattcccc     420
agtgtctgcc tagccctgta acacttctct attatacaat gaccacaaat aattaggtga     480
gtgggttttg tttcatttta aattgttgct attttagaga caggatttc                 529
```

<210> SEQ ID NO 10
<211> LENGTH: 1015
<212> TYPE: DNA
<213> ORGANISM: Cricetulus griseus

<400> SEQUENCE: 10

```
gcctgaagac ctgagttgat acccagaacc cagatcaaga tggaggagag aaccagcccc      60
actaagctgt cccctgaccc ccataaatgc ctccctgtcc agttatgcca cacaatgata     120
ggtgaataca gaaaaacacc cttcctttag acactaagcg gattcctctt acgcatacca     180
gttaagtgat agttcttagg cttcaactca gcactttaaa aagtttatat tttgcaatgc     240
tggggactaa attagggttg tgcacatgct aagtaagcac tctacttttg tatcacattt     300
taataattgt aagaattaat tcgtgaaata gtagctgaga caatagattt gtttctttca     360
tgtgggaact gctgtgtgtg cttcttgctg atgcaaacaa ggtcaaatac tttattcccc     420
agtgtctgcc tagccctgta acacttctct attatacaat gaccacaaat aattaggtga     480
gtgggttttg tttcatttta aattgttgct attttagaga caggatttct tgcaaacctg     540
gttggtctta aactccgtat gtagctgaga atgaccttga aaaccttcct gtcccacccc     600
tcaaattcca gaattataga cacccaccac atggcttaat aagtaaacaa caacaataaa     660
agcatgactt ctgggtctgg agggagggct tgccagttaa gagcaatgga actttccca     720
tagaacctgg gtttgactcc cagcactaac ctacatggtg atagtgatgc agcagacata     780
catgagggca acacacacat gggcacatac acacgcaccc gcccaccatg gcttttcccc     840
catcacttag acagccatat ttaaacgtag tggagccagg ctggggtggt ggcccacacc     900
tttaatccca gcactccaga aggcagaggt aggcggatct ctgtgggttt gagaccagcc     960
tggtctacaa gagctagttc caggacagcc tccaaagcca tagagaaacc ctatc         1015
```

<210> SEQ ID NO 11
<211> LENGTH: 1541
<212> TYPE: DNA
<213> ORGANISM: Cricetulus griseus

<400> SEQUENCE: 11

```
gcctgaagac ctgagttgat acccagaacc cagatcaaga tggaggagag aaccagcccc      60
actaagctgt cccctgaccc ccataaatgc ctccctgtcc agttatgcca cacaatgata     120
ggtgaataca gaaaaacacc cttcctttag acactaagcg gattcctctt acgcatacca     180
```

```
gttaagtgat agttcttagg cttcaactca gcactttaaa aagtttatat tttgcaatgc    240
tggggactaa attagggttg tgcacatgct aagtaagcac tctactttg tatcacattt     300 taataattgt aagaattaat tcgtgaaata gtagctgaga caatagattt gtttctttca    360
tgtgggaact gctgtgtgtg cttcttgctg atgcaaacaa ggtcaaatac tttattcccc    420
agtgtctgcc tagccctgta acacttctct attatacaat gaccacaaat aattaggtga    480
gtgggttttg tttcatttta aattgttgct attttagaga caggattttct tgcaaacctg   540 gttggtctta aactccgtat gtagctgaga atgaccttga aaaccttcct gtcccacccc    600
tcaaattcca gaattataga cacccaccac atggcttaat aagtaaacaa caacaataaa    660
agcatgactt ctgggtctgg agggagggct tgccagttaa gagcaatgga tactttccca   720
tagaacctgg gtttgactcc cagcactaac ctacatggtg atagtgatgc agcagacata    780
catgagggca acacacacat gggcacatac acacgcaccc gcccaccatg gcttttcccc    840
catcacttag acagccatat ttaaacgtag tggagccagg ctggggtggt ggcccacacc    900
tttaatccca gcactccaga aggcagaggt aggcggatct ctgtgggttt gagaccagcc    960
tggtctacaa gagctagttc caggacagcc tccaaagcca tagagaaacc ctatctcaaa   1020
aaactgaaac aacaacaaca acaaaacaaa ataaaaaaac aacaaagaa tcttagtggt    1080 tcagtggttc cacacacagg aaagtagaaa gggccttgat gggaaggttt tcagagggag   1140
gagtatggat gagacaggat gatagtgaaa agaactcaaa ttaattaaat atttgaaact    1200
atctaagaat aaaagctaaa atatttaaaa ttacagtcag gtagtggtgg tgcagagggc   1260
taagttggta gacacagtga gatccaggcc agccagggct acctagtgag accttgttca   1320
aataactaat aaaatataca aataaaggag acaccacaa taattttgaa atgtaaaaga    1380
ctaaatttac cttttatatt gatgagttgg ataaaaaaat caattaccca gagaacataa    1440
agtagtccca tcaaagacaa aagcaatata tgattaaact ctaatttaaa agtttgttag    1500
agcctggcaa cgtggcacat acctttaatc ccagcaccag g                       1541
```

<210> SEQ ID NO 12
<211> LENGTH: 2020
<212> TYPE: DNA
<213> ORGANISM: Cricetulus griseus

<400> SEQUENCE: 12

```
gcctgaagac ctgagttgat acccagaacc cagatcaaga tggaggagag aaccagcccc    60
actaagctgt cccctgaccc ccataaatgc ctccctgtcc agttatgcca cacaatgata   120
ggtgaataca gaaaaacacc cttcctttag acactaagcg gattcctctt acgcatacca   180
gttaagtgat agttcttagg cttcaactca gcactttaaa aagtttatat tttgcaatgc   240
tggggactaa attagggttg tgcacatgct aagtaagcac tctactttg tatcacattt    300 taataattgt aagaattaat tcgtgaaata gtagctgaga caatagattt gtttctttca   360
tgtgggaact gctgtgtgtg cttcttgctg atgcaaacaa ggtcaaatac tttattcccc   420
agtgtctgcc tagccctgta acacttctct attatacaat gaccacaaat aattaggtga   480
gtgggttttg tttcatttta aattgttgct attttagaga caggattttct tgcaaacctg  540 gttggtctta aactccgtat gtagctgaga atgaccttga aaaccttcct gtcccacccc   600
tcaaattcca gaattataga cacccaccac atggcttaat aagtaaacaa caacaataaa   660
agcatgactt ctgggtctgg agggagggct tgccagttaa gagcaatgga tactttccca   720
```

```
tagaacctgg gtttgactcc cagcactaac ctacatggtg atagtgatgc agcagacata    780
catgagggca acacacacat gggcacatac acacgcaccc gcccaccatg gcttttcccc    840
catcacttag acagccatat ttaaacgtag tggagccagg ctggggtggt ggcccacacc    900
tttaatccca gcactccaga aggcagaggt aggcggatct ctgtgggttt gagaccagcc    960
tggtctacaa gagctagttc caggacagcc tccaaagcca tagagaaacc ctatctcaaa   1020
aaactgaaac aacaacaaca acaaaacaaa ataaaaaaac aacaaaagaa tcttagtggt   1080
tcagtggttc cacacacagg aaagtagaaa gggccttgat gggaaggttt tcagagggag   1140
gagtatggat gagacaggat gatagtgaaa agaactcaaa ttaattaaat atttgaaact   1200
atctaagaat aaaagctaaa atatttaaaa ttacagtcag gtagtggtgg tgcagagggc   1260
taagttggta gacacagtga gatccaggcc agccagggct acctagtgag accttgttca   1320
aataactaat aaaatataca aaataaagga gacaccacaa taattttgaa atgtaaaaga   1380
ctaaatttac cttttatatt gatgagttgg ataaaaaaat caatttacca gagaacataa   1440
agtagtccca tcaaagacaa aagcaatata tgattaaact ctaatttaaa agtttgttag   1500
agcctggcaa cgtggcacat acctttaatc ccagcaccag ggagacagag gccatcctgg   1560
tctaaaaagt gatctccagg acagccatgg ctattacaca gagaaaccct gtctggaaaa   1620
acaaaaaatt agtgtccatg tgtaaatgtg tggagtatgc ttgtcatgcc acatacagag   1680
gtagagggca gtttatggga gtcagttcct attcttcctt tatgggggac ctggggactg   1740
aactcaggtc atcaggcttg gcagaaagtg cattagctca cggagcctta tcattggcga   1800
aagctctctc aagtagaaaa tcaatgtgtt tgctcatagt gcaatcatta tgtttcgaga   1860
ggggaagggt acaatcgttg gggcatgtgt ggtcacatct gaatagcagt agctccctag   1920
gagaattaat tccaagttct ttggtggtgt atcaatgccc ttaaagggt caacaacttt    1980 ttttccctct gacaaaacta tcttcttatg tccttgtccc                          2020

<210> SEQ ID NO 13
<211> LENGTH: 2516
<212> TYPE: DNA
<213> ORGANISM: Cricetulus griseus

<400> SEQUENCE: 13
gcctgaagac ctgagttgat acccagaacc cagatcaaga tggaggagag aaccagcccc     60
actaagctgt ccctgacccc cataaatgc ctccctgtcc agttatgcca cacaatgata    120
ggtgaataca gaaaacaccc cttcctttag acactaagcg gattcctctt acgcatacca    180
gttaagtgat agttcttagg cttcaactca gcactttaaa aagtttatat tttgcaatgc    240 tgggactaa attaggggttg tgcacatgct aagtaagcac tctactttg tatcacattt    300 taataattgt aagaattaat tcgtgaaata gtagctgaga caatagattt gtttctttca    360
tgtgggaact gctgtgtgtg cttcttgctg atgcaaacaa ggtcaaatac tttattcccc    420
agtgtctgcc tagccctgta acacttctct attatacaat gaccacaaat aattaggtga    480
gtgggttttg tttcatttta aattgttgct attttagaga caggatttct tgcaaacctg    540
gttggtctta aactccgtat gtagctgaga atgaccttga aaaccttcct gtcccacccc    600
tcaaattcca gaattataga cacccaccac atggcttaat aagtaaacaa caacaataaa    660
agcatgactt ctgggtctgg agggagggct tgccagttaa gagcaatgga tactttccca    720
tagaacctgg gtttgactcc cagcactaac ctacatggtg atagtgatgc agcagacata    780
catgagggca acacacacat gggcacatac acacgcaccc gcccaccatg gcttttcccc    840
```

```
catcacttag acagccatat ttaaacgtag tggagccagg ctggggtggt ggcccacacc    900
tttaatccca gcactccaga aggcagaggt aggcggatct ctgtgggttt gagaccagcc    960
tggtctacaa gagctagttc caggacagcc tccaaagcca tagagaaacc ctatctcaaa   1020
aaactgaaac aacaacaaca acaaaacaaa ataaaaaaac aacaaagaa tcttagtggt    1080 tcagtggttc cacacacagg aaagtagaaa gggccttgat gggaaggttt cagagggag    1140 gagtatggat gagacaggat gatagtgaaa agaactcaaa ttaattaaat atttgaaact   1200
atctaagaat aaaagctaaa atatttaaaa ttacagtcag gtagtggtgg tgcagagggc   1260
taagttggta gacacagtga gatccaggcc agccagggct acctagtgag accttgttca   1320
aataactaat aaaatataca aaataaagga gacaccacaa taattttgaa atgtaaaaga   1380
ctaaatttac cttttatatt gatgagttgg ataaaaaaat caatttacca gagaacataa   1440
agtagtccca tcaaagacaa aagcaatata tgattaaact ctaatttaaa agtttgttag   1500
agcctggcaa cgtggcacat acctttaatc ccagcaccag ggagacagag gcatcctgg    1560 tctaaaaagt gatctccagg acagccatgg ctattacaca gagaaaccct gtctggaaaa   1620
acaaaaaatt agtgtccatg tgtaaatgtg tggagtatgc ttgtcatgcc acatacagag   1680
gtagagggca gtttatggga gtcagttcct attcttcctt tatggggac ctggggactg    1740 aactcaggtc atcaggcttg gcagaaagtg cattagctca cggagcctta tcattggcga   1800
aagctctctc aagtagaaaa tcaatgtgtt tgctcatagt gcaatcatta tgtttcgaga   1860
ggggaagggt acaatcgttg gggcatgtgt ggtcacatct gaatagcagt agctccctag   1920
gagaattaat tccaagttct ttggtggtgt atcaatgccc ttaaggggt caacaacttt    1980 ttttccctct gacaaaacta tcttcttatg tccttgtccc tcatatttga agtattttat   2040
tctttgcagt gttgaatatc aattctagca cctcagacat gttaggtaag taccctacaa   2100
ctcaggttaa ctaatttaat ttaactaatt taaccccaac acttttttctt tgtttatcca   2160 catttgtgga gtgtgtgtgt gtgtgtgtgt gtgtgtgtgt gtgtgtgtgt gtgtgtgtgt   2220
gtgtgtgtgt gtgcgcgcgc gcgcgcgctc ggatcattct accttttgtt taaaaaatgt   2280
tagtccaggg gtggggtgca ctgtgaaagt ctgagggtaa cttgctgggg tcagttcttt   2340
ccactatagg acagaactcc aggtgtcaac tctttactga cagaaccatc caaatagccc   2400
tatctaattt tagttttta tttatttatt ttttgttttt cgagacaggg tttctctgtg    2460
gctttggagg ctgtcctgga actagctctt gtagaccagg ctggtctcga actcag       2516
```

<210> SEQ ID NO 14
<211> LENGTH: 3148
<212> TYPE: DNA
<213> ORGANISM: Cricetulus griseus

<400> SEQUENCE: 14

```
gcctgaagac ctgagttgat acccagaacc cagatcaaga tggaggagag aaccagcccc     60
actaagctgt cccctgaccc ccataaatgc ctccctgtcc agttatgcca cacaatgata   120
ggtgaataca gaaaaacacc cttcctttag acactaagcg gattcctctt acgcatacca   180
gttaagtgat agttcttagg cttcaactca gcactttaaa aagtttatat tttgcaatgc   240
tggggactaa attagggttg tgcacatgct aagtaagcac tctactttg tatcacattt    300 taataattgt aagaattaat tcgtgaaata gtagctgaga caatagattt gtttctttca   360
tgtgggaact gctgtgtgtg cttcttgctg atgcaaacaa ggtcaaatac tttattcccc   420
```

```
agtgtctgcc tagccctgta acacttctct attatacaat gaccacaaat aattaggtga      480
gtgggttttg tttcatttta aattgttgct attttagaga caggattttct tgcaaacctg     540 gttggtctta aactccgtat gtagctgaga atgaccttga aaaccttcct gtcccacccc      600
tcaaattcca gaattataga cacccaccac atggcttaat aagtaaacaa caacaataaa      660
agcatgactt ctgggtctgg agggagggct tgccagttaa gagcaatgga tactttccca      720
tagaacctgg gtttgactcc cagcactaac ctacatggtg atagtgatgc agcagacata      780
catgagggca acacacacat gggcacatac acacgcaccc gcccaccatg gcttttcccc      840
catcacttag acagccatat ttaaacgtag tggagccagg ctggggtggt ggcccacacc      900
tttaatccca gcactccaga aggcagaggt aggcggatct ctgtgggttt gagaccagcc      960
tggtctacaa gagctagttc caggacagcc tccaaagcca tagagaaacc ctatctcaaa     1020
aaactgaaac aacaacaaca acaaaacaaa ataaaaaaac aacaaagaa tcttagtggt      1080 tcagtggttc cacacacagg aaagtagaaa gggccttgat gggaaggttt tcagagggag     1140
gagtatggat gagacaggat gatagtgaaa agaactcaaa ttaattaaat atttgaaact     1200
atctaagaat aaaagctaaa atatttaaaa ttacagtcag gtagtggtgg tgcagagggc     1260
taagttggta gacacagtga gatccaggcc agccagggct acctagtgag accttgttca     1320
aataactaat aaaatataca aaataaagga gacaccacaa taattttgaa atgtaaaaga     1380
ctaaatttac cttttatatt gatgagttgg ataaaaaaat caatttacca gagaacataa     1440
agtagtccca tcaaagacaa aagcaatata tgattaaact ctaatttaaa agtttgttag     1500
agcctggcaa cgtggcacat acctttaatc ccagcaccag ggagacagag gccatcctgg     1560 tctaaaagt gatctccagg acagccatgg ctattacaca gagaaaccct gtctggaaaa      1620
acaaaaaatt agtgtccatg tgtaaatgtg tggagtatgc ttgtcatgcc acatacagag     1680
gtagagggca gtttatggga gtcagttcct attcttcctt tatgggggac ctggggactg     1740
aactcaggtc atcaggcttg gcagaaagtg cattagctca cggagcctta tcattggcga     1800
aagctctctc aagtagaaaa tcaatgtgtt tgctcatagt gcaatcatta tgtttcgaga     1860
ggggaagggt acaatcgttg gggcatgtgt ggtcacatct gaatagcagt agctccctag     1920
gagaattaat tccaagttct ttggtggtgt atcaatgccc ttaaaggggt caacaacttt     1980
ttttccctct gacaaaacta tcttcttatg tccttgtccc tcatatttga agtatttat      2040 tctttgcagt gttgaatatc aattctagca cctcagacat gttaggtaag taccctacaa     2100
ctcaggttaa ctaatttaat ttaactaatt taaccccaac acttttctt tgtttatcca      2160 catttgtgga gtgtgtgtgt gtgtgtgtgt gtgtgtgtgt gtgtgtgtgt gtgtgtgtgt     2220
gtgtgtgtgt gtgcgcgcgc gcgcgcgctc ggatcattct accttttgtt taaaaaatgt     2280
tagtccaggg gtggggtgca ctgtgaaagt ctgagggtaa cttgctgggg tcagttctt      2340 ccactatagg acagaactcc aggtgtcaac tctttactga cagaaccatc caaatagccc     2400
tatctaattt tagtttttta tttatttatt ttttgttttt cgagacaggg tttctctgtg     2460
gctttggagg ctgtcctgga actagctctt gtagaccagg ctggtctcga actcagagat     2520
ccacctgcct ctgcctcctg agtgctggga ttaaaggcat gcgccaccaa cgcttggctc     2580
tacctaattt taaaagagat tgtgtgtcac aagggtgtca tgtcgccctg caaccacccc     2640 cccccaaaa aaaaaaaaa aaaaacttca ctgaagctga agcacgatga tttggttact      2700
ctggctggcc aatgagctct agggagtctc ctgtcaaaca gaatctcaac aggcgcagca     2760
gtctttttta aagtggggtt acaacacagg tttttgcata tcaggcattt tatctaagct     2820
```

```
atttcccagc caaaaatgtg tattttggag gcagcagagc taatagatta aaatgaggga    2880
agagcccaca caggttatta ggaagataag catcttcttt atataaaaca aaaccaaacc    2940
aaactggagg aggtctacct ttagggatgg aagaaaagac atttagaggg tgcaatagaa    3000
agggcactga gtttgtgagg tggaggactg ggagagggcg caaccgcttt aactgtcctg    3060
ttttgcctat tttttgggga cagcacatgt tcctattttt cccaggatgg gcaatctcca    3120
cgtccaaact tgcggtcgag gactacag                                      3148

<210> SEQ ID NO 15
<211> LENGTH: 511
<212> TYPE: DNA
<213> ORGANISM: Cricetulus griseus

<400> SEQUENCE: 15
gttgctattt tagagacagg atttcttgca aacctggttg gtcttaaact ccgtatgtag     60
ctgagaatga ccttgaaaac cttcctgtcc caccccctcaa attccagaat tatagacacc    120
caccacatgg cttaataagt aaacaacaac aataaaagca tgacttctgg gtctggaggg    180
agggcttgcc agttaagagc aatggatact ttcccataga acctgggttt gactcccagc    240
actaacctac atggtgatag tgatgcagca gacatacatg agggcaacac acacatgggc    300
acatacacac gcacccgccc accatggctt ttcccccatc acttagacag ccatatttaa    360
acgtagtgga gccaggctgg ggtggtggcc cacacccttta atcccagcac tccagaaggc    420
agaggtaggc ggatctctgt gggtttgaga ccagcctggt ctacaagagc tagttccagg    480
acagcctcca aagccataga gaaaccctat c                                   511

<210> SEQ ID NO 16
<211> LENGTH: 549
<212> TYPE: DNA
<213> ORGANISM: Cricetulus griseus

<400> SEQUENCE: 16
caaagccata gagaaaccct atctcaaaaa actgaaacaa caacaacaac aaaacaaaat     60
aaaaaaacaa caaaagaatc ttagtggttc agtggttcca cacacaggaa agtagaaagg    120
gccttgatgg gaaggttttc agagggagga gtatggatga gacaggatga tagtgaaaag    180
aactcaaatt aattaaatat ttgaaactat ctaagaataa aagctaaaat atttaaaatt    240
acagtcaggt agtggtggtg cagagggcta gttggtaga cacagtgaga tccaggccag    300
ccagggctac ctagtgagac cttgttcaaa taactaataa aatatacaaa ataaaggaga    360
caccacaata atttttgaaat gtaaaagact aaatttacct tttatattga tgagttggat    420
aaaaaaatca atttaccaga gaacataaag tagtcccatc aaagacaaaa gcaatatatg    480
attaaactct aatttaaaag tttgttagag cctggcaacg tggcacatac ctttaatccc    540
agcaccagg                                                            549

<210> SEQ ID NO 17
<211> LENGTH: 1037
<212> TYPE: DNA
<213> ORGANISM: Cricetulus griseus

<400> SEQUENCE: 17
gttgctattt tagagacagg atttcttgca aacctggttg gtcttaaact ccgtatgtag     60
ctgagaatga ccttgaaaac cttcctgtcc caccccctcaa attccagaat tatagacacc    120
```

| | |
|---|---|
| caccacatgg cttaataagt aaacaacaac aataaaagca tgacttctgg gtctggaggg | 180 |
| agggcttgcc agttaagagc aatggatact ttcccataga acctgggttt gactcccagc | 240 |
| actaacctac atggtgatag tgatgcagca gacatacatg agggcaacac acacatgggc | 300 |
| acatacacac gcacccgccc accatggctt ttcccccatc acttagacag ccatatttaa | 360 |
| acgtagtgga gccaggctgg ggtggtggcc cacacctttta atcccagcac tccagaaggc | 420 |
| agaggtaggc ggatctctgt gggtttgaga ccagcctggt ctacaagagc tagttccagg | 480 |
| acagcctcca aagccataga gaaaccctat ctcaaaaaac tgaaacaaca caacaacaa | 540 |
| aacaaaataa aaaacaaca aaagaatctt agtggttcag tggttccaca cacaggaaag | 600 |
| tagaaagggc cttgatggga aggttttcag agggaggagt atggatgaga caggatgata | 660 |
| gtgaaaagaa ctcaaattaa ttaaatattt gaaactatct aagaataaaa gctaaaatat | 720 |
| ttaaaattac agtcaggtag tggtggtgca gagggctaag ttggtagaca cagtgagatc | 780 |
| caggccagcc agggctacct agtgagacct tgttcaaata actaataaaa tatacaaaat | 840 |
| aaaggagaca ccacaataat tttgaaatgt aaaagactaa atttaccttt tatattgatg | 900 |
| agttggataa aaaatcaat ttaccagaga acataaagta gtcccatcaa agacaaaagc | 960 |
| aatatatgat taaactctaa tttaaaagtt tgttagagcc tggcaacgtg gcatacct | 1020 |
| ttaatcccag caccagg | 1037 |

<210> SEQ ID NO 18
<211> LENGTH: 500
<212> TYPE: DNA
<213> ORGANISM: Cricetulus griseus

<400> SEQUENCE: 18

| | |
|---|---|
| acctttaatc ccagcaccag ggagacagag gccatcctgg tctaaaaagt gatctccagg | 60 |
| acagccatgg ctattacaca gagaaaccct gtctggaaaa acaaaaaatt agtgtccatg | 120 |
| tgtaaatgtg tggagtatgc ttgtcatgcc acatacagag gtagagggca gtttatggga | 180 |
| gtcagttcct attcttcctt tatggggggac ctggggactg aactcaggtc atcaggcttg | 240 |
| gcagaaagtg cattagctca cggagcctta tcattggcga aagctctctc aagtagaaaa | 300 |
| tcaatgtgtt tgctcatagt gcaatcatta tgtttcgaga ggggaagggt acaatcgttg | 360 |
| gggcatgtgt ggtcacatct gaatagcagt agctccctag gagaattaat tccaagttct | 420 |
| ttggtggtgt atcaatgccc ttaaagggggt caacaacttt ttttccctct gacaaaacta | 480 |
| tcttcttatg tccttgtccc | 500 |

<210> SEQ ID NO 19
<211> LENGTH: 1028
<212> TYPE: DNA
<213> ORGANISM: Cricetulus griseus

<400> SEQUENCE: 19

| | |
|---|---|
| caaagccata gagaaaccct atctcaaaaa actgaaacaa caacaacaac aaaacaaaat | 60 |
| aaaaaaacaa caaaagaatc ttagtggttc agtggttcca cacacaggaa agtagaaagg | 120 |
| gccttgatgg gaaggttttc agagggagga gtatggatga acaggatga tagtgaaaag | 180 |
| aactcaaatt aattaaatat ttgaaactat ctaagaataa aagctaaaat atttaaaatt | 240 |
| acagtcaggt agtggtggtg cagagggcta agttggtaga cacagtgaga tccaggccag | 300 |
| ccagggctac ctagtgagac cttgttcaaa taactaataa aatatacaaa ataaaggaga | 360 |
| caccacaata attttgaaat gtaaaagact aaatttacct tttatattga tgagttggat | 420 |

```
aaaaaaatca atttaccaga gaacataaag tagtcccatc aaagacaaaa gcaatatatg       480
attaaactct aatttaaaag tttgttagag cctggcaacg tggcacatac ctttaatccc       540
agcaccaggg agacagaggc catcctggtc taaaaagtga tctccaggac agccatggct       600
attacacaga gaaccctgt ctggaaaaac aaaaaattag tgtccatgtg taaatgtgtg        660
gagtatgctt gtcatgccac atacagaggt agagggcagt ttatgggagt cagttcctat       720
tcttccttta tggggaccct ggggactgaa ctcaggtcat caggcttggc agaaagtgca       780
ttagctcacg gagccttatc attggcgaaa gctctctcaa gtagaaaatc aatgtgtttg       840
ctcatagtgc aatcattatg tttcgagagg ggaagggtac aatcgttggg gcatgtgtgg      900
tcacatctga atagcagtag ctccctagga gaattaattc caagttcttt ggtggtgtat       960 caatgcccctt aaagggggtca acaactttttt tccctctga caaaactatc ttcttatgtc   1020
cttgtccc                                                              1028

<210> SEQ ID NO 20
<211> LENGTH: 1516
<212> TYPE: DNA
<213> ORGANISM: Cricetulus griseus

<400> SEQUENCE: 20
gttgctattt tagagacagg atttcttgca aacctggttg gtcttaaact ccgtatgtag        60
ctgagaatga ccttgaaaac cttcctgtcc caccccctcaa attccagaat tatagacacc      120
caccacatgg cttaataagt aaacaacaac aataaaagca tgacttctgg gtctggaggg      180
agggcttgcc agttaagagc aatggatact ttcccataga acctgggttt gactcccagc      240
actaacctac atggtgatag tgatgcagca gacatacatg agggcaacac acacatgggc      300
acatacacac gcacccgccc accatggctt ttcccccatc acttagacag ccatatttaa      360
acgtagtgga gccaggctgg ggtggtggcc cacacctttta atcccagcac tccagaaggc      420
agaggtaggc ggatctctgt gggtttgaga ccagcctggt ctacaagagc tagttccagg      480
acagcctcca aagccataga gaaacccctat ctcaaaaaac tgaaacaaca acaacaacaa     540
aacaaaataa aaaacaaca aaagaatctt agtggttcag tggttccaca cacaggaaag      600
tagaaagggc cttgatggga aggttttcag agggaggagt atggatgaga caggatgata      660
gtgaaaagaa ctcaaattaa ttaaatattt gaaactatct aagaataaaa gctaaaatat      720
ttaaaattac agtcaggtag tggtggtgca gagggctaag ttggtagaca cagtgagatc      780
caggccagcc agggctacct agtgagacct tgttcaaata actaataaaa tatacaaaat       840
aaaggagaca ccacaataat tttgaaatgt aaaagactaa atttacccttt tatattgatg       900 agttggataa aaaaatcaat ttaccagaga acataaagta gtcccatcaa agacaaaagc      960
aatatatgat taaactctaa tttaaaagtt tgttagagcc tggcaacgtg gcacatacct     1020
ttaatcccag caccagggag acagaggcca tcctggtcta aaaagtgatc tccaggacag     1080
ccatggctat tacacagaga aaccctgtct ggaaaaacaa aaaattagtg tccatgtgta     1140
aatgtgtgga gtatgcttgt catgccacat acagaggtag agggcagttt atgggagtca     1200
gttcctattc ttcctttatg ggggacctgg ggactgaact caggtcatca ggcttggcag     1260
aaagtgcatt agctcacgga gccttatcat tggcgaaagc tctctcaagt agaaaatcaa     1320
tgtgtttgct catagtgcaa tcattatgtt tcgagagggg aagggtacaa tcgttggggc     1380
atgtgtggtc acatctgaat agcagtagct ccctaggaga attaattcca agttctttgg     1440
```

```
tggtgtatca atgcccttaa aggggtcaac aactttttt ccctctgaca aaactatctt    1500
cttatgtcct tgtccc                                                   1516

<210> SEQ ID NO 21
<211> LENGTH: 381
<212> TYPE: DNA
<213> ORGANISM: Cricetulus griseus

<400> SEQUENCE: 21
cttgcggtcg aggactacag tcattttgca ggtttcctta ctgtatggct tttaaaacgt     60
gcaaaggtga ccattaaccg tttcacgctg ggagggcacg tgcggctcag atgcttcctc    120
tgactgaggg ccaggagggg gctacacgga agaggccaca cccgcacttg ggaagactcg    180
atttgggctt cagctggctg agacgcccca gcaggctcct cggctacacc ttcagccccg    240
aatgccttcc ggcccataac ccttcccttc taggcatttc cggcgaggac ccaccctcgc    300
gccaaacatt cggccccatc ccccggtcct cacctgaatc tctaactctg actccagagt    360
ttagagacta taaccagata g                                              381

<210> SEQ ID NO 22
<211> LENGTH: 34
<212> TYPE: DNA
<213> ORGANISM: Artificial
<220> FEATURE:
<223> OTHER INFORMATION: primer

<400> SEQUENCE: 22
ctatgaggat ccgcctgaag acctgagttg atac                                 34

<210> SEQ ID NO 23
<211> LENGTH: 37
<212> TYPE: DNA
<213> ORGANISM: Artificial
<220> FEATURE:
<223> OTHER INFORMATION: primer

<400> SEQUENCE: 23
tatgcaggat ccgttgctat tttagagaca ggatttc                              37

<210> SEQ ID NO 24
<211> LENGTH: 35
<212> TYPE: DNA
<213> ORGANISM: Artificial
<220> FEATURE:
<223> OTHER INFORMATION: primer

<400> SEQUENCE: 24
tatgcaggat cccaaagcca tagagaaacc ctatc                                35

<210> SEQ ID NO 25
<211> LENGTH: 33
<212> TYPE: DNA
<213> ORGANISM: Artificial
<220> FEATURE:
<223> OTHER INFORMATION: primer

<400> SEQUENCE: 25
tatgcaggat ccacctttaa tcccagcacc agg                                  33

<210> SEQ ID NO 26
<211> LENGTH: 35
<212> TYPE: DNA
<213> ORGANISM: Artificial
```

<220> FEATURE:
<223> OTHER INFORMATION: primer

<400> SEQUENCE: 26
ctatgaggat ccctatcttc ttatgtcctt gtccc                35

<210> SEQ ID NO 27
<211> LENGTH: 32
<212> TYPE: DNA
<213> ORGANISM: Artificial
<220> FEATURE:
<223> OTHER INFORMATION: primer

<400> SEQUENCE: 27
tatgcaggat cccaggctgg tctcgaactc ag                   32

<210> SEQ ID NO 28
<211> LENGTH: 32
<212> TYPE: DNA
<213> ORGANISM: Artificial
<220> FEATURE:
<223> OTHER INFORMATION: primer

<400> SEQUENCE: 28
ctatgaggat cccttgcggt cgaggactac ag                   32

<210> SEQ ID NO 29
<211> LENGTH: 34
<212> TYPE: DNA
<213> ORGANISM: Artificial
<220> FEATURE:
<223> OTHER INFORMATION: primer

<400> SEQUENCE: 29
ctatgatgta cagcctgaag acctgagttg atac                 34

<210> SEQ ID NO 30
<211> LENGTH: 39
<212> TYPE: DNA
<213> ORGANISM: Artificial
<220> FEATURE:
<223> OTHER INFORMATION: primer

<400> SEQUENCE: 30
attgcatgta cactatctgg ttatagtctc taaactctg            39

<210> SEQ ID NO 31
<211> LENGTH: 37
<212> TYPE: DNA
<213> ORGANISM: Artificial
<220> FEATURE:
<223> OTHER INFORMATION: primer

<400> SEQUENCE: 31
atagcatgta cagaaatcct gtctctaaaa tagcaac              37

<210> SEQ ID NO 32
<211> LENGTH: 35
<212> TYPE: DNA
<213> ORGANISM: Artificial
<220> FEATURE:
<223> OTHER INFORMATION: primer

<400> SEQUENCE: 32
atagcatgta cagatagggt ttctctatgg ctttg                35

<210> SEQ ID NO 33
<211> LENGTH: 33
<212> TYPE: DNA
<213> ORGANISM: Artificial
<220> FEATURE:
<223> OTHER INFORMATION: primer

<400> SEQUENCE: 33
atacgatgta cacctggtgc tgggattaaa ggt      33

<210> SEQ ID NO 34
<211> LENGTH: 35
<212> TYPE: DNA
<213> ORGANISM: Artificial
<220> FEATURE:
<223> OTHER INFORMATION: primer

<400> SEQUENCE: 34
atagcatgta cagggacaag gacataagaa gatag    35

<210> SEQ ID NO 35
<211> LENGTH: 32
<212> TYPE: DNA
<213> ORGANISM: Artificial
<220> FEATURE:
<223> OTHER INFORMATION: primer

<400> SEQUENCE: 35
tagttatgta cactgagttc gagaccagcc tg       32

<210> SEQ ID NO 36
<211> LENGTH: 32
<212> TYPE: DNA
<213> ORGANISM: Artificial
<220> FEATURE:
<223> OTHER INFORMATION: primer

<400> SEQUENCE: 36
atagcatgta cactgtagtc ctcgaccgca ag       32

<210> SEQ ID NO 37
<211> LENGTH: 33
<212> TYPE: DNA
<213> ORGANISM: Artificial
<220> FEATURE:
<223> OTHER INFORMATION: primer

<400> SEQUENCE: 37
atacgaggat cccctggtgc tgggattaaa ggt      33

<210> SEQ ID NO 38
<211> LENGTH: 35
<212> TYPE: DNA
<213> ORGANISM: Artificial
<220> FEATURE:
<223> OTHER INFORMATION: primer

<400> SEQUENCE: 38
atagcaggat ccgatagggt ttctctatgg ctttg    35

<210> SEQ ID NO 39
<211> LENGTH: 24
<212> TYPE: DNA
<213> ORGANISM: Artificial
<220> FEATURE:
<223> OTHER INFORMATION: primer

```
<400> SEQUENCE: 39
ctccacacat ttacacatgg acac                                              24

<210> SEQ ID NO 40
<211> LENGTH: 24
<212> TYPE: DNA
<213> ORGANISM: Artificial
<220> FEATURE:
<223> OTHER INFORMATION: primer

<400> SEQUENCE: 40
gggtttctct gtgtaatagc catg                                              24

<210> SEQ ID NO 41
<211> LENGTH: 24
<212> TYPE: DNA
<213> ORGANISM: Artificial
<220> FEATURE:
<223> OTHER INFORMATION: primer

<400> SEQUENCE: 41
atctcactgt gtctaccaac ttag                                              24

<210> SEQ ID NO 42
<211> LENGTH: 22
<212> TYPE: DNA
<213> ORGANISM: Artificial
<220> FEATURE:
<223> OTHER INFORMATION: primer

<400> SEQUENCE: 42
tctgcaccac cactacctga ct                                                22

<210> SEQ ID NO 43
<211> LENGTH: 28
<212> TYPE: DNA
<213> ORGANISM: Artificial
<220> FEATURE:
<223> OTHER INFORMATION: primer

<400> SEQUENCE: 43
ctaagagtac ttgccatgag agcctgaa                                          28

<210> SEQ ID NO 44
<211> LENGTH: 25
<212> TYPE: DNA
<213> ORGANISM: Artificial
<220> FEATURE:
<223> OTHER INFORMATION: primer

<400> SEQUENCE: 44
cattgataca ccaccaaaga acttg                                             25
```